(12) United States Patent
Minucci et al.

(10) Patent No.: US 8,058,273 B2
(45) Date of Patent: Nov. 15, 2011

(54) HISTONE DEACETYLASES INHIBITORS

(75) Inventors: Saverio Minucci, Noverasco Opera (IT); Pier Giuseppe Pelicci, Opera (IT); Antonello Mai, Rome (IT); Marco Ballarini, Milan (IT); Gaetano Gargiulo, S. Agnello (IT); Silvio Massa, Rome (IT)

(73) Assignee: DAC S.R.L., Milan (IT)

(*) Notice: Subject to any disclaimer, the term of this patent is extended or adjusted under 35 U.S.C. 154(b) by 0 days.

(21) Appl. No.: 12/791,465

(22) Filed: Jun. 1, 2010

(65) Prior Publication Data

US 2010/0240660 A1 Sep. 23, 2010

Related U.S. Application Data

(62) Division of application No. 11/664,187, filed as application No. PCT/EP2005/054949 on Sep. 30, 2005, now Pat. No. 7,803,800.

(30) Foreign Application Priority Data

Oct. 1, 2004 (IT) .............. MI2004A1869

(51) Int. Cl.
| | |
|---|---|
| A61K 31/165 | (2006.01) |
| A61K 31/341 | (2006.01) |
| A61K 31/381 | (2006.01) |
| A61K 31/44 | (2006.01) |
| A61K 31/4436 | (2006.01) |
| A61K 31/5375 | (2006.01) |
| A61P 35/00 | (2006.01) |
| C07C 259/06 | (2006.01) |
| C07D 213/46 | (2006.01) |
| C07D 295/155 | (2006.01) |
| C07D 307/54 | (2006.01) |
| C07D 307/80 | (2006.01) |
| C07D 333/24 | (2006.01) |
| C07D 333/56 | (2006.01) |
| C07D 409/06 | (2006.01) |

(52) U.S. Cl. .............. 514/238.2; 514/336; 514/355; 514/448; 514/471; 514/575; 544/168; 546/280.4; 546/315; 549/57; 549/72; 549/468; 549/488; 562/621

(58) Field of Classification Search ........... 514/238.2, 514/336, 355, 448, 471, 575; 544/168; 546/280.4, 546/315; 549/57, 72, 468, 488; 562/621
See application file for complete search history.

(56) References Cited

FOREIGN PATENT DOCUMENTS

| | | |
|---|---|---|
| WO | 95/13264 A1 | 5/1995 |
| WO | 01/38322 A1 | 5/2001 |
| WO | 02/22577 A2 | 3/2002 |
| WO | 02/26696 A1 | 4/2002 |
| WO | 02/30879 A2 | 4/2002 |
| WO | 03/087066 A1 | 10/2003 |
| WO | 2004/063169 A1 | 7/2004 |
| WO | 2005/040101 A1 | 5/2005 |
| WO | 2005/040161 A1 | 5/2005 |
| WO | 2006/037761 A1 | 4/2006 |
| WO | 2007/113249 A2 | 10/2007 |

OTHER PUBLICATIONS

Golub et al., "Molecular Classification of Cancer: Class Discovery and Class Prediction by Gene Expression Monitoring", Science, vol. 286, Oct. 15, 1999, pp. 531-537.*
Lin et al. "Transcriptional regulation in acute promyelocytic leukemia" Oncogene, 2001, vol. 20, pp. 7204-7215.*
Grignani et al. "Fusion proteins of the retinoic acid receptor-a recruit histone deacetylase in promyelocytic leukaemia" Nature, 1998, vol. 391, pp. 815-818.*
Lutterbach et al. "ETO, a Target of t(8;21) in Acute Leukemia, Interacts with the N-CoR and mSin3 Corepressors" Mol. Cell. Biol., 1998; vol. 18, pp. 7176-7184.*
James R Davie, "Covalent modifications of histones: expression from chromatin templates," Current Opinion in Genetics & Development, 1998, 173-178, vol. 8, Current Biology Ltd ISSN 0959-437X.
Jiansheng Wu et al., "25 years after the nucleosome model: chromatin modifications," TIBS 25, Dec. 2000, 619-623, Elsevier Science Ltd.
Richard J Lin et al., "Transcriptional regulation in acute promyelocytic leukemia," Oncogene, 2001, 7204-7215, vol. 20, Nature Publishing Group.
Arthur Zelent et al., "Translocations of the RAR∝ gene in acute promyelocytic leukemia," Oncogene, 2001, 7186-7203, vol. 20, Nature Publishing Group.
Pier Paolo Pandolfi, "Transcription therapy for cancer," Oncogene, 2001, 3116-3127, vol. 20, Nature Publishing Group.

(Continued)

Primary Examiner — Joseph Kosack
(74) Attorney, Agent, or Firm — McCormick, Paulding & Huber LLP

(57) ABSTRACT

New inhibitors of histone deacetylases having antitumor activity, and the process of preparation thereof are herein described. These compounds belong to the structural formula (I)

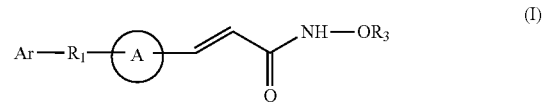

where $R_1$ is a linear or branched chain containing at least two conjugated double bonds, A is an optionally substituted phenyl or pyridyl ring, Ar is an aryl or heteroaryl group, and $R_3$ is hydrogen or alkoxyalkyl. The application also describes the use of said compounds in the treatment of diseases associated to the deregulation of histone deacetylases activity, such as tumors, as well as the relevant pharmaceutical compositions for administration to patients requiring said treatment.

3 Claims, 6 Drawing Sheets (4 of 6 Drawing Sheet(s) Filed in Color)

OTHER PUBLICATIONS

Francesco Grignani et al., "Fusion proteins of the retinoic acid receptor-α recruit histone deacetylase in promyelocytic leukaemia," Nature, Feb. 19, 1998, 815-818, vol. 391, MacMillan Publishers Ltd.

Bart Lutterbach et al., "ETO, a Target of t(8;21) in Acute Leukemia, Interacts with the N-CoR and mSin3 Corepressors," Molecular and Cellular Biology, Dec. 1998, 7176-7184, vol. 18, No. 12, American Society for Microbiology.

Robert J Ferrante et al., "Histone Deacetylase Inhibition by Sodium Butyrate Chemotherapy Ameliorates the Neurodegenerative Phenotype in Huntington's Disease Mice," The Journal of Neuroscience, Oct. 15, 2003, 9418-9427, vol. 23, No. 28, Society for Neuroscience.

Emma Hockly et al., "Suberoylanilide hydroxamic acid, a histone deacetylase inhibitor, ameliorates motor deficits in a mouse model of Huntington's disease," PNAS, Feb. 18, 2003, 2041-2046, vol. 100, No. 4.

Robin S B Williams et al., "A common mechanism of action for three mood-stabilizing drugs," Nature, May 16, 2002, 292-295, vol. 417, MacMillan Magazines Ltd.

Erminio Costa et al., "GABAergic Cortical Neuron Chromatin as a Putative Target to Treat Schizophrenia Vulnerability," Critical Reviews in Neurobiology, 2003, 121-142, vol. 15, No. 2.

Simon P. Chandler et al., "Fragile X (CGG)n repeats induce a transcriptional repression in cis upon a linked promoter: Evidence for a chromatin mediated effect," BMC Molecular Biology, Mar. 21, 2003, vol. 4, No. 3, BMC Molecular Biology.

Pietro Chiurazzi et al., "Synergistic effect of histone hyperacetylation and DNA demethylation in the reactivation of the FMR1 gene," Human Molecular Genetics, 1999, 2317-2323, vol. 8, No. 12, Oxford University Press.

L Bodai et al., "Altered Protein Acetylation in Polyglutamine Diseases," Current Medicinal Chemistry, 2003, 2577-2587, vol. 10, Bentham Science Publishers Ltd.

Robert E Hughes, "Polyglutamine Disease: Acetyltransferases Awry," Current Biology, Feb. 19, 2002, R141-R143, vol. 12, Elsevier Science Ltd.

Mi Ra Jeong et al., "Valproic acid, a mood stabilizer and anticonvulsant, protects rat cerebral cortical neurons from spontaneous cell death: a role of histone deacetylase inhibition," FEBS Letters, 2003, 74-78, vol. 542, Elsevier Science B.V.

Ming Ren et al., "Valproic acid reduces brain damage induced by transient focal cerebral ischemia in rats: potential roles of histone deacetylase inhibition and heat shock protein induction," Journal of Neurochemistry, 2004, 1358-1367, vol. 89, International Society for Neurochemistry.

Hoon Ryu et al., "Histone deacetylase inhibitors prevent oxidative neuronal death independent of expanded polyglutamine repeats via an Sp1-dependent pathway," PNAS, Apr. 1, 2003, 4281-4286, vol. 100, No. 7.

Tiina Suuronen et al., "Regulation of microglial inflammatory response by histone deacetylase inhibitors," Journal of Neurochemistry, 2003, 407-416, vol. 87, International Society for Neurochemistry.

Sara Eyal et al., "The Activity of Antiepileptic Drugs as Histone Deacetylase Inhibitors," Epilepsia, 2004, 737-744, vol. 45, No. 7, Blackwell Publishing Inc, International League Against Epilepsy.

Yunfei Huang et al., "Altered Histone Acetylation at Glutamate Receptor 2 and Brain-Derived Neurotrophic Factor Genes Is an Early Event Triggered by Status Epilepticus," The Journal of Neuroscience, Oct. 1, 2002, 8422-8428, vol. 22, No. 19, Society for Neuroscience.

Lisa J Corcoran et al., "A Novel Action of Histone Deacetylase Inhibitors in a Protein Aggresome Disease Model," Current Biology, Mar. 23, 2004, 488-492, vol. 14, Elsevier Ltd.

Emmanuelle Adam et al., "Potentiation of Tumor Necrosis Factor-Induced NF-kB Activation by Deacetylase Inhibitors Is Associated with a Delayed Cytoplasmic Reappearance of IkBα," Molecular and Cellular Biology, Sep. 2003, 6200-6209, vol. 23, No. 17, American Society for Microbiology.

Carine Van Lint et al., "Transcriptional activation and chromatin remodeling of the HIV-1 promoter in response to histone acetylation," The EMBO Journal, 1996, 1112-1120, vol. 15, No. 5, Oxford University Press.

Dominique Demonte et al., "Administration of HDAC inhibitors to reactivate HIV-1 expression in latent cellular reservoirs: implications for the development of therapeutic strategies," Biochemical Pharmacology, 2004, 1231-1238, vol. 68, Elsevier Inc.

Loyda Ylisastigui et al., "Coaxing HIV-1 from resting CD4 T cells: histone deacetylase inhibition allows latent viral expression," AIDS, 2004, 1101-1108, vol. 18, Lippincott Williams & Wilkins.

Soren Skov et al., "Histone deacetylase inhibitors: a new class of immunosuppressors targeting a novel signal pathway essential for CD154 expression," Blood, Feb. 15, 2003, 1430-1438, vol. 101, No. 4, The American Society of Hematology.

Pavan Reddy et al., "Histone deacetylase inhibitor suberoylanilide hydroxamic acid reduces acute graft-versus-host disease and preserves graft-versus-leukemia effect," PNAS, Mar. 16, 2004, 3921-3926, vol. 101, No. 11, The National Academy of Sciences of the USA.

Hyun Kook et al., "Cardiac hypertrophy and histone deacetylase-dependent transcriptional repression mediated by the atypical homeodomain protein Hop," The Journal of Clinical Investigation, Sep. 2003, 863-871, vol. 112, No. 6.

Timothy A McKinsey et al., "Dual roles of histone deacetylases in the control of cardiac growth," Reversible protein acetylation, 2004, 132-145, 163-169, Novartis Foundation Symposium 259.

Yasuo Hamamori et al., "HATs off to Hop: recruitment of a class I histone deacetylase incriminates a novel transcriptional pathway that opposes cardiac hypertrophy," The Journal of Clinical Investigation, Sep. 2003, 824-826, vol. 112, No. 6.

Krista Rombouts et al., "Trichostatin A, a Histone Deacetylase Inhibitor, Suppresses Collagen Synthesis and Prevents TGF-β1-Induced Fibrogenesis in Skin Fibroblasts," Experimental Cell Research, 2002, 184-197, vol. 278, Elsevier Science.

Toshiro Niki et al., "A Histone Deacetylase Inhibitor, Trichostatin A, Suppresses Myofibroblastic Differentiation of Rat Hepatic Stellate Cells in Primary Culture," Hepatology, Mar. 1999, 858-867, vol. 29, No. 3, The American Association for the Study of Liver Diseases.

Makoto Minamiyama et al., "Sodium butyrate ameliorates phenotypic expression in a transgenic mouse model of spinal and bulbar muscular atrophy," Human Molecular Genetics, 2004, 1183-1192, vol. 13, No. 11, Oxford University Press.

Yih-Lin Chung et al., "A Therapeutic Strategy Uses Histone Deacetylase Inhibitors to Modulate the Expression of Genes Involved in the Pathogenesis of Rheumatoid Arthritis," Molecular Therapy, Nov. 2003, 707-717, vol. 8, No. 5, The American Society of Gene Therapy.

Nilamadhab Mishra et al., "Histone deacetylase inhibitors modulate renal disease in the MRL-lpr/lpr mouse," The Journal of Clinical Investigation, Feb. 2003, 539-552, vol. 111, No. 4.

Fiona McLaughlin et al., "Histone Deacetylase Inhibitors in Psoriasis Therapy," Current Drug Targets—Inflammation & Allergy, 2004, 213-219, vol. 3, Bentham Science Publishers Ltd.

Marcus D Saemann et al., "Short-chain fatty acids: bacterial mediators of a balanced host-microbial relationship in the human gut," Wien Klin Wochenschr, 2002, 289-300, vol. 114, No. 8-9.

Griffin P. Rodgers et al., "Advances in experimental treatment of β-thalassaemia," Expert Opinion on Investigational Drugs, 2001, 925-934, vol. 10, No. 5, Ashley Publications Ltd.

Peter J Barnes, "Pulmonary Perspective—Theophylline—New Perspectives for an Old Drug," Am J Respir Crit Care Med, 2003, 813-818, vol. 167.

Juan M Alarcon et al., "Chromatin Acetylation, Memory, and LTP Are Impaired in CBP+/- Mice: A Model for the Cognitive Deficit in Rubinstein-Taybi Syndrome and its Amelioration," Neuron, Jun. 24, 2004, 947-959, vol. 42, Cell Press.

Paul A Marks, MD et al., "Histone deacetylase inhibitors as new cancer drugs," Current Opinion in Oncology, 2001, 477-483, vol. 13, Lippincott Williams & Wilkins, Inc.

Ricky W Johnstone, "Histone-Deacetylase Inhibitors: Novel Drugs for the Treatment of Cancer," Nature Reviews—Drug Discovery, Apr. 2002, 287-299, vol. 1, Nature Publishing Group.

Keith B Glaser, "HDAC inhibitors: Clinical update and mechanism-based potential," Biochemical Pharmacology, 2007, 659-671, vol. 74, Elsevier Inc.

David M Vigushin et al., "Histone deacetylase inhibitors in cancer treatment," Anti-Cancer Drugs, 2002, 1-13, vol. 13, Lippincott Williams & Wilkins.

Thomas A Miller, "Patent status of histone deacetylase inhibitors," Expert Opin. Ther. Patents, 2004, 791-804, vol. 14, No. 6, Ashley Publications Ltd.

Thomas A Miller et al., "Histone Deacetylase Inhibitors," Journal of Medicinal Chemistry, Nov. 20, 2003, 5097-5116, vol. 46, No. 24, The American Chemical Society.

Oscar Moradei et al., "Histone Deacetylase Inhibitors: Latest Developments, Trends and Prospects," Curr. Med. Chem.—Anti-Cancer Agents, 2005, 529-560, vol. 5, Bentham Science Publishers Ltd.

Saverio Minucci et al., "Histone deacetylase inhibitors and the promise of epigenetic (and more) treatments for cancer," Nature Reviews—Cancer, Jan. 2006, 38-51, vol. 6, Nature Publishing Group.

Michael Curtin et al., "Histone Deacetylase Inhibitors: The Abbott Experience," Current Medicinal Chemistry, 2003, 2373-2392, vol. 10, Bentham Science Publishers Ltd.

Robert P. Sheridan., "The Most Common Chemical Replacements in Drug-Like Compounds," J. Chem. Inf. Comput. Sci, Jan. 3, 2002, 103-108, vol. 42, American Chemical Society.

Antonello Mai et al., "Discovery of (Aryloxopropenyl)pyrrolyl Hydroxyamides as Selective Inhibitors of Class IIa Histone Deacetylase Homologue HDI-A," J. Med. Chem., Oct. 15, 2003, 4826-4829, vol. 46, American Chemical Society.

A. Mai, et al., "Synthesis and Biological Evaluation of 2-, 3-, and 4-Acylaminocinnamyl-N-hydroxyamides as Novel Synthetic HDAC Inhibitors," Medicinal Chemistry, 2005, 245-254, vol. 1, Bentham Science Publishers Ltd.

Paul W. Finn, et al., "Novel Sulfonamide Derivatives as Inhibitors of Histone Deacetylase," Helvetica Chimica Acta, 2005, 1630-1657, vol. 88, Verlag Helvetica Chimica Acta AG.

Peeyush K. Lala et al., "Role of nitric oxide in tumor progression: Lessons from experimental tumors," Cancer and Metastasis Reviews, 1998, 91-106, vol. 17, Kluwer Academic Publishers.

T. R. Golub et al., "Molecular Classification of Cancer: Class Discovery and Class Prediction by Gene Expression Monitoring," Reports, Oct. 15, 1999, 531-536, vol. 286, Science.

Cancer [online], retrieved on Jul. 6, 2007 from the internet, URL http://www.nlm.nih.gov/medlineplus/print/cancer.html.

Cancer [online], retrieved on Jul. 6, 2007 from the internet, URL http://en.wikipedia.org/wiki/Cancer.

Milin R. Acharya et al., "Rational Development of Histone Deacetylase Inhibitors as Anticancer Agents: A Review," Mol Pharmacol, 2005, 917-932, vol. 68, No. 4.

Paul A. Marks et al., "Histone Deacetylase Inhibitors: Inducers of Differentiation or Apoptosis of Transformed Cells," Journal of the National Cancer Institute, Aug. 2, 2000, 1210-1216, vol. 92, No. 15, Oxford University Press.

International Search Report from PCT/EP2005/054949 dated Feb. 24, 2006 (4 pages).

International Search Report from PCT/EP2007/053097 dated Sep. 12, 2007 (2 pages).

International Search Report from PCT/EP2008/061140 dated Feb. 5, 2009 (2 pages).

Written Opinion of the International Searching Authority from PCT/EP2008/061140 (4 pages), 2009.

* cited by examiner

HISTONE DEACETYLASES INHIBITORS

CROSS REFERENCE TO RELATED APPLICATIONS

This application is a divisional of U.S. patent application Ser. No. 11/664,187 filed on Mar. 28, 2007 which is entitled to the benefit of and incorporates by reference essential subject matter disclosed in International Patent Application No. PCT/EP2005/054949 filed on Sep. 30, 2005 and Italian Patent Application No. MI2004A001869 filed Oct. 1, 2004.

FIELD OF THE INVENTION

The present invention relates to the field of antitumor compounds. New inhibitors of histone deacetylases with cinnamoylamidic structure are herein described, useful in the treatment of diseases linked to the deregulation of histone deacetylases activity, such as in antitumor therapy.

BACKGROUND OF THE INVENTION

The reversible histone acetylation taking place on the ε-amino group of the lysine residue in the histone N-terminal section mediates important conformational modifications within the nucleosomes. These modifications affect DNA capability to access transcription factors as well as genic expression (*Curr. Opin. Genet. Dev.* 1998, 8, 173-178). Two classes of enzymes are involved in histone acetylation: histone acetyltransferases (HATs), which catalyse histone acetylation by acting as transcription co-activators, and histone deacetylases (HDACs); the latter enzymes are recruited at the level of promoter regions by transcription repressors and co-repressors such as Sin3, SMRT, and N—CoR, leading to the formation of hypoacetylated histones and transcription silencing (*Trends Biochem. Sci.* 2000, 25, 619-623). The aberrant recruitment of histone deacetylases through oncogenic proteins, or the disturbed balance of activities of histone acetyltransferases and histone deacetylases in normal cells are involved in a number of pathologies:

first of all, in tumor diseases (*Oncogene* 2001, 20, 7204-7215, 7186-7203, 3116-3127; *Nature* 1998, 391, 815-818; *Mol. Cell. Biol.* 1998, 18, 7176-7184).

in several non-tumor diseases:

Nervous system:
Huntington's disease (*J Neurosci* 23, 9418-27 (2003); *Proc Natl Acad Sci USA* 100, 2041-6 (2003)), diseases caused by triplette amplifications (*Curr Med Chem* 10, 2577-87 (2003); *Curr Biol* 12, R141-3 (2002)), neuroprotection against degenerative diseases (*FEBS Lett* 542, 74-8 (2003); ischemia (*J Neurochem* 89, 1358-67 (2004)), oxidative stress (*Proc Natl Acad Sci USA* 100, 4281-6 (2003)), inflammatory responses of the nervous system (*J Neurochem* 87, 407-16 (2003)), epilepsy (*Epilepsia* 45, 737-44 (2004), *J Neurosci* 22, 8422-8 (2002)), diseases caused by protein aggregates (*Curr Biol* 14, 488-92 (2004)).

Infection:
HIV (*Mol Cell Biol* 23, 6200-9 (2003), *Embo J* 15, 1112-20 (1996), *Biochem Pharmacol* 68, 1231-8 2004), *Aids* 18, 1101-8 (2004)), malaria, leishmaniosis, infections caused by protozoa, fungi, phytotoxic agents, virus, parasites.

Immune system:
autoimmune diseases (*Blood* 101, 1430-8 (2003)), chronic host-directed immune reaction (*Proc Natl Acad Sci USA* 101, 3921-6 (2004)).

Heart:
hypertrophy and cardiac disorders (*J Clin Invest* 112, 863-71 (2003), *Novartis Found Symp* 259, 132-41, discussion 141-5, 163-9 (2004), *J Clin Invest* 112, 824-6 (2003)).

Muscular apparatus:
skin fibrotic disease (*Exp Cell Res* 278, 184-97 (2002)), fibrosis (*Hepatology* 29, 858-67 (1999)), spinal and bulbar muscular atrophy, (*Hum Mol Genet.* 13, 1183-92 (2004)).

Psychic system:
bipolar disorders (*Nature* 417, 292-5 (2002)), psychiatric disorders (*Crit Rev Neurobiol* 15, 121-42 (2003)), X-fragile syndrome (*BMC Mol Biol* 4, 3 (2003), *Hum Mol Genet* 8, 2317-23 (1999)).

Others:
arthritis (*Mol Ther* 8, 707-17 (2003)), renal diseases (*J Clin Invest* 111, 539-52 (2003)), psoriasis (*Curr Drug Targets Inflamm Allergy* 3, 213-9 (2004)), intestinal diseases, colitis (*Wien Klin Wochenschr* 114, 289-300 (2002)), beta thalassemy (*Expert Opin Investig Drugs* 10, 925-34 (2001)), respiratory diseases (*Am J Respir Crit. Care Med* 167, 813-8 (2003)), Rubinstein-Taybi syndrome (*Neuron* 42, 947-59 (2004)).

Histone deacetylases inhibitors, such as the natural products tricostatin A (TSA), trapoxin (TPX), and depsipeptide FK-228, short chain fatty acids, sodium butyrrate, phenylbutyrrate and valproate, hydroxamic acid, hydroxamates such as the suberoylanilide hydroxamic acid (SAHA), pyroxamide, scriptaid, oxamflatin, NVP-LAQ824, cyclic peptides containing hydroxamic acid (CHAPs), and the benzamide MS-275 strongly promote growth interruption, differentiation and apoptosis in a number of transformed cells in culture and in animal models (*Curr. Opin. Oncol.* 2001, 13, 477-483). Among them, sodium phenylbutyrate (alone or in combination), depsipeptide, SAHA, pyroxamide, NVP-LAQ824, MS-275, are in clinical phase I and/or II for the treatment of several cancerous diseases (*Nat. Rev. Drug Discov.* 2002, 1, 287-299). Nevertheless their clinical utility is restricted by toxicity problems (TSA, CHAPs, MS-275), low stability (TSA, trapoxin), low solubility (TSA), low potency and lack of selectivity (butyrates and analogues) (*Anti-Cancer Drugs* 2001, 13, 1-13).

WO 04/063169 discloses hydroxamic acid derivatives as HDAC inhibitors with the following general formula:

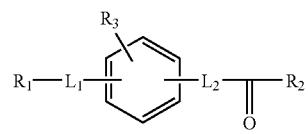

with $R^1$ is a N-containing heterocyclic ring optionally substituted with one or more suitable groups, $R^2$ is hydroxylamino, $R^3$ is hydrogen or a suitable substituent, $L^1$ is —$(CH_2)_n$— with n an integer of 0 to 6, optionally substituted with one or more suitable substitutents and wherein one or more methylene(s) may be replaced with suitable heteroatom(s); $L^2$ is a lower alkylene chain.

WO 03/087066 describes hydroxamic acid derivatives and their use as histone deacetylase inhibitors with the following formula

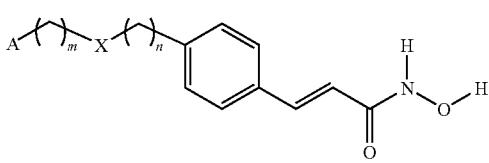

where A is an optionally substituted phenyl or aromatic heterocyclic group; m and n independently an integer from 0 to 4; and X is a moiety having a structure selected from

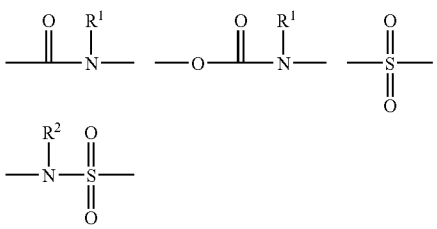

where $R^2$ is hydrogen or optionally substituted $C_1$-$C_4$ alkyl.

WO 02/22577 discloses the following hydroxamic acid derivatives as deacetylase inhibitors of general formula

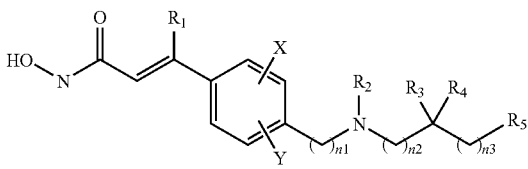

where $R^1$ is hydrogen, halogen or a $C_1$-$C_6$ alkyl chain, $R_2$ is selected from H, $C_1$-$C_{10}$ alkyl, $C_4$-$C_9$ cycloalkyl, $C_4$-$C_9$ heterocycloalkyl, cycloalkylalkyl, aryl, heteroaryl etc.; $R_3$ and $R_4$ are independently selected from hydrogen, $C_1$-$C_6$ alkyl, acyl or acylamino $R_5$ is selected from hydrogen, $C_1$-$C_6$ alkyl and others; $n_1$, $n_2$ and $n_3$ are an integer from 0 to 6, X and Y are selected from hydrogen, halogen, $C_1$-$C_4$ alkyl etc.

WO 01/38322 describes histone deacetylase inhibitors of the general formula

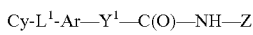

Cy-L$^1$-Ar—Y$^1$—C(O)—NH—Z where Cy is an optionally substituted cycloalkyl, aryl, heteroaryl or heterocyclyl ring; $L^1$ is —(CH$_2$)$_m$—W with m an integer from 0 to 4, W is selected among others from C(O)NH—, S(O)$_2$—NH—; Ar is an optionally substituted arylene ring, wherein said arylene may be optionally fused to an aryl or heteroaryl ring, $Y^1$ is a bond or a saturated alkylene chain; Z is among other groups O-M, wherein M is hydrogen or a suitable pharmaceutical cation ion.

WO 95/13264 discloses hydroxamic acid derivatives of general formula

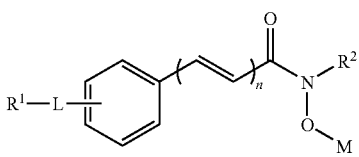

wherein $R^1$ represents among other groups phenyl or aryloxyphenyl; L is $C_1$-$C_8$ alkylene, $C_2$-$C_8$ alkenylene, (CH$_2$)$_m$—O— (wherein m is an integer from 0 to 4), or —CO—; n is 0 or 1; $R^2$ is hydrogen, $C_1$-$C_4$ alkyl or arylalkyl; M is hydrogen, alkoyl, alkoxycarbonyl; and their use as medicinal having the effect of suppressing smooth muscle growth and being usable as a vascular wall thickening preventive, a post-PTCA retenosis preventive and even an antiarterosclerotic agent.

Mai et al. describe in *J. Med. Chem.* 2001, 44, 2069-2072, *J. Med. Chem.* 2002, 45, 1778-1784, *J. Med. Chem.* 2003, 46, 512-524, *J. Med. Chem.* 2003, 46, 4826-4829, *J. Med. Chem.* 2004, 47, 1098-1109, *J. Med. Chem.* 2004, 47, 1351-1359 and *J. Med. Chem.* 2005, 48, 3344-3353 pyrrolyl hydroxamide derivatives as selective HDAC inhibitors.

Further HDAC inhibitors are discussed in *Expert Opin. Ther. Patents* 2004, 14(6), 791-804). Histone deacetylases inhibitors were also identified with different affinities with respect to specific subclasses of histone deacetylases (HD2, HD1-A, HD1-B): the discriminating ability among the various subclasses of histone deacetylases leads to important consequences: i.e. the elimination of side effects and/or the activity towards specific forms of tumor.

However, none of the aforementioned compounds has so far shown a fully satisfactory profile. It is thus still desired to find new histone deacetylases inhibitors having useful antitumor properties, adequate selectivity and stability of action; also, the search is open for new inhibitors having high activity on histone deacetylases, possibly showing a higher activity with respect to specific subclasses thereof.

BRIEF SUMMARY OF THE INVENTION

We have now found a new group of histone deacetylase inhibitors with high and stable antitumor activity. These inhibitors are described by the following general formula (I)

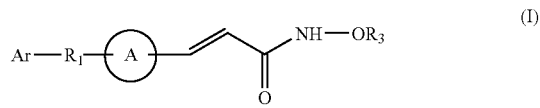

wherein:
$R_1$ is a linear or branched chain, containing at least two conjugated double bonds,
$R_3$ is chosen among hydrogen, alkoxyalkyl;
Ar is an optionally substituted aryl or heteroaryl group.
A is chosen among:

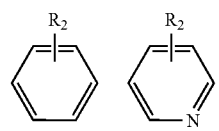

wherein $R_2$ is chosen among hydrogen, alkyl, cycloalkyl, aryl, arylalkyl, heterocyclyl, heterocyclylalkyl, halogen, haloalkyl, hydroxy, hydroxyalkyl, alkoxy, haloalkoxy, amino, aminoalkyl, alkylamino, (thio)carbonylamino, (thio)aminocarbonil, sulphonylamino, aminosulphonyl, (thio)acyl, (thio)acyloxy, (thio)alkoxycarbonyl, nitro and nitryl;

The compounds of formula (I) can be synthesised by treating a compound of formula (II) where A and $R_2$ have the aforesaid meanings and $R_4$ is a suitable leaving group, for example a halogen like bromine or iodine:

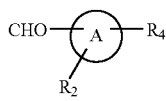

(i) with a compound of formula Ar—W, where Ar has the aforesaid meanings, and W is a group capable to form, by reaction with the CHO group of (II), the group $R_1$ as defined above, or a synthesis intermediate thereof, (ii) and further with a compound of formula (III)

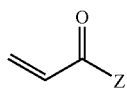

where Z represents the group $NHOR_3$ as defined above or a precursor thereof, and where the steps (i) and (ii) may take place in any order.

The compounds of formula (I) are strong inhibitors of histone deacetylases, with $IC_{50}$ in the order of 1 µM or lower. These compounds present broad spectrum and stable activity in the course of time: both features are ideal from the point of view of therapeutic application. Furthermore, the compounds of formula (I) strongly promote apoptosis and inhibit cell proliferation on a panel of tumor cells.

The invention includes the use of the compounds of formula (I) in the treatment and/or prevention of diseases associated with the deregulation of histone deacetylases activities and the relevant pharmaceutical compositions for administration of said compounds.

BRIEF DESCRIPTION OF THE DRAWINGS

The file of this patent contains at least one drawing executed in color. Copies of this patent with color drawing(s) will be provided by the Office upon request and payment of the necessary fee.

DETAILED DESCRIPTION OF THE INVENTION

Figure 1:
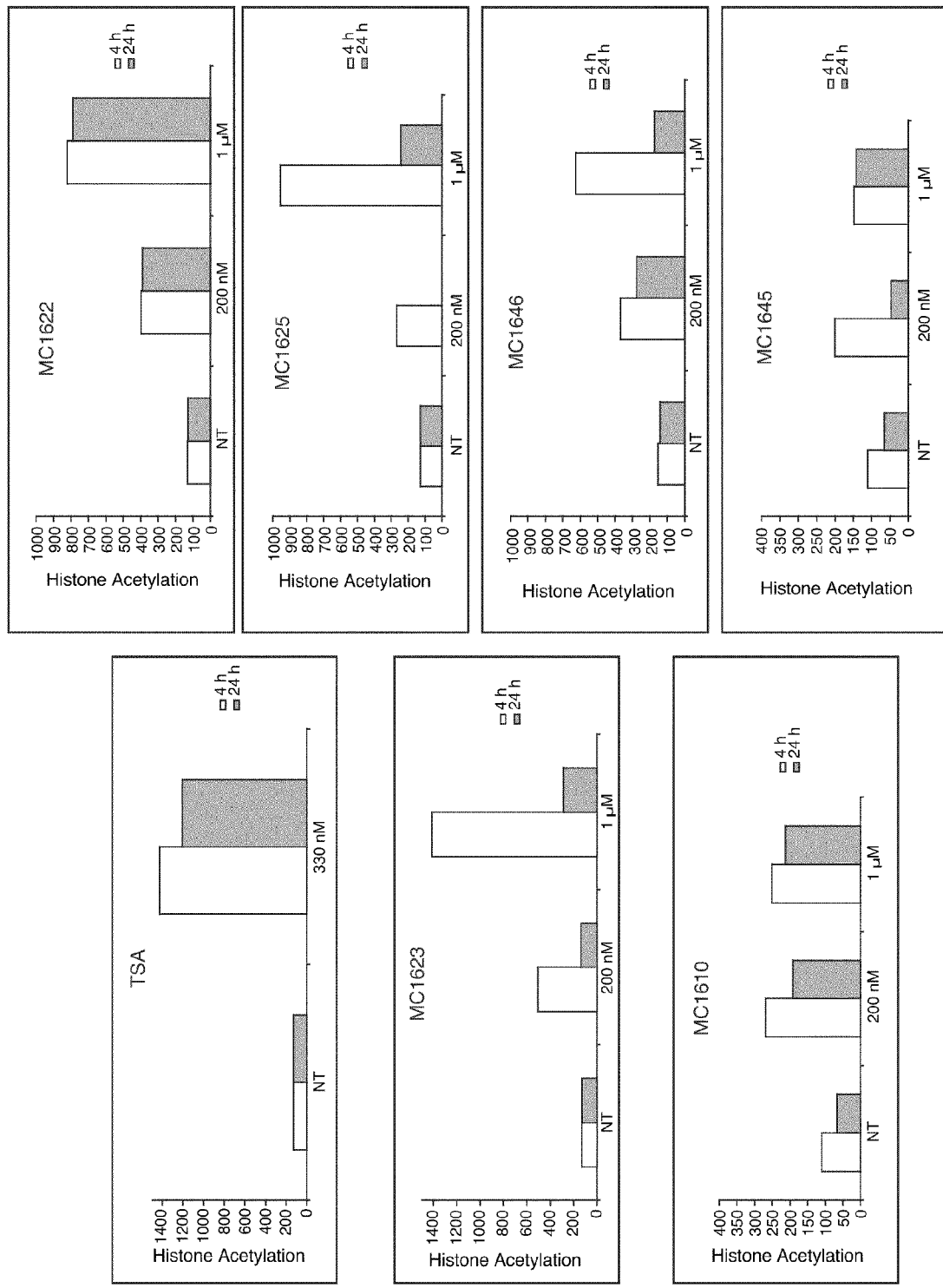
FIG. 1 is a result of the treatment of U937 cells with the compounds indicated (200 nM, 1 µM) for 4 h and 24 h.

In the aforementioned formula (I) the alkyl groups, either alone or comprised within higher structures (e.g. alkoxy, arylalkyl, etc.), contain preferably from 1 to 8, (more preferably from 1 to 4) carbon atoms and can be linear or branched, and possibly substituted.

The acyl groups, either alone or comprised within higher structures (e.g. acyloxy), preferably contain from 1 to 8, more preferably from 1 to 4 carbon atoms and can be linear or branched, saturated or unsaturated, and possibly substituted.

The cycloalkyl group preferably contain from 3 to 8, more preferably from 3 to 6 carbon atoms and can be saturated or unsaturated, and possibly substituted.

The aryl groups, either alone or comprised within higher structures (e.g. arylalkyl), are aromatic monocyclic or polycyclic rings, preferably containing from 6 to 10 carbon atoms per ring, possibly substituted; a preferred example of aryl is the phenyl group.

Heterocyclyl groups, either alone or comprised within higher structures (e.g. heterocycloalkyl), either monocyclic or polycyclic, contain preferably from 4 to 8 members per ring, 1 to 3 members or them being heteroatoms such as N, O, S, and can be saturated or unsaturated and possibly substituted.

In all said possibly substituted groups, the possible substituents can be chosen e.g. among the hydroxy, alkoxy, haloalkoxy, amino, aminocarbonyl, carbonylamino, carbonylamide, amide, carboxyl, alkoxycarbonyl, aminoalkyl, alkylamino, dialkylamino, pyridyl, piperazinyl, morpholyl, halogen, nitro and nitryl function.

To the aforesaid definition of $R_1$ belong any α,β unsaturated functions, including those wherein the α,β unsaturation involves non-carbon atoms, e.g. oxygen, nitrogen, or sulphur atoms. Thus R1 may be a carbon atom chain, or a=Y substituted carbon atom chain wherein Y represents the non-carbon atom involved in the α,β unsaturation. Preferably $R_1$ includes from 3 to 8 carbon atoms; more preferably, $R_1$ is chosen among the following structures:

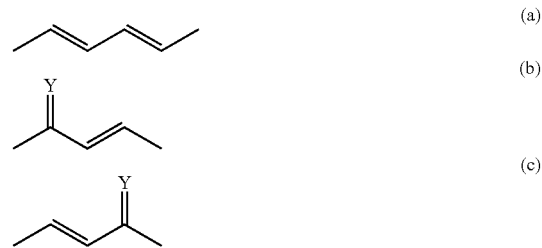

wherein Y is chosen among O, S, NH, $CH_2$, NOH or $NOR_5$ with $R_5$ alkyl from 1 to 4 carbon atoms.

Preferred meanings for the Ar group are: phenyl, naphtyl, pyridyl, pyranyl, pyrrolyl, thienyl, furanyl, benzofuryl, benzothienyl, indolyl.

Whenever present, the optional substituent of the Ar group is preferably chosen among halogen, hydroxy, alkyl, alkoxy, trifluoroalkyl, trifluoroalkoxy, dialkylamino, morpholyl, piperazinyl, metoxycarbonyl.

The connections of the A ring to $R_1$ and to the $R_3$-containing residue are preferably in para relationship to each other on the A ring. The $R_2$ substituent may be attached at any available position of the A ring; preferred meanings for $R_2$ are hydrogen, halogen, alkyl, alkoxy. Preferred meaning for $R_3$ is hydrogen.

Preferred substructures of formula (I) are the following formulas (Ia), (Ib), (Ic) and (Id):

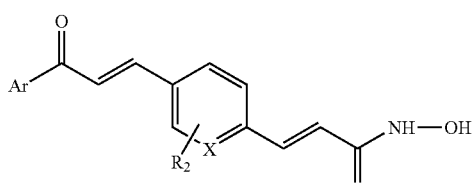
(Ia)

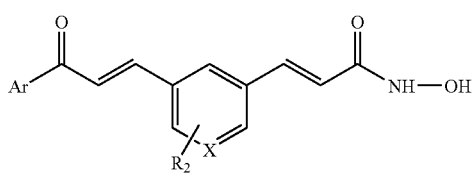
(Ib)

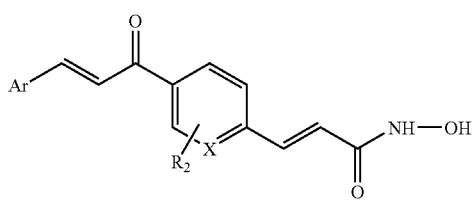
(Ic)

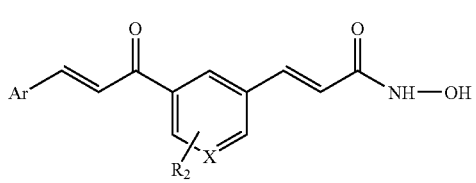
(Id)

where Ar and $R_2$ have the aforesaid meanings, and X is a carbon or nitrogen atom.

The invention further includes a process for the preparation of the compounds of formula (I). In its most general meaning the process includes the treatment of a compound of formula (II)

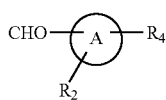
(II)

where A and $R_2$ have the aforesaid meanings and $R_4$ is a suitable leaving group, e.g. a halogen such as bromine and iodine (i) with a compound of formula Ar—W, where Ar has the aforesaid meanings, and W is a group capable to form, by reaction with the CHO group of (II), said $R_1$ group, or a synthetic intermediate thereof, (ii) and further with a compound of formula (III)

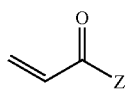
(III)

where Z represents $NHOR_3$ as defined above or a precursor thereof.

The addition reaction of compound Ar—W generally takes place in alkaline environment; preferably the compound Ar—W is an acetophenone optionally substituted on the phenyl ring.

Preferably the compound of formula (III) is an alkylacrylate, more preferably a n-butyl acrylate. The addition of the compound of formula (III) generally takes place in the presence of potassium phosphate and palladium acetate; in case of the alkylacrylates of formula (III) the O-alkyl group works as a precursor of the NHOH group; its conversion to NHOH takes place according to known techniques, as exemplified below.

In particular, the preferred compounds of formula (Ia) can be obtained by deprotection of compounds of formula (IV) or (IVa) according to the following synthetic route:

Scheme 1

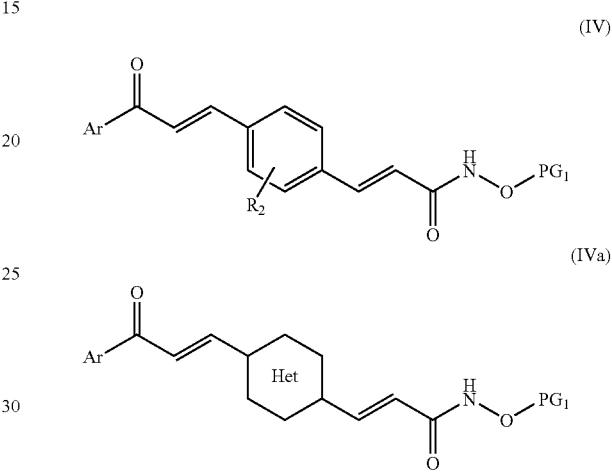

In all formulas herein presented, the ring marked with "Het" represents the pyridine ring:

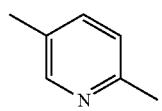

Protecting groups $PG_1$, chosen in accordance with normal chemical practice, are removed by standard methods. When $PG_1$ is a tetrahydropyranyl or 2-methoxy-2-propyl residue, acidic conditions are used such as hydrochloric acid in aprotic solvents (e.g. diethyl ether, dioxane or THF).

Compounds of formula (IV) are obtained by reaction of compounds of formula (V) with protected hydroxylamine ($NH_2OPG_1$)

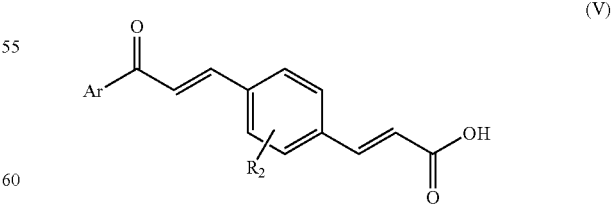
(V)

The coupling reaction may be promoted by coupling agents known in the art of organic synthesis such as EDC (1-(3-dimethylaminopropyl)-3-ethylcarbodiimide), DCC(N, N'-dicyclohexyl-carbodiimide) or by polymer-supported coupling agents such as polymer-supported carbodiimide (PS-DCC, ex Argonaut Technologies), in the presence of a suitable base such as triethylamine, diisopropylethylamine, in a suitable solvent (e.g. tetrahydrofuran, dichloromethane, N,N-dimethylformamide).

Typically, a co-catalyst such as HOBT (1-hydroxy-benzotriazole), HOAT (1-hydroxy-7-azabenzotriazole) and the like may also be present in the reaction mixture. The reaction typically proceeds at room temperature for a time in the range of about 2 hours up to 12 hours.

Compounds of formula (V) can be obtained by reaction of compounds of formula (VI)

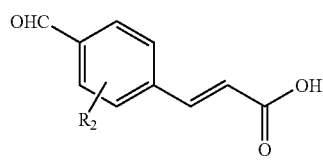

(VI)

with compounds of formula (VII)

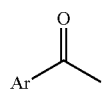

(VII)

in presence of an inorganic base such as KOH or NaOH in protic solvent, such as ethanol, methanol or water. The reaction typically proceeds from 0° C. to room temperature for a time in the range of about 2 hours up to 12 hours.

The compounds of formula (VII) are known commercially available compounds or they can be prepared from known compounds by known methods, or methods analogous to those used to prepare known compounds.

The compounds of formula (VI) are commercially available or can be prepared by reaction of compounds of formula (VIII), whereas B is halogen, in particular bromo or iodo,

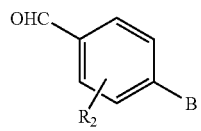

(VIII)

with tert-butylacrylate using classical Heck reaction conditions as described by Larhed, M.; Hallberg, A. in Handbook of Organopalladium Chemistry for Organic Synthesis; Negishi, E., Ed.; Wiley-Interscience: New York, 2002. The reaction takes place in presence of palladium salts, such as palladium acetate, organic and inorganic bases (triethylamine, 1,4-diazabicyclo[2.2.2]octane and sodium bicarbonate or potassium bicarbonate) and, eventually, phosphine derivatives, such as triphenylphospine in DMF. The reaction typically proceeds from room temperature to reflux, usually at 100° C., for a time in the range of about 2 hours up to 12 hours. Suitable deprotection methods for tert-butyl ester conversion into the corresponding carboxylic acid will be those used conventionally in the art with reference to standard texts such as Greene, T. W. and Wuts, P. G. M. Protective Groups in Organic Synthesis, John Wiley & Sons Inc. New York, 1991 (Second Edt.) or in Kocienski, P. J. Protecting groups. George Thieme Verlag, New York, 1994.

The compounds of formula (VIII) are known commercially available compounds or they can be prepared from known compounds by known methods, or methods analogous to those used to prepare known compounds.

Alternatively compounds of formula (V) can be obtained by reaction of compounds of formula (IX)

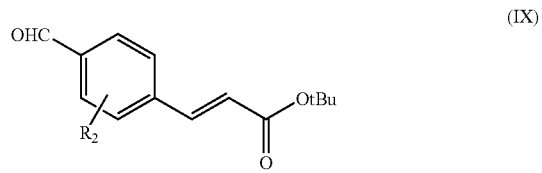

(IX)

with compounds of formula (VII) in presence of an inorganic base such as KOH or NaOH in protic solvent, such as ethanol, methanol or water. The reaction typically proceeds from 0° C. to room temperature for a time in the range of about 2 hours up to 12 hours. Suitable deprotection methods for tert-butyl ester conversion into the corresponding carboxylic acid will be those used conventionally in the art.

The compounds of formula (IX) can be prepared by reaction of compounds of formula (VIII), whereas B is halogen in particular bromo or iodo, with tert-butylacrylate using classical Heck conditions similar to those described for the synthesis of compounds of formula (VI).

Alternatively compounds of formula (V) can be obtained by reaction of compounds of formula (X)

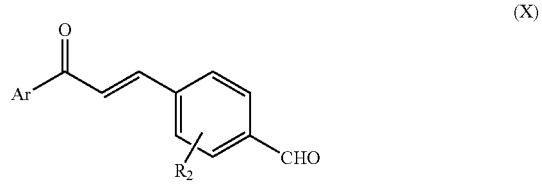

(X)

with tert-butyldiethylphosphonoacetate in presence of an inorganic base such as sodium hydride in aprotic solvent such as THF. The reaction typically proceeds from 0° C. to room temperature for a time in the range of about 1 hour up to 12 hours. Suitable deprotection methods for tert-butyl ester conversion into the corresponding carboxylic acid will be those used conventionally in the art.

Compounds of formula (X) can be prepared by reaction of compounds of formula (XI)

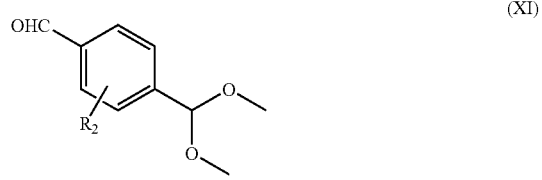

(XI)

with compounds of formula (VII) in presence of an inorganic base such as KOH or NaOH in protic solvents such as ethanol, methanol or water. The reaction typically proceeds from 0° C. to room temperature for a time in the range of about 1 hour up to 12 hours. Suitable deprotection methods for dimethyl acetal conversion into the corresponding aldehyde will be those used conventionally in the art with reference to standard texts such as Greene, T. W. and Wuts, P. G. M. Protective Groups in Organic Synthesis, John Wiley & Sons Inc. New York, 1991 (Second Edt.) or in Kocienski, P. J. Protecting groups. George Thieme Verlag, New York, 1994.

Compounds of formula (XI) can be prepared by reaction of compounds of formula (XII)

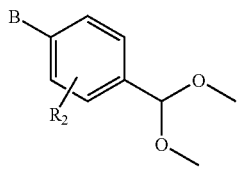

(XII)

whereas B is halogen, in particular bromo or iodo, with an alkyl lithium, such as n-butyl lithium, followed by addition of DMF in aprotic solvent such as THF. The reaction typically proceeds from −78° C. to room temperature for a time in the range of about 1 hour up to 3 hours.

Compounds of formula (XII) can be obtained from compounds of formula (VIII) by conversion of aldehyde in the corresponding dimethyl acetale using suitable protection methods that will be those used conventionally in the art.

Alternatively compounds of formula (V) can be obtained by reaction of compounds of formula (XIII) whereas B is halogen, in particular bromo or iodo,

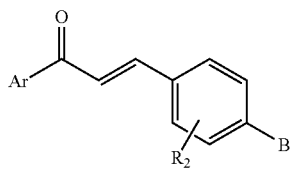

(XIII)

with tert-butylacrylate using classical Heck conditions similar to those described for the synthesis of compounds of formula (VI). Deprotection of the tert-butyl ester is carried out according to the known standard procedures.

Compounds of formula (XIII) can be prepared by reaction of compounds of formula (VIII) with compounds of formula (VII) in presence of an organic or inorganic base such as KOH or NaOH in protic solvent, such as ethanol, methanol or water. The reaction typically proceeds from 0° C. to reflux, for a time in the range of about 1 hour to 36 hours.

When A is an heteroaryl, compounds of formula (IVa) are obtained by reaction of compounds of formula (XIV) with protected hydroxylamine (NH$_2$OPG$_1$).

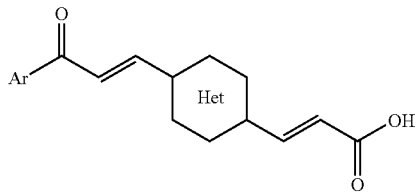

(XIV)

The coupling reaction may be promoted by coupling agents known in the art of organic synthesis such as EDC (1-(3-dimethylaminopropyl)-3-ethylcarbodiimide), DCC(N, N'-dicyclohexyl-carbodiimide) or by polymer-supported coupling agents such as polymer-supported carbodiimide (PS-DCC, ex Argonaut Technologies), in the presence of a suitable base such as triethylamine, diisopropylethylamine, in a suitable solvent (e.g. tetrahydrofuran, dichloromethane, N,N-dimethylformamide).

Typically, a co-catalyst such as HOBT (1-hydroxy-benzotriazole), HOAT (1-hydroxy-7-azabenzotriazole) and the like may also be present in the reaction mixture. The reaction typically proceeds at room temperature for a time in the range of about 2 hours up to 12 hours.

Compounds of formula (XIV) can be prepared by reaction of compounds of formula (XV)

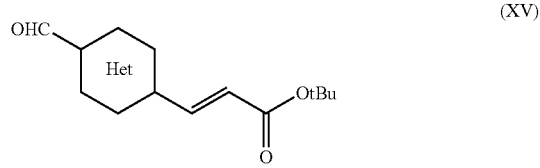

(XV)

with compounds of formula (VII) using the same experimental conditions described above. Deprotection of the tert-butyl ester is carried out according to the known standard procedures.

Compounds of formula (XV) can be prepared by reaction of compounds of formula (XVI)

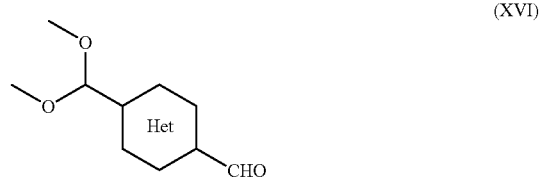

(XVI)

with tert-butyldiethylphosphonoacetate in presence of inorganic base such as sodium hydride in aprotic solvent such as THF. The reaction typically proceeds from 0° C. to room temperature for a time in the range of about 1 hour up to 12 hours. Suitable methods for conversion of the dimethyl acetal into the corresponding aldehyde will be those used conventionally in the art.

Compounds of formula (XVI) can be prepared using the same procedures described for the synthesis of compounds of formula (XI).

The preferred compounds of formula (Ib) can be obtained according to the following synthetic route:

Scheme 2

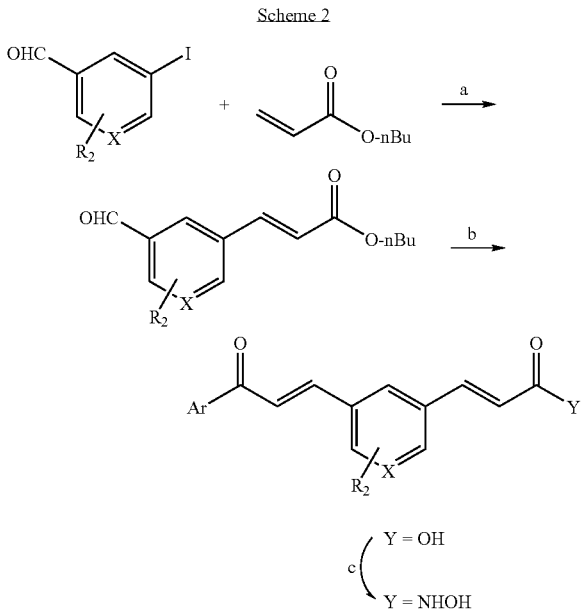

Step a can be performed in presence of potassium phosphate and palladium acetate. Step b can be performed by adding the suitable acetophenone to n-butyl-3-formylcinnamate, in alcoholic basic environment. Step c can be performed by treating the carboxylic acid derivative in scheme 2 with a protected hydroxylamine under standard peptidic coupling conditions known in the art. For compounds of formula (Ic) it is possible to use the following synthetic route:

Scheme 3

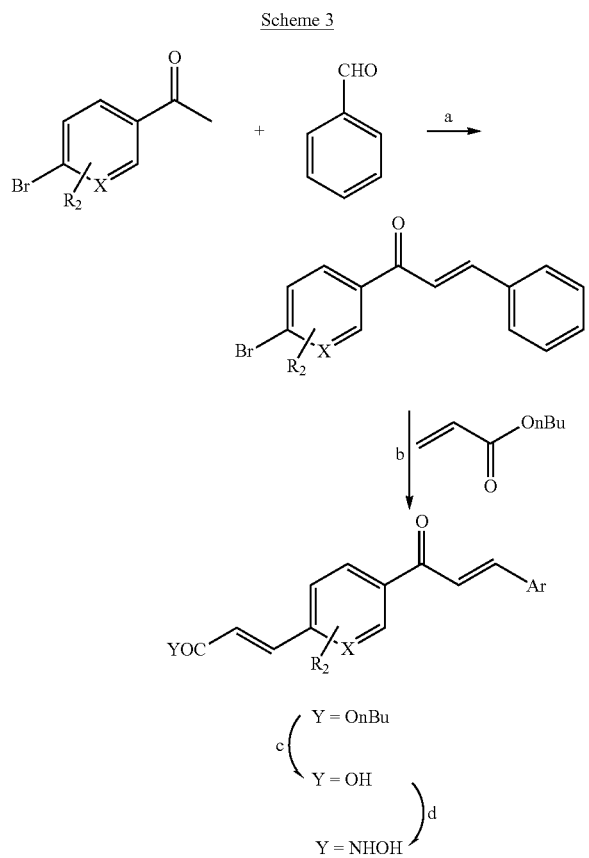

Steps a and c can be performed in alcoholic basic environment. Step b can be performed in presence of potassium phosphate and palladium acetate. Step d can be performed by reaction with ethyl chloroformate and triethylamine, followed by treatment with O-(2-methoxy-2-propyl)hydroxylamine and elution on ion exchange resin.

The compounds of formula (Id) can be obtained by analogue reactions.

Due to the interposition of $R_1$ between the Ar- and cinnamoylamide groups, the compounds of formula (I) are characterised by an extended area of electron conjugation: a special role is played by the central aromatic or heteroaromatic group represented in formula (I) which, due to its intrinsic aromatic character, allows an ideal degree of resonance along the entire longitudinal axis of the molecule, stretching from Ar to the $NHOR_3$ group.

All compounds of formula (I) are endowed with interesting pharmacological properties. In fact they show a high histone deacetylases inhibiting activity, with $IC_{50}$ in the order of 1 μM or lower. Regarding a variety of cell lines, this activity is broad spectrum and is stable throughout the time: both features are ideal from the point of view of the therapeutic application. The compounds of formula (I) also show a powerful activity in promoting apoptosis and inhibiting cell proliferation in a panel of tumor cells, which further supports the antitumor efficacy.

The present invention includes the compounds of said formula (I), for use in therapy, in particular in the treatment of diseases associated to histone deacetylases deregulation.

Further object of the invention are pharmaceutical compositions for treatment and prevention of diseases associated to deregulation of histone deacetylases activity, characterised by containing one or more active principles of formula (I), in association with pharmaceutically acceptable excipients and diluents.

The compounds of the invention have a synergistic action with known antitumor drugs: the aforesaid pharmaceutical compositions can thus include further known antitumor agents and/or any further drug useful for co-administration with antitumor agents (ad. es. immunostimulating compounds, promoters of cell differentiation, etc.).

The compounds of this invention can be administered in conventional manner, e.g. orally, intravenously, subcutaneously, transmucosally (including buccally, sublingually, transurethrally, and rectally), topically, transdermally, by inhalation, or using any other route of administration.

The compounds of formula (I) can be formulated pharmaceutically according to known methods. The pharmaceutical compositions can be chosen in function of the treatment. Said compositions are prepared by suitable mixing of their ingredients and are suitably adapted for oral or parenteral administration; they can be formulated as tablets, capsules, oral preparations, powders, granules, lozenges, regenerable powders, liquid injectable or infusible solutions, suspensions or suppositories.

Tablets and capsules for oral administration are normally presented as unitary dosage form, and may contain conventional excipients such as binders, fillers, diluents, tabletting agents, lubricants, detergents, disintegrants, dyes, flavours and wetting agents. Tablets can be coated according to methods well known in the art.

Suitable fillers include cellulose, mannitol, lactose and further similar agents.

Suitable disintegrants include starch, polyvinylpyrrolidone and starch derivatives such as starch sodium glycolate. Suitable lubricants include, e.g. magnesium stearate. Suitable wetting agents include sodium laurylsulphate.

Solid oral compositions can be prepared by conventional mixing, filling or compression. It is possible to repeat the mixing operations in order to disperse the active agent in compositions containing high amounts of fillers. These operations are conventional.

Liquid oral preparations can be formulated e.g. as aqueous or oily suspensions or solutions, emulsions, syrups or elixir, or can be presented as freeze dried product to be regenerated by addition of water or a suitable vehicle before use. Said liquid preparations can contain conventional additives such as suspending agents, e.g. sorbitol, syrup, methylcellulose, gelatine, hydroxyethylcellulose, carboxymethylcellulose, aluminum stearate gel or hydrogenated edible fats, emulsifying agents, e.g. lecithin, sorbitan monooleate, or acacia; nonaqueous vehicles (which may include edible oils), e.g. almond oil, fractionated coconut oil, oily esters such as glycerin esters, propylene glycol, or ethyl alcohol; preservatives, e.g. methyl or propyl p-hydroxybenzoate or sorbic acid and, if desired, conventional flavours and dyes.

Oral formulations include conventional sustained release forms, such as enteric coated tablets or granules.

For parenteral administration, it is possible to prepare fluid dosage units, containing the compound and a sterile vehicle. The compound, depending on the chosen vehicle and concentration, can be suspended or dissolved. Parenteral solutions are normally prepared by dissolving the compound in a vehicle, sterilizing by filtration, filling suitable vials and sealing. Advantageously it is also possible to dissolve in the vehicle suitable adjuvants such as local anaesthetic, preservatives and buffering agents. In order to increase stability, the composition can be frozen after filling the vial and removing water under vacuum. Parenteral suspensions are prepared substantially in the same way, with the difference that the compound can be suspended rather than dissolved in the vehicle, and they can be sterilised by treatment with ethylene oxide before being suspended in the sterile vehicle. Advantageously, it is possible to include a surfactant or a wetting agent in the composition with the aim of easing the uniform distribution of the compound of the invention.

The compounds of the invention can also be administered topically. Topical formulations may comprise, for example, an ointment, cream, gel, lotion, solution, paste or the like, and/or may be prepared so as to contain liposomes, micelles, and/or microspheres. Ointments, as it is well known in the art of pharmaceutical formulation, are semisolid preparations that are typically based on petrolatum or other petroleum derivatives. Examples of ointments include leaginous ointment bases, for example, vegetable oils, fats obtained from animals, and semisolid hydrocarbons obtained from petroleum, emulsifiable ointment bases, for example, hydroxystearin sulfate, anhydrous lanolin and hydrophilic petrolatum, emulsion ointment bases, for example, cetyl alcohol, glyceryl monostearate, lanolin and stearic acid and water-soluble ointment bases prepared from polyethylene glycols of varying molecular weight. (See, e.g. Remington: The Science and Practice of Pharmacy, Twentieth Ed., Lippincott Williams & Willcins: Philadelphia, 2000) Creams, as also well known to those skilled in the art, are viscous liquids or semisolid emulsions, and contain an oil phase, an emulsifier and an aqueous phase. The oil phase is generally comprised of petrolatum and a fatty alcohol such as cetyl or stearyl alcohol. The aqueous phase usually contains a humectant. The emulsifier in a cream formulation is chosen among non-ionic, anionic, cationic or amphoteric surfactants. Single-phase gels contain organic macromolecules distributed substantially uniformly throughout the carrier liquid, which is typically aqueous, but also, preferably, contain an alcohol and, optionally, an oil. Preferred gelling agents are crosslinked acrylic acid polymers (such as "carbomer" polymers, e.g., carboxypolyalkylenes that may be obtained commercially under the Carbopol trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. For the preparation of uniform gels, dispersing agents such as alcohol or glycerin can be added, or the gelling agent can be dispersed by trituration, mechanical mixing, and/or stirring.

The compounds of the invention may also be administered via transdermal release. Typical transdermal formulations include conventional aqueous and non-aqueous vectors, such as creams, oils, lotions or pastes or can be provided as membranes or medicated plasters. In an embodiment, a compound of the invention is dispersed in a pressure-sensible plaster adhering to the skin. This formulation allows the compound to be spread from the plaster to the patient through the skin. In order to obtain a sustained drug release through the cutis, natural rubber and silicon can be used as pressure-sensitive adhesives.

As it is common practice, the compositions are normally associated with written or printed instructions for use in the relevant treatments.

The invention also includes the use of said compounds of formula (I) in the preparation of a medicament for prevention and/or treatment of diseases associated to deregulation of the activity of histone deacetylases. Examples of such diseases are tumor diseases, Huntington's diseases caused by triplette amplification, degenerative diseases, ischemia, oxidation stress, inflammatory responses of the nervous system, epilepsy, diseases caused by protein aggregates, HIV infections, malaria, leishmanioses, infections caused by protozoa, fungi, phytotoxic agents, virus, parasites, autoimmune diseases, chronic host-directed immune reaction, hypertrophy and cardiac disorders, fibrotic skin disease, muscular spinal or bulbar atrophy, bipolar disorders, psychiatric disorders, X-fragile syndrome, arthritis, renal diseases, psoriasis, intestinal-colitis diseases, beta thalassemia, respiratory diseases, Rubinstein-Taybi syndrome.

Examples of tumors sensible to the present therapy are: leukemias and myeloid and lymphoid lymphomas, acute and chronic myelodisplastic syndromes, multiple myeloma, mammary tumors, lung tumors and pleuric mesoteliomas, cutaneous tumors, including basal carcinomas (basaliomas), melanomas, osteosarcomas, fibrosarcomas, rabdomyosarcomas, neuroblastomas, glioblastomas, cerebral tumors, testicular and ovarian tumors, endometrial and prostatic tumors, thyroid carcinomas, colo-rectal tumors, gastric tumors and gastrointestinal adenocarcinomas, hepatic carcinomas, pancreatic carcinomas, renal tumors, teratocarcinomas and embryo carcinomas.

Further object of the invention is a method for prevention and/or treatment of tumors characterised by administering pharmacologically useful amounts of a compound of formula (I) to a patient in need thereof. Such use and method may include the co-administration, simultaneous or deferred with respect to the administration of the compound of formula (I), of possible further agents with known activity, and any further drug useful for administration in joint therapy with said agents.

The dosage of the compounds of formula (I) is widely variable in function of the patient and his status, the degree of progression of the disease, the chosen way of administration, the chosen number of daily administrations, etc. As a reference they can be administered in a dosage interval comprised between 0.001 and 1000 mg/Kg/day.

The invention is herein described by the following examples having no limiting function.

EXPERIMENTAL PART

1. Chemistry

Methods

Unless otherwise noted, all starting materials were obtained from commercial suppliers and used without further purification.

Specifically, the following abbreviation may be used in the examples and throughout the specification.

| | |
|---|---|
| g (grams) | NMR (Nuclear Magnetic Reasonance) |
| mg (milligrams) | $^1$H (proton) |
| ml (millilitres) | MHz (megahertz) |
| M (molar) | Hz (Hertz) |
| μl (microliters) | LC-MS (Liquid Chromatography Mass Spectrum) |
| mmol (millimoles) | RT (Retention Time, minutes) |
| THF (tetrahydrofuran) | TEA (triethylamine) |
| EtOAc (ethyl acetate) | NaH (sodium hydride) |
| MeOH (methanol) | Na$_2$SO$_4$ (sodium sulphate) |
| EtOH (ethyl alcohol) | K$_2$CO$_3$ (potassium carbonate) |
| DCM (dichloromethane) | Pd(OAc)$_2$ (palladium acetate) |
| DMF (dimethylformamide) | KOH (potassium hydroxide) |
| EDC (1-3(dimethylaminopropyl)-3-ethylcarbodiimide hydrochloride) | HCl (hydrochloric acid) |
| | n-BuLi (n-butyllithium) |
| PPh$_3$ (triphenylphosphine) | DMSO-d$_6$ (deutered dimethylsulfoxide) |
| HOBT (1-hydroxybenzotriazole) | |
| DMA (dimethylacetamide) | |

All references to brine refer to a saturated aqueous solution of NaCl. Unless otherwise indicated, all temperatures are expressed in ° C. (degrees Centigrade). $^1$H-NMR spectra were recorded on a Brucker 300 MHz. Chemical shifts are expressed in parts of million (ppm, δ units). Coupling constants are in units of herts (Hz) Splitting patterns describe apparent multiplicities and are designated as s (singlet), d (doublet), t (triplet), q (quartet), quint (quintet), m (multiplet). b before the various symbols means broad.

Melting points were determined on a Büchi 530 measurer. Infrared spectra (KBr) on a Perkin-Elmer Spectrum One instrument. Mass spectra (MS) were obtained on a JEOL JMS-HX 100 spectrometer.

LCMS were recorded under the following conditions:

METHOD A: Pump 1525, 2777 Sample Manager, PDA 996, Micromass ZQ Single quadrupole (Waters). Column Sunfire C18 (50×2.1 mm, 3.5 μm);
Flow rate: 0.25 ml/min splitting ratio MS:waste/1:4;
Mobile phase: A phase=water/$CH_3CN$ 95/5+0.1% TFA; B phase=water/$CH_3CN$ 5/95+0.1% TFA. 0-1.0 min (A: 98%, B: 2%), 1.0-5.0 min (A: 0%, B: 100%), 5.0-9.0 min (A: 0%, B: 100%), 9.1.0-12 min (A: 98%, B: 2%); UV detection wavelength 254 nm or BPI; Injection volume: 5 μl METHOD B: Pump 1525, 2777 Sample Manager, PDA 996, Micromass ZQ Single quadrupole (Waters). Column Luna C18 (30×2.1 mm, 3 μm);
Flow rate: 0.25 ml/min splitting ratio MS:waste/1:4;
Mobile phase: A phase=water/$CH_3CN$ 95/5+0.1% TFA; B phase=water/$CH_3CN$ 5/95+0.1% TFA. 0-1.0 min (A: 98%, B: 2%), 1.0-5.0 min (A: 0%, B: 100%), 5.0-9.0 min (A: 0%, B: 100%), 9.1.0-12 min (A: 98%, B: 2%); UV detection wavelength 254 nm or BPI; Injection volume: 5 μl METHOD C: Pump 1525, 2777 Sample Manager, PDA 996, Micromass ZQ Single quadrupole (Waters). Column XTerra C18 (50×2.1 mm, 2.5 μm); Flow rate: 0.25 ml/min splitting ratio MS:waste/1:4;
Mobile phase: A phase=water/$CH_3CN$ 95/5+0.1% TFA; B phase=water/$CH_3CN$ 5/95+0.1% TFA. 0-1.0 min (A: 98%, B: 2%), 1.0-5.0 min (A: 0%, B: 100%), 5.0-9.0 min (A: 0%, B: 100%), 9.1.0-12 min (A: 98%, B: 2%); UV detection wavelength 254 nm or BPI; Injection volume: 5 μl METHOD D: Pump 1525, 2777 Sample Manager, PDA 996, Micromass ZQ Single quadrupole (Waters). Column Atlantis dC18 (100×2.1 mm, 3 μm); Flow rate: 0.25 ml/min splitting ratio MS:waste/1:4;
Mobile phase: A phase=water/$CH_3CN$ 95/5+0.1% TFA; B phase=water/$CH_3CN$ 5/95+0.1% TFA. 0-1.0 min (A: 98%, B: 2%), 1.0-5.0 min (A: 0%, B: 100%), 5.0-9.0 min (A: 0%, B: 100%), 9.1.0-12 min (A: 98%, B: 2%); UV detection wavelength 254 nm or BPI; Injection volume: 5 μl METHOD E: Pump 1525, 2777 Sample Manager, PDA 996, Micromass ZQ Single quadrupole (Waters). Column Disc. HS F5 C18 (50×2.1 mm, 3 μm); Flow rate: 0.25 ml/min splitting ratio MS:waste/1:4;
Mobile phase: A phase=water/$CH_3CN$ 95/5+0.1% TFA; B phase=water/$CH_3CN$ 5/95+0.1% TFA. 0-1.0 min (A: 98%, B: 2%), 1.0-5.0 min (A: 0%, B: 100%), 5.0-9.0 min (A: 0%, B: 100%), 9.1.0-12 min (A: 98%, B: 2%); UV detection wavelength 254 nm or BPI; Injection volume: 5 μl METHOD F: Pump 1525, 2777 Sample Manager, PDA 996, Micromass ZQ Single quadrupole (Waters). SunFire C18 (50×2.1 mm, 3.5 μm); Flow rate: 0.25 ml/min splitting ratio MS:waste/1:4;
Mobile phase: A phase=$HCOO^-NH_4^+$ pH=8/MeOH/$CH_3CN$ 85/10//5; B phase=$HCOO^-NH_4^+$ pH=8/MeOH/$CH_3CN$ 5/10/85. 0-1.0 min (A: 98%, B: 2%), 1.0-5.0 min (A: 0%, B: 100%), 5.0-9.0 min (A: 0%, B: 100%), 9.1.0-12 min (A: 98%, B: 2%); UV detection wavelength 254 nm or BPI; Injection volume: 5 μl All mass spectra were taken under electrospray ionisation (ESI) methods.

Most of the reactions were monitored by thin-layer chromatography on 0.2 mm Merck silica gel plates (60F-254), visualized with UV light. Flash column chromatography was performed on silica gel 60 (0.04-0.063 mm) Merck.

Synthesis of ethyl 4-formylcinnamate

The synthesis was performed according to Saigo et al., *Bull. Chem. Soc. Jpn.,* 1995, 68, 2355-2362.

Synthesis of n-butyl 3-formylcinnamate

A 10 mL Schenk tube was dried in oven and loaded under $N_2$ with $K_3PO_4$ (2.37 g, 11.16 mmol) and DMA (2.0 mL). 3-iodobenzaldeide (1.85 g, 7.97 mmol) and n-butylacrylate (2.28 mL, 15.94 mmol) were then added by syringe. A solution of $Pd(OAc)_2$ (0.18 g, 0.797 mmol) in DMA (0.5 mL) was further added by syringe. The Schlenk tube was then sealed under nitrogen and placed in a pre-heated oil bath at 140° C., and the reaction mixture was stirred for 24 h. After cooling to room temperature, the reaction mixture was poured in water (50 mL) and extracted with ethyl acetate (3×50 mL). The combined organic extracts were washed with brine, dried ($Na_2SO_4$), and concentrated under vacuum to dryness. The crude product was purified by chromatographic column on silica gel, eluting with n-hexane/ethylacetate/methanol 12/3/1 (yield: 47%). $^1$H NMR ($CDCl_3$) δ: 0.91-0.96 (t, 3H, $OCH_2CH_2CH_2CH_3$), 1.39-1.42 (m, 2H, $OCH_2CH_2CH_2CH_3$), 1.65-1.68 (m, 2H, $OCH_2CH_2CH_2CH_3$), 4.17-4.21 (m, 2H, $OCH_2CH_2CH_2CH_3$), 6.48-6.53 (d, 1H, ArCH=CHCO), 7.52-7.54 (m, 1H, benzene H-5), 7.53-7.75 (m, 2H, ArCH=CHCO and benzene H-6), 7.84-7.86 (m, 1H, benzene H-4), 7.99 (m, 1H, benzene H-2), 10.01 (s, 1H, CHO).

n-butyl 4-cinnamoylcinnamate shown in Scheme 3 was prepared using a similar procedure.

General Procedure for the Synthesis of 3- and 4-Substituted Cinnamic Acids

Example

Synthesis of 3-[3-[3-(3-fluorophenyl)-3-oxopropen-1-il]benzenepropenoic acid

A mixture of n-butyl-4-formylcinnamate (6.0 mmol, 1.40 g), 3-fluoroacetophenone (6.0 mmol, 0.93 g), and KOH 2 N (24.0 mmol, 12.4 mL) in ethanol (15 mL)/water (15 mL) was stirred at room temperature for 24 h. Thereafter, the solution was poured in water (100 mL) and acidified with HCl 2N. The precipitate thus obtained was filtered and recrystallised obtaining the pure acid. Yield: 72%; mp: 157-159° C., recrystallisation solvent: acetonitrile. $^1$H NMR (DMSO-$d_6$) δ 6.69-6.73 (d, 1H, CH=CHCOOH), 7.48-7.54 (m, 2H, benzene H), 7.61-7.65 (m, 2H, benzene H and COCH=CH), 7.74-7.80 (m, 2H, benzene H and COCH=CH), 7.88-7.90 (m, 1H, benzene H), 8.02-8.06 (m, 3H, benzene H and CH=CHCOOH), 8.31 (s, 1H, benzene H), 12.50 (bs, 1H, OH).

4-bromophenyl-2-phenylvinylketone shown in Scheme 3 was prepared using a similar procedure.

General Procedure for the Synthesis of 3- and 4-Substituted N-hydroxycinnamic amides Example Synthesis of N-hydroxy-3-[3-[3-(3-fluorophenyl)-3-oxopropen-1-yl]benzenepropenamide A cooled solution (0° C.) of 3-[3-[3-(3-fluorophenyl)-3-oxopropen-1-il]benzenepropenoic acid (4.2 mmol, 1.2 g) in dried THF (10 mL), was added to ethyl chloroformate (5.0 mmol, 0.5 mL) and triethylamine (5.4 mmol, 0.8 mL), and the mixture was stirred for 10 min. The reaction mixture was filtered, and the filtrate was added to O-(2-methoxy-2-propyl)

hydroxylamine (4.71 mmol, 0.35 mL) (*Tetrahedron* 1988, 44, 6013-20). The solution was stirred for 15 min at 0° C., then evaporated under reduced pressure, and the residue was diluted in methanol (10 mL). The solution of the O-protected hydroxamate was added to an Amberlyst® 15 ion exchange resin (0.3 g), and the resulting mixture was stirred at 45° C. for 1 h.

Thereafter, the reaction mixture was filtered and the filtrate was concentrated under vacuum obtaining the crude N-hydroxyamide, which was then purified by crystallisation. Yield: 74%; mp: 166-168° C., recrystallisation solvent: acetonitrile. $^1$H NMR (DMSO-d$_6$) δ 6.54-6.58 (d, 1H, CH═CHCOOH), 7.48-7.56 (m, 3H, benzene H), 7.62-7.66 (m, 2H, benzene H), 7.76-7.80 (m, 1H, COCH═CH), 7.87-7.89 (m, 1H, benzene H), 7.96-8.03 (m, 3H, benzene H, COCH═CH and CH═CHCOOH), 8.15 (s, 1H, benzene H), 9.07 (s, 1H, NH), 10.80 (s, 1H, OH).

By following the aforementioned general procedures, a number of compounds were synthesised, whose structures and synthesis data are reported in table 1.

TABLE 1

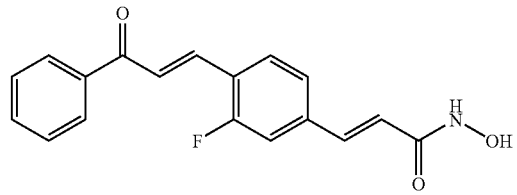

| Compound | Ar | Yield (%) | χ | Mp ° C. |
|---|---|---|---|---|
| MC1632 | Ph | 62 | C6H6/CH3CN | 180-181 |
| MC1645 | 2-Cl-Ph | 53 | CH3CN | 158-160 |
| MC1622 | 3-Cl-Ph | 60 | MeOH | 205-206 |
| MC1624 | 2-F-Ph | 51 | C6H6/CH3CN | 155-156 |
| MC1610 | 3-F-Ph | 67 | C6H12/C6H6 | 175-176 |
| MC1625 | 4-F-Ph | 74 | MeOH | 208-209 |
| MC1644 | 2-Me-Ph | 48 | CH3CN | 140-142 |
| MC1623 | 3-Me-Ph | 56 | MeOH | 210-212 |
| MC1639 | 4-Me-Ph | 65 | MeOH | 226-228 |
| MC1652 | 1-naphthyl | 65 | CH3CN | 134-136 |
| MC1671 | 5-dihydro-benzofuran | 76 | CH3CN | 179-181 dec. |

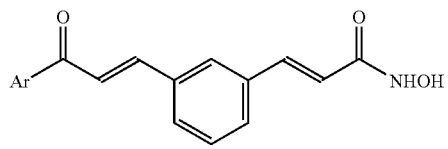

| Compound | Ar | Yield (%) | χ | Mp ° C. |
|---|---|---|---|---|
| MC1646 | Ph | 64 | C$_6$H$_6$/CH$_3$CN | 108-110 |
| MC1670 | 2-Cl-Ph | 61 | CH$_2$Cl$_2$/petr. ether | 104-106 |
| MC1672 | 3-Cl-Ph | 68 | THF/petr. ether | 177-179 |
| MC1661 | 2-F-Ph | 58 | C$_6$H$_{12}$/C$_6$H$_6$ | 98-100 |
| MC1653 | 3-F-Ph | 74 | CH$_3$CN | 166-168 |

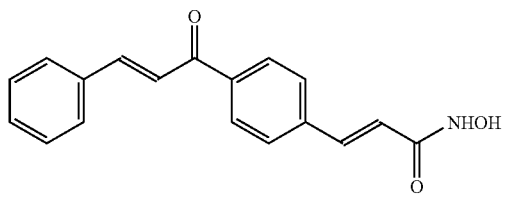

| Compound | Yield (%) | χ | Mp ° C. |
|---|---|---|---|
| MC1631 | 57 | C$_6$H$_6$/CH$_3$CN | 147-149 |

Example 1

3-[3-Fluoro-4-(3-oxo-3-phenyl-propenyl)-phenyl]-N-hydroxy-acrylamide

Step A

A solution of 4-bromo-2-fluoro benzaldehyde (2 g, 9.9 mmol) in DMF (50 ml) and triethylamine (6 ml) was degassed flushing N$_2$ for 30 min. PPh$_3$ (130 mg, 0.459 mmol), Pd(OAc)$_2$ (44.3 mg, 0.20 mmol), NaHCO$_3$ (1.6 g, 18.6 mmol) and tert-butyl acrylate (1.27 g, 9.9 mmol) were added and the resulting mixture was heated to reflux for 4 h. Additional tert-butyl acrylate (633 mg) and Pd(OAc)$_2$ (20 mg) were added and the mixture was stirred at 100° C. for 3 h then the solution was diluted with H$_2$O and extracted with Et$_2$O. The organic layer was dried over Na$_2$SO$_4$ and the solvent was evaporated under vacuo to give the crude product that was purified by silica gel chromatography (petroleum ether/ EtOAc 95:5). The collected fractions gave 2 g of 3-(3-fluoro-4-formyl-phenyl)-acrylic acid tert-butyl ester.

Yield: 80%

Step B 3-(3-fluoro-4-formyl-phenyl)-acrylic acid tert-butyl ester (2 g, 8 mmol) was dissolved in DCM (23 ml) and trifluoroacetic acid (6 ml). The mixture was stirred at room temperature for 6 h then the solvent was evaporated under vacuo giving 1.62 g of 3-(3-fluoro-4-formyl-phenyl)-acrylic acid Yield: quantitative Step C 3-(3-fluoro-4-formyl-phenyl)-acrylic acid (500 mg, 2.57 mmol) was dissolved in ethanol/water (1:1, 10 ml) and 1.7M KOH (3 ml). To the resulting solution was added acetophenone (0.3 ml, 2.57 mmol). The mixture was stirred at room temperature overnight then acidified with 10% HCl and extracted with EtOAc. The organic layer was dried over Na$_2$SO$_4$ and the solvent was evaporated under vacuo. The crude product was triturated in EtOAc and filtered to give 560 mg of 3-[3-fluoro-4-(3-oxo-3-phenyl-propenyl)-phenyl]-acrylic acid.

Yield: 73%

Step D

3-[3-fluoro-4-(3-oxo-3-phenyl-propenyl)-phenyl]-acrylic acid (450 mg, 1.52 mmol) was dissolved in THF (10 ml) and DMF (1 ml). To the resulting solution, HOBT (413 mg, 3.04 mmol), EDC (580 mg, 3.04 mmol), TEA (0.423 ml, 3.04 mmol) and NH$_2$OTHP (213 mg, 1.82 mmol) were added. The mixture was stirred overnight at RT then partitioned between water and EtOAc. The organic extract was washed with water then dried over Na$_2$SO$_4$ and evaporated under vacuo.

The crude product was purified by silica gel chromatography (petroleum ether/EtOAc 1:1) and the resulting oil was dissolved in DCM and treated with HCl/Et$_2$O for 1 h. The precipitate was filtered on Buckner funnel and washed with DCM/MeOH to give 200 mg of 3-[3-fluoro-4-(3-oxo-3-phenyl-propenyl)-phenyl]-N-hydroxy-acrylamide.

LC-MS Method=B RT=6.01; (ES+) gave MH$^+$: 312.2

$^1$H-NMR (DMSO-d$_6$,): 10.84 (s br, 1H); 9.07 (s br, 1H); 8.15 (m, 3H); 8.00 (d, 1H); 7.81 (d, 1H); 7.69 (ddd, 1H); 7.63-7.52 (m, 4H); 7.48 (d, 1H); 6.60 (d, 1H).

The compounds in Table 2 were prepared according to the procedure described above (steps A-D or C-D when the intermediate was commercially available).

TABLE 2

| Ex no | structure | Compound name | LC-MS method; RT min | MH+ | $^1$H-NMR (DMSO-d$_6$) δ: |
|---|---|---|---|---|---|
| 2 | 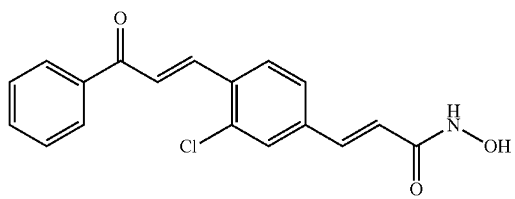 | 3-[3-chloro-4-(3-oxo-3-phenyl-propenyl)-phenyl]-N-hydroxy-acrylamide | B, 6.33 | 328.1 | 8.26 (d, 1H); 8.17 (d, 2H); 8.02 (s, 2H); 7.78 (s, 1H); 7.73-7.55 (m, 4H); 7.47 (d, 1H); 6.63 (d, 1H) |
| 3 | 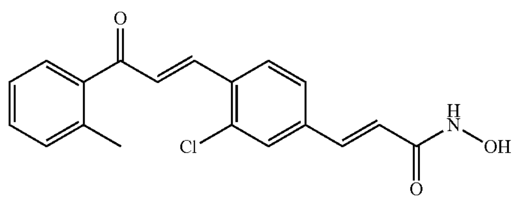 | 3-[3-chloro-4-(3-oxo-3-o-tolyl-propenyl)-phenyl]-N-hydroxy-acrylamide | A, 6.92 | 342.0 | 8.13 (d, 1H); 7.77 (d, 1H); 7.77-7.67 (m, 2H); 7.61 (d, 1H); 7.51 (d, 1H); 7.50-7.41 (m, 2H); 7.36 (m, 2H); 6.62 (d, 1H); 2.41 (s, 3H) |
| 4 | 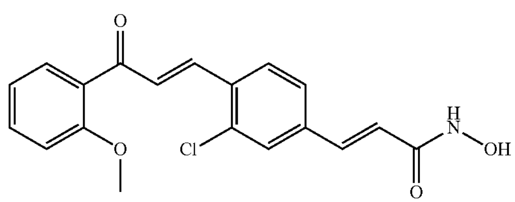 | 3-{3-chloro-4-[3-(2-methoxy-phenyl)-3-oxo-propenyl]-phenyl}-N-hydroxy-acrylamide | A, 6.72 | 358.0 | 8.01 (d, 1H); 7.76 (s, 1H); 7.63-7.49 (m, 4H); 7.45 (d, 1H); 7.21 (d, 1H); 7.08 (dd, 1H); 6.61 (d, 1H); 3.88 (s, 3H) |
| 5 | 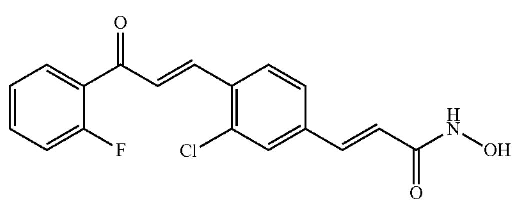 | 3-{3-chloro-4-[3-(2-fluoro-phenyl)-3-oxo-propenyl]-phenyl}-N-hydroxy-acrylamide | B, 6.30 | 346.2 | 10.75 (s br, 1H); 9.13 (s br, 1H); 8.04 (d, 1H); 7.90 (d, 1H); 7.83 (ddd, 1H); 7.78 (s, 1H); 7.74-7.65 (m, 1H); 7.63 (d, 1H); 7.58 (dd, 1H); 7.46 (d, 1H); 7.41 (dd, 1H); 7.38 (d, 1H); 6.60 (d, 1H). |

TABLE 2-continued

| Ex no | structure | Compound name | LC-MS method; RT min | MH+ | 1H-NMR (DMSO-d6) δ: |
|---|---|---|---|---|---|
| 6 | 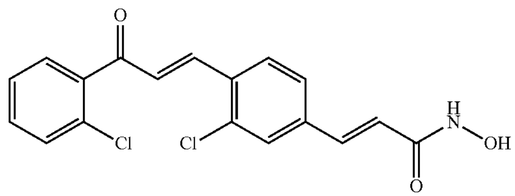 | 3-{3-chloro-4-[3-(2-chloro-phenyl)-3-oxo-propenyl]-phenyl}-N-hydroxy-acrylamide | A, 6.89 | 362.0 | 8.09 (d, 1H); 7.76 (s br, 1H); 7.70 (d, 1H); 7.67-7.47 (m, 5H); 7.45 (d, 1H); 7.39 (d, 1H); 6.62 (d, 1H) |
| 7 | 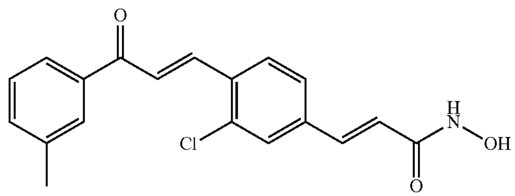 | 3-[3-chloro-4-(3-oxo-3-m-tolyl-propenyl)-phenyl]-N-hydroxy-acrylamide | B, 6.54 | 342.2 | 10.74 (s br, 1H); 9.08 (s br, 1H); 8.26 (d, 1H); 8.02 (s, 2H); 7.97 (m, 2H); 7.79 (s, 1H); 7.75 (d, 1H); 7.54-7.41 (m, 3H); 6.62 (d, 1H); 2.43 (s, 3H) |
| 8 | 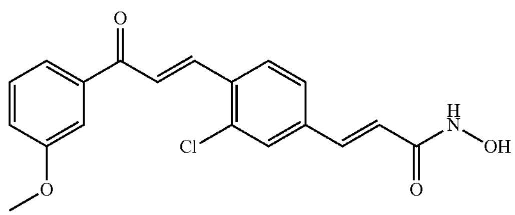 | 3-{3-chloro-4-[3-(3-methoxy-phenyl)-3-oxo-propenyl]-phenyl}-N-hydroxy-acrylamide | A, 7.01 | 358.0 | 8.28 (d, 1H); 8.03 and 7.98 (ABq, 2H); 7.78 (m, 2H); 7.64 (m, 1H); 7.51 (dd, 1H); 7.47 (d, 1H); 7.26 (ddd, 1H); 6.62 (d, 1H); 3.86 (s, 3H) |
| 9 | 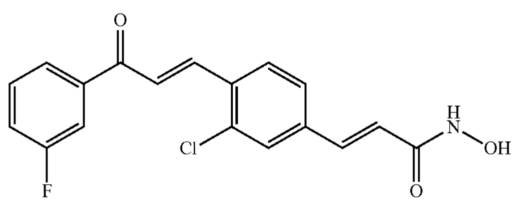 | 3-{3-chloro-4-[3-(3-fluoro-phenyl)-3-oxo-propenyl]-phenyl}-N-hydroxy-acrylamide | B, 6.49 | 346.1 | 10.80 (s br, 1H); 9.08 (s br, 1H); 8.30 (d, 1H); 8.05 (s, 2H); 8.02 (dd, 1H); 7.99 (ddd, 1H); 7.79 (s, 1H); 7.70-7.61 (m, 2H); 7.55 (ddd, 1H); 7.48 (d, 1H); 6.63 (d, 1H) |

TABLE 2-continued

| Ex no | structure | Compound name | LC-MS method; RT min | MH+ | 1H-NMR (DMSO-d6) δ: |
|---|---|---|---|---|---|
| 10 | 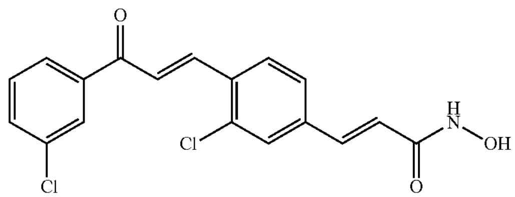 | 3-{3-chloro-4-[3-(3-chloro-phenyl)-3-oxo-propenyl]-phenyl}-N-hydroxy-acrylamide | A, 7.33 | 362.0 | 10.78 (s br, 1H); 9.23 (s br, 1H); 8.31 (d, 1H); 8.22 (dd, 1H); 8.13 (ddd, 1H); 8.05 (s, 2H); 7.79 (d, 1H); 7.76 (ddd, 1H); 7.66 (m, 1H); 7.63 (dd, 1H); 7.47 (d, 1H); 6.63 (d, 1H) |
| 11 | 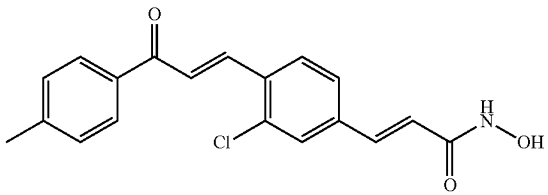 | 3-[3-Chloro-4-(3-oxo-3-p-tolyl-propenyl)-phenyl]-N-hydroxy-acrylamide | A, 7.12 | 342.0 | 8.26 (d, 1H); 8.09 (d, 2H); 8.01 (s, 2H); 7.78 (s, 1H); 7.64 (d, 1H); 7.47 (d, 1H); 7.40 (d, 2H); 6.63 (d, 1H); 2.42 (s, 3H) |
| 12 | 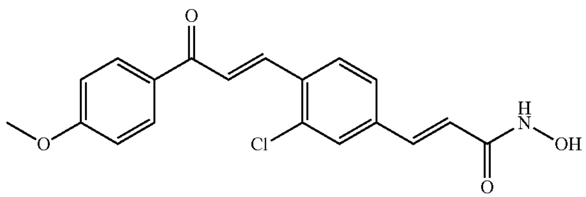 | 3-{3-chloro-4-[3-(4-methoxy-phenyl)-3-oxo-propenyl]-phenyl}-N-hydroxy-acrylamide | B, 6.28 | 358.1 | 10.78 (s br, 1H); 9.08 (s br, 1H); 8.25 (d, 1H); 8.19 (d, 2H); 8.03 and 7.99 (ABq, 2H); 7.77 (s, 1H); 7.64 (d, 1H); 7.47 (d, 1H); 7.10 (d, 2H); 6.61 (d, 1H); 3.88 (s, 3H) |
| 13 | 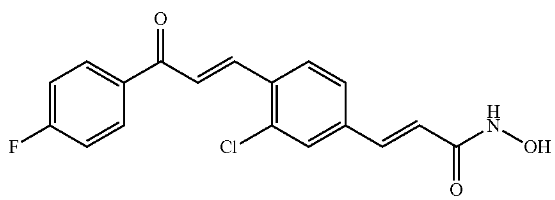 | 3-{3-chloro-4-[3-(4-fluoro-phenyl)-3-oxo-propenyl]-phenyl}-N-hydroxy-acrylamide | A, 7.01 | 346.1 | 8.28 (dd, 2H); 8.26 (d, 1H); 8.03 (s, 2H); 7.78 (s, 1H); 7.64 (d, 1H); 7.46 (d, 1H); 7.41 (dd, 2H); 6.65 (d, 1H) |
| 14 | 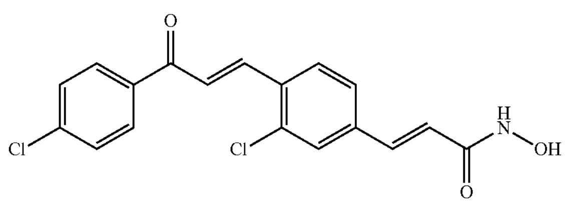 | 3-{3-chloro-4-[3-(4-chloro-phenyl)-3-oxo-propenyl]-phenyl}-N-hydroxy-acrylamide | A, 7.33 | 362.0 | 8.27 (d, 1H); 8.20 (d, 2H); 8.03 (s, 2H); 7.77 (s, 1H); 7.65 (d, 2H); 7.65 (d, 1H); 7.46 (d, 1H); 6.65 (d, 1H) |

TABLE 2-continued

| Ex no | structure | Compound name | LC-MS method; RT min | MH+ | 1H-NMR (DMSO-d6) δ: |
|---|---|---|---|---|---|
| 15 | 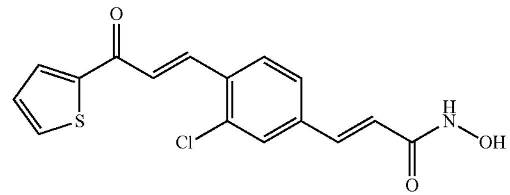 | 3-[3-chloro-4-(3-oxo-3-thiophen-2-yl-propenyl)-phenyl]-N-hydroxy-acrylamide | B, 6.28 | 334.1 | 10.73 (s br, 1H); 8.36 (dd, 1H); 8.25 (d, 1H); 8.10 (dd, 1H); 8.01 (d, 1H); 7.96 (d, 1H); 7.79 (d, 1H); 7.66 (dd, 1H); 7.47 (d, 1H); 7.34 (dd, 1H); 6.23 (d, 1H) |
| 16 | 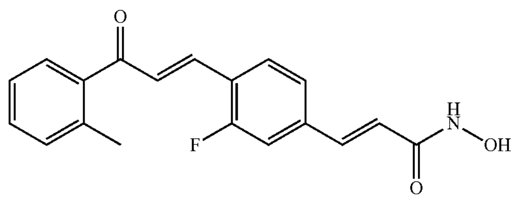 | 3-[3-fluoro-4-(3-oxo-3-o-tolyl-propenyl)-phenyl]-N-hydroxy-acrylamide | A, 6.81 | 326.1 | 8.02 (dd, 1H); 7.66 (dd, 1H); 7.59-7.42 (m, 6H); 7.36 (m, 2H); 6.60 (d, 1H); 2.40 (s, 3H) |
| 17 | 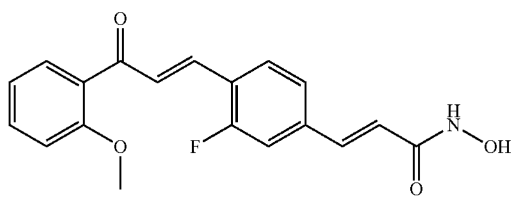 | 3-[3-fluoro-4-[3-(2-methoxy-phenyl)-3-oxo-propenyl]-phenyl]-N-hydroxy-acrylamide | F, 6.55 | 342.1 | 8.91 (dd, 1H); 7.61-7.42 (m, 7H); 7.21 (d, 1H); 7.07 (ddd, 1H); 6.58 (d, 1H); 3.88 (s, 3H) |
| 18 | 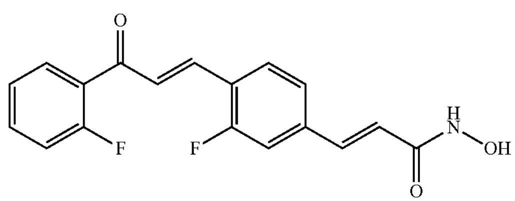 | 3-[3-fluoro-4-[3-(2-fluoro-phenyl)-3-oxo-propenyl]-phenyl]-N-hydroxy-acrylamide | A, 6.82 | 330.0 | 7.98 (dd, 1H); 7.82 (ddd, 1H); 7.74-7.64 (m, 2H); 7.62-7.47 (m, 4H); 7.46-7.35 (m, 2H); 6.61 (d, 1H) |
| 19 | 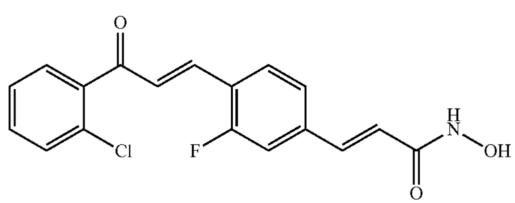 | 3-{4-[3-(2-chloro-phenyl)-3-oxo-propenyl]-3-fluoro-phenyl}-N-hydroxy-acrylamide | C, 5.99 | 345.9 | 7.98 (dd, 1H); 7.64-7.34 (m, 9H); 6.61 (d, 1H) |

TABLE 2-continued

| Ex no | structure | Compound name | LC-MS method; RT min | MH+ | 1H-NMR (DMSO-d6) δ: |
|---|---|---|---|---|---|
| 20 | 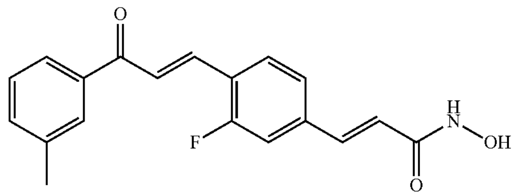 | 3-[3-fluoro-4-(3-oxo-3-m-tolyl-propenyl)-phenyl]-N-hydroxy-acrylamide | A, 6.97 | 326.1 | 8.16 (dd, 1H); 7.99 (d, 1H); 7.94 (m, 2H); 7.80 (d, 1H); 7.59-7.43 (m, 5H); 6.61 (d, 1H); 2.43 (s, 3H) |
| 21 | 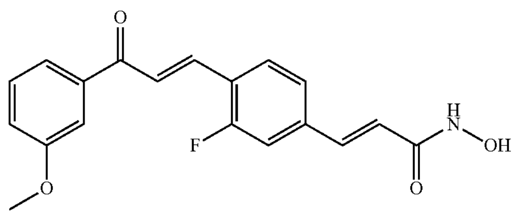 | 3-{3-fluoro-4-[3-(3-methoxy-phenyl)-3-oxo-propenyl]-phenyl}-N-hydroxy-acrylamide | A, 6.70 | 342.1 | 8.17 (dd, 1H); 7.98 (d, 1H); 7.81 (d, 1H); 7.76 (ddd, 1H); 7.61 (dd, 1H); 7.58-7.43 (m, 4H); 7.26 (ddd, 1H); 6.62 (d, 1H); 3.86 (s, 3H) |
| 22 | 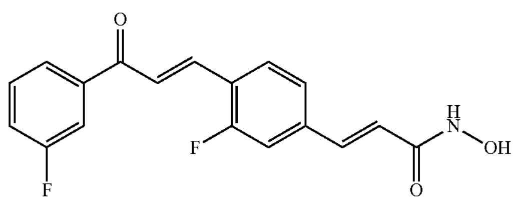 | 3-{3-fluoro-4-[3-(3-fluoro-phenyl)-3-oxo-propenyl]-phenyl}-N-hydroxy-acrylamide | B, 7.38 | 330.2 | 8.19 (dd, 1H); 8.01 (d, 1H); 8.00 (d, 1H); 7.95 (ddd, 1H); 7.84 (d, 1H); 7.70-7.51 (m, 4H); 7.49 (d, 1H); 6.62 (d, 1H) |
| 23 | 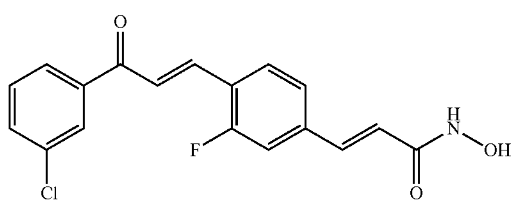 | 3-{4-[3-(3-chloro-phenyl)-3-oxo-propenyl]-3-fluoro-phenyl}-N-hydroxy-acrylamide | A, 7.17 | 346.0 | 8.20 (dd, 1H); 8.18 (m, 1H); 8.10 (ddd, 1H); 8.01 (d, 1H); 7.84 (d, 1H); 7.76 (ddd, 1H); 7.62 (dd, 1H); 7.54 (m, 2H); 7.48 (d, 1H); 6.63 (d, 1H) |

TABLE 2-continued

| Ex no | structure | Compound name | LC-MS method; RT min | MH+ | ¹H-NMR (DMSO-d₆) δ: |
|---|---|---|---|---|---|
| 24 | 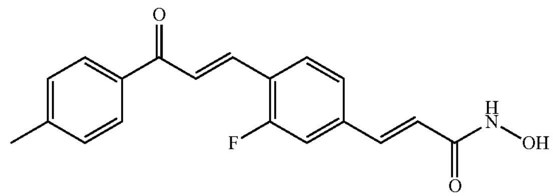 | 3-[3-fluoro-4-(3-oxo-3-p-tolyl-propenyl)-phenyl]-N-hydroxy-acrylamide | B, 6.43 | 326.1 | 10.82 (s br, 1H); 9.18 (s br, 1H); 8.15 (dd, 1H); 8.06 (d, 2H); 8.00 (d, 1H); 7.79 (d, 1H); 7.54 (m, 2H); 7.48 (d, 1H); 7.40 (d, 2H); 6.59 (d, 1H); 2.42 (s, 3H) |
| 25 | 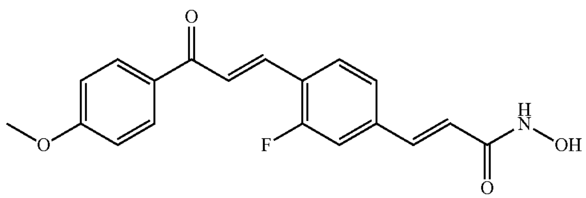 | 3-{3-fluoro-4-[3-(4-methoxy-phenyl)-3-oxo-propenyl]-phenyl}-N-hydroxy-acrylamide | A, 6.60 | 342.1 | 8.16 (d, 2H); 8.15 (dd, 1H); 8.01 (d, 1H); 7.78 (d, 1H); 7.53 (m, 2H); 7.47 (d, 1H); 7.10 (d, 2H); 6.61 (d, 1H); 3.88 (s, 3H) |
| 26 | 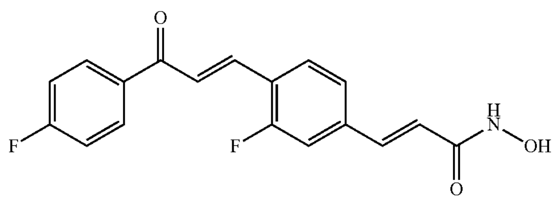 | 3-{3-fluoro-4-[3-(4-fluoro-phenyl)-3-oxo-propenyl]-phenyl}-N-hydroxy-acrylamide | A, 6.78 | 330.1 | 8.25 (dd, 2H); 8.16 (dd, 1H); 8.01 (d, 1H); 7.81 (d, 1H); 7.53 (m, 2H); 7.43 (m, 1H); 7.41 (dd, 2H); 6.62 (d, 1H) |
| 27 | 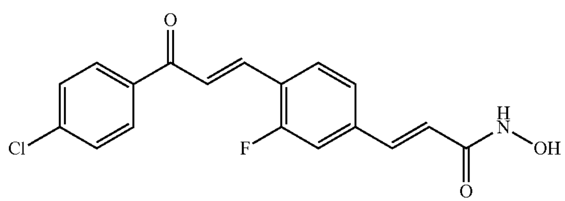 | 3-{4-[3-(4-chloro-phenyl)-3-oxo-propenyl]-3-fluoro-phenyl}-N-hydroxy-acrylamide | A, 7.15 | 346.0 | 8.18 (d, 2H); 8.16 (dd, 1H); 8.01 (d, 1H); 7.82 (d, 1H); 7.66 (d, 2H); 7.54 (m, 2H); 7.48 (d, 1H); 6.62 (d, 1H) |
| 28 | 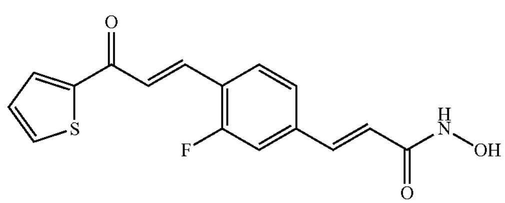 | 3-[3-fluoro-4-(3-oxo-3-thiophen-2-yl-propenyl)-phenyl]-N-hydroxy-acrylamide | B, 6.14 | 318.1 | 10.85 (s br, 1H); 8.32 (dd, 1H); 8.15 (dd, 1H); 8.09 (dd, 1H); 7.94 (d, 1H); 7.79 (d, 1H); 7.53 (m, 2H); 7.48 (d, 1H); 7.33 (dd, 1H); 6.65 (d, 1H) |

TABLE 2-continued

| Ex no | structure | Compound name | LC-MS method; RT min | MH+ | 1H-NMR (DMSO-d6) δ: |
|---|---|---|---|---|---|
| 29 | 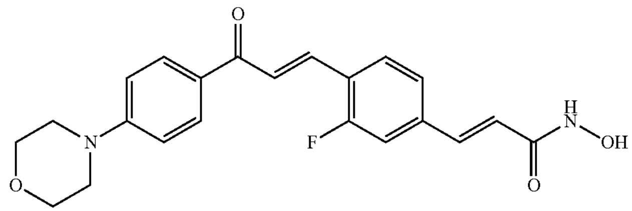 | 3-{3-fluoro-4-[3-(4-morpholin-4-yl-phenyl)-3-oxo-propenyl]-phenyl}-N-hydroxy-acrylamide | B, 6.09 | 397.1 | 10.79 (s br, 1H); 8.14 (dd, 1H); 8.06 (d, 2H); 7.98 (d, 1H); 7.75 (d, 1H); 7.59-7.39 (m, 3H); 7.04 (d, 2H); 6.59 (d, 1H); 3.75 (m, 4H); 3.40 (m, 4H) |
| 30 | 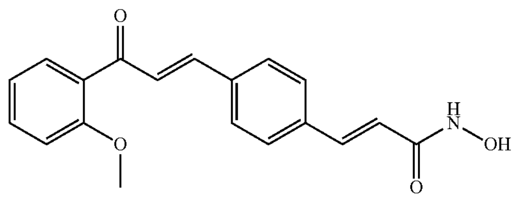 | N-hydroxy-3-{4-[3-(2-methoxy-phenyl)-3-oxo-propenyl]-phenyl}-acrylamide | B, 6.08 | 324.1 | 7.76 (d, 2H); 7.61 (d, 2H); 7.59-7.40 (m, 5H); 7.20 (d, 1H); 7.06 (ddd, 1H); 6.55 (d, 1H); 3.87 (s, 3H) |
| 31 | 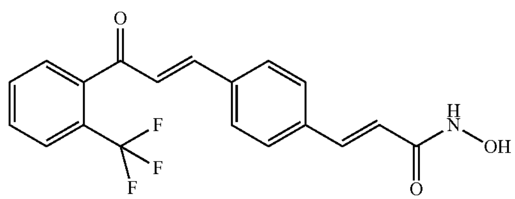 | N-hydroxy-3-{4-[3-oxo-3-(2-trifluoromethyl-phenyl)-propenyl]-phenyl}-acrylamide | E, 6.53 | 361.8 | 7.89 (d, 1H); 7.82 (dd, 1H); 7.79 (d, 2H); 7.76 (dd, 1H); 7.68 (d, 1H); 7.61 (dd, 2H); 7.46 (d, 1H); 7.35 (d, 1H); 7.30 (d, 1H); 6.56 (d, 1H) |
| 32 | 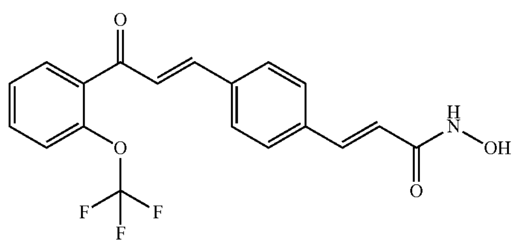 | N-hydroxy-3-{4-[3-oxo-3-(2-trifluoromethoxy-phenyl)-propenyl]-phenyl}-acrylamide | A, 6.65 | 377.8 | 7.81 (d, 2H); 7.78 (dd, 1H); 7.73 (ddd, 1H); 7.62 (d, 2H); 7.60-7.50 (m, 3H); 7.47 (d, 1H); 7.39 (d, 1H); 6.57 (d, 1H) |

TABLE 2-continued

| Ex no | structure | Compound name | LC-MS method; RT min | MH+ | 1H-NMR (DMSO-d6) δ: |
|---|---|---|---|---|---|
| 33 | 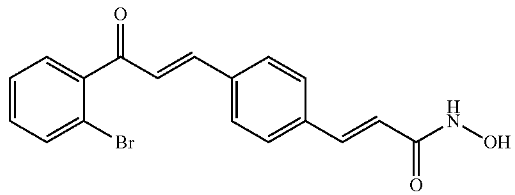 | 3-{4-[3-(2-bromo-phenyl)-3-oxo-propenyl]-phenyl}-N-hydroxy-acrylamide | D, 7.42 | 371.7 | 7.80 (d, 2H); 7.76 (d, 1H); 7.62 (d, 2H); 7.57-7.42 (m, 4H); 7.38 (d, 1H); 7.28 (d, 1H); 6.56 (d, 1H) |
| 34 | 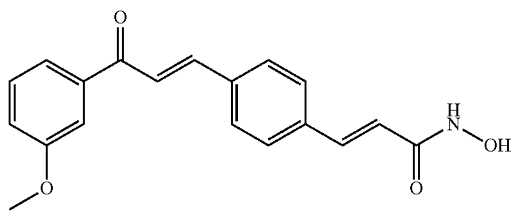 | N-hydroxy-3-{4-[3-(3-methoxy-phenyl)-3-oxo-propenyl]-phenyl}-acrylamide | A, 6.41 | 324.0 | 11.59 (s br, 1H); 10.76 (s br, 1H); 7.95 (d, 1H); 7.94 (d, 1H); 7.92 (s, 1H); 7.77 (ddd, 1H); 7.74 (d, 1H); 7.68-7.58 (m, 3H); 7.50 (dd, 1H); 7.49 (d, 1H); 7.25 (ddd, 1H); 6.56 (d, 1H); 3.86 (s, 3H) |
| 35 | 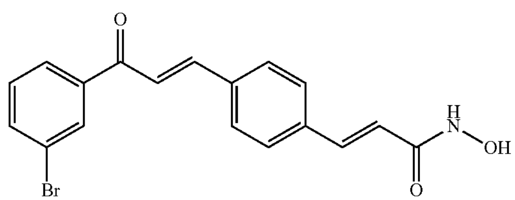 | 3-{4-[3-(3-bromo-phenyl)-3-oxo-propenyl]-phenyl}-N-hydroxy-acrylamide | A, 6.85 | 371.7 | 10.77 (s br, 1H); 9.05 (s br, 1H); 8.33 (dd, 1H); 8.16 (ddd, 1H); 7.98 (d, 1H); 7.96 (d, 2H); 7.88 (ddd, 1H); 7.77 (d, 1H); 7.66 (d, 2H); 7.55 (dd, 1H); 7.50 (d, 1H); 6.57 (d, 1H) |
| 36 | 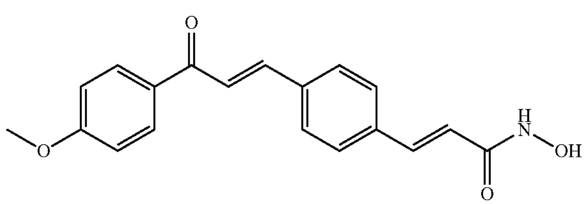 | N-hydroxy-3-{4-[3-(4-methoxy-phenyl)-3-oxo-propenyl]-phenyl}-acrylamide | A, 6.33 | 324.0 | 8.17 (d, 2H); 7.96 (d, 1H); 7.91 (d, 2H); 7.70 (d, 1H); 7.64 (d, 2H); 7.49 (d, 2H); 7.03 (d, 2H); 6.56 (d, 1H); 3.88 (s, 3H) |

TABLE 2-continued

| Ex no | structure | Compound name | LC-MS method; RT min | MH+ | 1H-NMR (DMSO-d6) δ: |
|---|---|---|---|---|---|
| 37 | 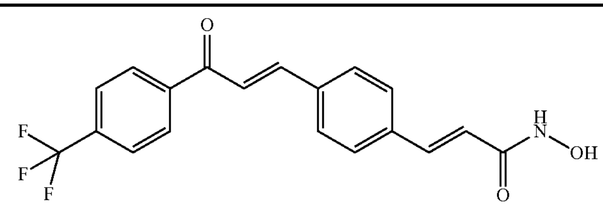 | N-Hydroxy-3-{4-[3-oxo-3-(4-trifluoromethyl-phenyl)-propenyl]-phenyl}-acrylamide | A, 6.95 | 361.6 | 10.73 (s br, 1H); 10.23 (s br, 1H); 8.33 (d, 2H); 7.97 (d, 1H); 7.94 (d, 2H); 7.79 (d, 1H); 7.66 (d, 2H); 7.49 (d, 1H); 6.59 (d, 1H) |
| 38 | 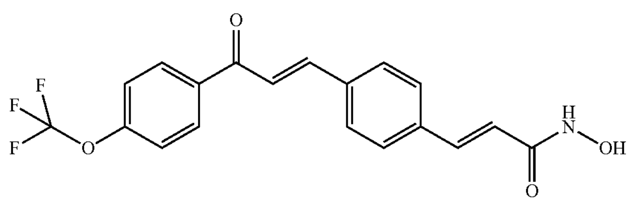 | N-hydroxy-3-{4-[3-oxo-3-(4-trifluoromethoxy-phenyl)-propenyl]-phenyl}-acrylamide | A, 7.01 | 378.0 | 8.29 (d, 2H); 7.97 (d, 1H); 7.93 (d, 2H); 7.76 (d, 1H); 7.65 (d, 2H); 7.54 (d, 2H); 7.49 (d, 1H); 6.59 (d, 1H) |
| 39 | 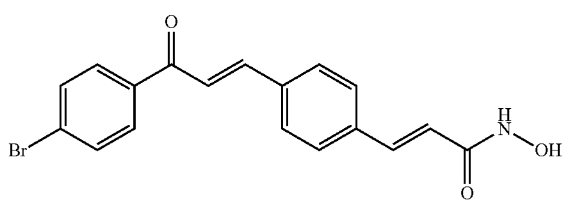 | 3-{4-[3-(4-bromo-phenyl)-3-oxo-propenyl]-phenyl}-N-hydroxy-acrylamide | A, 6.88 | 371.7 | 8.10 (d, 2H); 7.94 (d, 1H); 7.92 (d, 2H); 7.79 (d, 2H); 7.75 (d, 1H); 7.65 (d, 2H); 7.48 (d, 1H); 6.57 (d, 1H) |
| 40 | 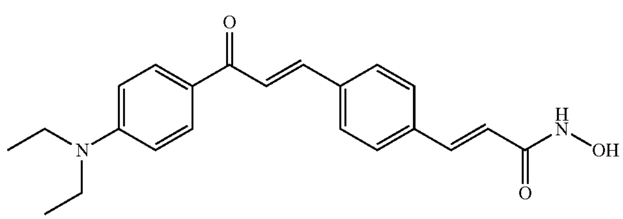 | 3-{4-[3-(4-diethylamino-phenyl)-3-oxo-propenyl]-phenyl}-N-hydroxy-acrylamide | A, 6.36 | 365.1 | 10.76 (s br, 1H); 9.04 (s br, 1H); 8.02 (d, 2H); 7.91 (d, 1H); 7.88 (d, 2H); 7.63 (d, 2H); 7.62 (d, 1H); 7.49 (d, 1H); 6.73 (d, 2H); 6.53 (d, 1H); 3.46 (q, 4H); 1.14 (t, 6H) |

TABLE 2-continued

| Ex no | structure | Compound name | LC-MS method; RT min | MH+ | ¹H-NMR (DMSO-d₆) δ: |
|---|---|---|---|---|---|
| 41 | 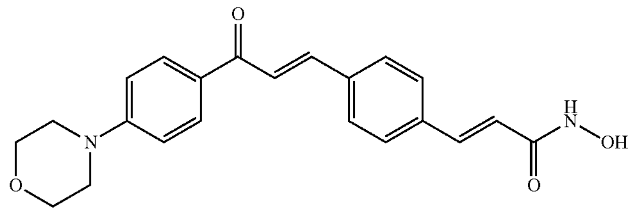 | N-hydroxy-3-{4-[3-(4-morpholin-4-yl-phenyl)-3-oxo-propenyl]-phenyl}-acrylamide | B, 5.78 | 379.2 | 8.08 (d, 2H); 7.95 (d, 1H); 7.90 (d, 2H); 7.66 (d, 1H); 7.63 (d, 2H); 7.48 (d, 1H); 7.03 (d, 2H); 6.56 (d, 1H); 3.75 (m, 4H); 334 (m, 4H) |
| 42 | 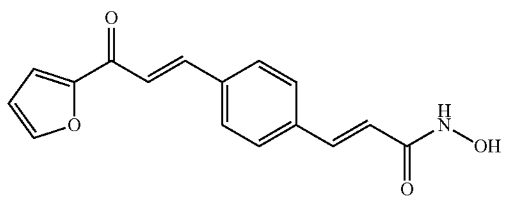 | 3-[4-(3-furan-2-yl-3-oxo-propenyl)-phenyl]-N-hydroxy-acrylamide | A, 6.25 | 284.1 | 8.07 (dd, 1H); 7.89 (d, 2H); 7.83 (dd, 1H); 7.73 (s, 2H); 7.65 (d, 2H); 7.48 (d, 1H); 6.80 (dd, 1H); 6.58 (d, 1H) |
| 43 | 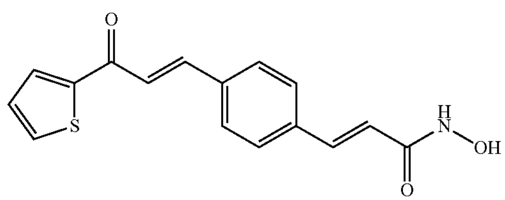 | N-hydroxy-3-{4-[3-oxo-3-thiophen-2-yl-propenyl]-phenyl]-acrylamide | B, 6.11 | 300.1 | 8.33 (dd, 1H); 8.06 (dd, 1H); 7.92 (d, 2H); 7.90 (d, 1H); 7.73 (d, 1H); 7.65 (d, 2H); 7.48 (d, 1H); 7.32 (dd, 1H); 6.58 (d, 1H) |
| 44 | 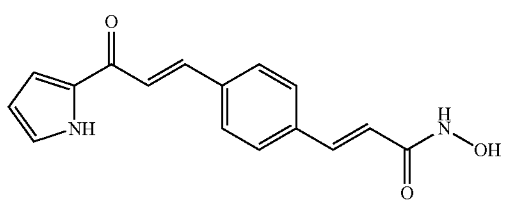 | N-hydroxy-3-{4-[3-oxo-3-(1H-pyrrol-2-yl)-propenyl]-phenyl]-acrylamide | A, 6.05 | 283.1 | 11.96 (s, 1H); 10.76 (s br, 1H); 9.05 (s br, 1H); 7.87 (d, 2H); 7.72 (d, 1H); 7.64 (d, 1H); 7.63 (d, 2H); 7.48 (d, 1H); 7.37 (m, 1H); 7.17 (m, 1H); 6.54 (d, 1H); 6.28 (m, 1H) |

TABLE 2-continued

| Ex no | structure | Compound name | LC-MS method; RT min | MH+ | ¹H-NMR (DMSO-d₆) δ: |
|---|---|---|---|---|---|
| 45 | 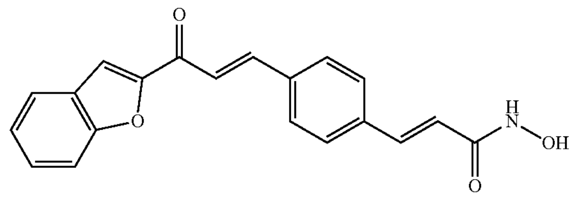 | 3-[4-(3-benzofuran-2-yl-3-oxo-propenyl)-phenyl]-N-hydroxy-acrylamide | B, 6.21 | 334.2 | 8.31 (s, 1H); 7.94 (d, 2H); 7.89 (d, 1H); 7.82 (d, 1H); 7.67 (d, 2H); 7.57 (ddd, 1H); 7.49 (d, 1H); 7.40 (ddd, 1H); 6.59 (d, 1H) |
| 46 | 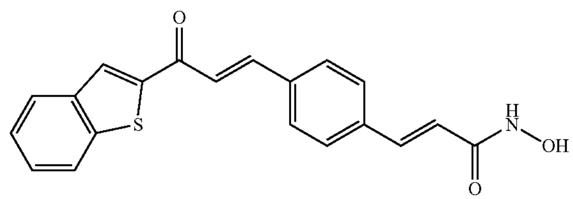 | 3-[4-(3-benzo[b]thiophen-2-yl-3-oxo-propenyl)-phenyl]-N-hydroxy-acrylamide | B, 6.49 | 350.1 | 10.76 (s br, 1H); 9.05 (s br, 1H); 8.07 (d, 1H); 8.05 (d, 2H); 7.97 (d, 2H); 7.79 (d, 1H); 7.68 (d, 2H); 7.60-7.46 (m, 2H); 7.52 (d, 1H); 6.58 (d, 1H) |
| 47 | 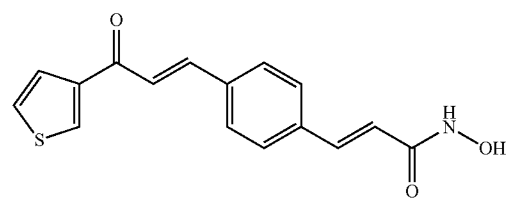 | N-hydroxy-3-[4-(3-oxo-3-thiophen-3-yl-propenyl)-phenyl]-acrylamide | B, 6.0 | 300.1 | (1H DMSO): 8.82 (dd, 1H); 7.90 (m, 2H); 7.87 (d, 1H); 7.70 (d, 1H); 7.70-7.61 (m, 4H); 7.47 (d, 1H); 7.57 (d, 1H). |
| 48 | 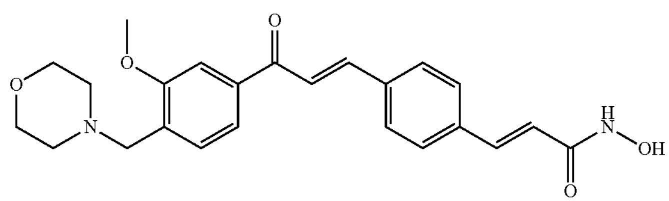 | N-hydroxy-3-{4-[3-(3-methoxy-4-morpholin-4-ylmethyl-phenyl)-3-oxo-propenyl]-phenyl}-acrylamide | B, 5.11 | 423.2 | 10.88 (s br, 1H); 9.11 (s br, 1H); 8.54 (s, 1H); 8.28 (dd, 1H); 8.04 (d, 1H); 7.96 (d, 1H); 7.74 (d, 1H); 7.64 (d, 2H); 7.48 (d, 1H); 7.29 (d, 1H); 6.57 (d, 1H); 4.40 (s, 2H); 3.98 (s, 3H); 3.94 (m, 2H); 3.82 (m, 2H); 3.32 (m, 2H); 3.17 (m, 2H) |

Example 49

3-{4-[3-(3,4-difluoro-phenyl)-3-oxo-propenyl]-phenyl}-N-hydroxy-acrylamide

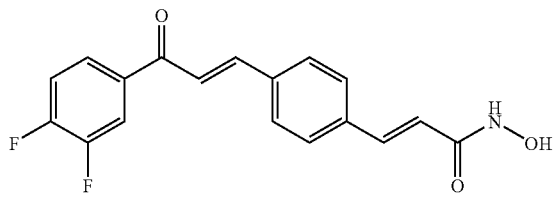

Step A

A solution of 4-bromo benzaldehyde (2 g, 10.8 mmol) in DMF (50 ml) and triethylamine (3.4 ml, 27 mmol) was degassed flushing $N_2$ for 30 min. $PPh_3$ (141 mg, 0.54 mmol), $Pd(OAc)_2$ (48.4 mg, 0.21 mmol), $NaHCO_3$ (1.84 g, 21.6 mmol) and tert-butyl acrylate (1.58 ml, 10.8 mmol) were added and the resulting mixture was heated to reflux for 3 h. Additional $Pd(OAc)_2$ (24 mg) was added and the mixture was heated to 100° C. for 1 h. The solution was diluted with $H_2O$ and extracted with $Et_2O$. The organic layer was dried over $Na_2SO_4$ and the solvent was evaporated under vacuo to give the crude product that was triturated in isopropyl ether to give 1.6 g of 3-(4-formyl-phenyl)-acrylic acid tert-butyl ester.

Yield: 70%

Step B

3-(4-formyl-phenyl)-acrylic acid tert-butyl ester (150 mg, 0.64 mmol) and KOH (72 mg, 1.28 mmol)) were dissolved in ethanol/water (1:1, 5 ml) and 3,4-difluoroacetophenone (83.2 µl, 0.64 mmol) was added to the resulting solution. The resulting mixture was stirred at room temperature overnight and then diluted with $H_2O$. The precipitate was filtered and dried under vacuo to give 210 mg of 3-{4-[3-(3,4-difluoro-phenyl)-3-oxo-propenyl]-phenyl}-acrylic acid tert-butyl ester.

Yield: 88%.

Step C

3-{4-[3-(3,4-difluoro-phenyl)-3-oxo-propenyl]-phenyl}-acrylic acid tert-butyl ester (210 mg, 0.56 mmol) was dissolved in DCM (5 ml) and trifluoroacetic acid was added (2 ml). The reaction was stirred at room temperature for 12 h. The solvent was evaporated under vacuo giving 200 mg of 3-{4-[3-(3,4-difluoro-phenyl)-3-oxo-propenyl]-phenyl}-acrylic acid.

Yield: quantitative

Step D

3-{4-[3-(3,4-difluoro-phenyl)-3-oxo-propenyl]-phenyl}-acrylic acid (100 mg, 0.32 mmol) was dissolved in DCM (10 ml). HOBT (72 mg, 0.44 mmol), EDC (91 mg, 0.44 mmol), TEA (129 µl, 0.96 mmol) and $NH_2OTHP$ (55 mg, 0.32 mmol) were added to the resulting solution. The mixture was stirred overnight at room temperature then partitioned between water and EtOAc. The organic extract was washed with water then dried over $Na_2SO_4$ and evaporated under vacuo.

The crude product was purified on silica gel chromatography (petroleum ether/EtOAc 8:2) and the resulting oil was dissolved in DCM and treated with $HCl/Et_2O$ for 1 h. The precipitate was filtered on Buckner funnel and dried under vacuo to give 40 mg of 3-{4-[3-(3,4-difluoro-phenyl)-3-oxo-propenyl]-phenyl}-N-hydroxy-acrylamide.

Yield: 40%

LC-MS Method=B RT=6.29; (ES+) gave $MH^+$: 330.1

$^1$H-NMR (DMSO-$d_6$,) δ: 10.72 (s br, 1H); 9.16 (s br, 1H); 8.25 (ddd, 1H); 8.08 (m, 1H); 7.98 (d, 1H); 7.95 (d, 2H); 7.77 (d, 1H); 7.70-7.60 (m, 3H); 7.49 (d, 1H); 6.57 (d, 1H)

The compounds reported in Table 3 were prepared according to the procedure described above

TABLE 3

| Ex no | structure | Compound name | LC-MS method; RT min | MH+ | $^1$H-NMR (DMSO-$d_6$) δ: |
|---|---|---|---|---|---|
| 50 | 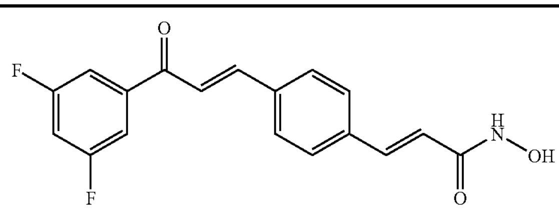 | 3-{4-[3-(3,5-difluoro-phenyl)-3-oxo-propenyl]-phenyl}-N-hydroxy-acrylamide | A, 6.64 | 330.1 | 10.80 (s br, 2H); 7.98 (d, 1H); 7.97 (d, 2H); 7.93-7.84 (m, 2H); 7.80 (d, 1H); 7.66 (d, 2H); 7.60 (ddd, 1H); 7.49 (d, 1H); 6.58 (d, 1H) |
| 51 | 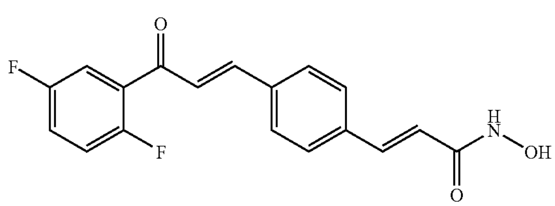 | 3-{4-[3-(2,5-difluoro-phenyl)-3-oxo-propenyl]-phenyl}-N-hydroxy-acrylamide | A, 6.52 | 330.1 | 10.77 (s br, 1H); 9.03 (s br, 1H); 7.84 (d, 2H); 7.71-7.59 (m, 4H); 7.57-7.41 (m, 4H); 6.55 (d, 1H) |
| 52 | 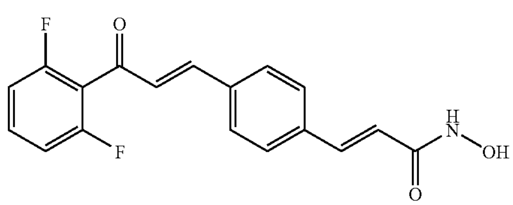 | 3-{4-[3-(2,6-difluoro-phenyl)-3-oxo-propenyl]-phenyl}-N-hydroxy-acrylamide | A, 6.45 | 330.1 | 10.80 (s br, 2H); 7.82 (d, 2H); 7.70-7.58 (m, 3H); 7.52 (d, 1H); 7.47 (d, 1H); 7.33-7.22 (m, 3H); 6.56 (d, 1H) |

TABLE 3-continued

| Ex no | structure | Compound name | LC-MS method; RT min | MH+ | ¹H-NMR (DMSO-d₆) δ: |
|---|---|---|---|---|---|
| 53 | 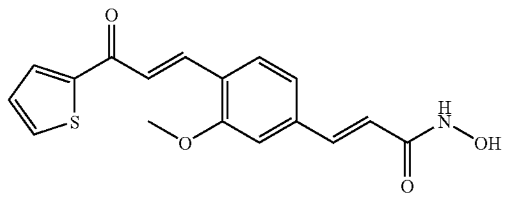 | N-hydroxy-3-[3-methoxy-4-(3-oxo-3-thiophen-2-yl-propenyl)-phenyl]-acrylamide | B, 5.97 | 330.2 | 10.73 (s br 1H); 8.27 (d, 1H); 8.06 (d, 1H); 8.01 (d, 1H); 8.00 (d, 1H); 7.85 (d, 1H); 7.49 (d, 1H); 7.34-7.22 (m, 3H); 6.60 (d, 1H); 3.95 (s, 3H) |
| 54 | 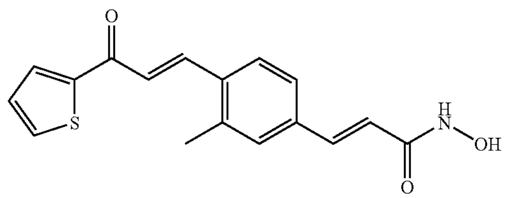 | N-hydroxy-3-[3-methyl-4-(3-oxo-3-thiophen-2-yl-propenyl)-phenyl]-acrylamide | B, 5.97 | 314.2 | 10.75 (s br, 1H); 8.33 (dd, 1H); 8.07 (dd, 1H); 8.04 (d, 1H); 7.94 (d, 1H); 7.81 (d, 1H); 7.53-7.39 (m, 3H); 7.32 (dd, 1H); 6.54 (d, 1H); 2.47 (s, 3H) |
| 55 | 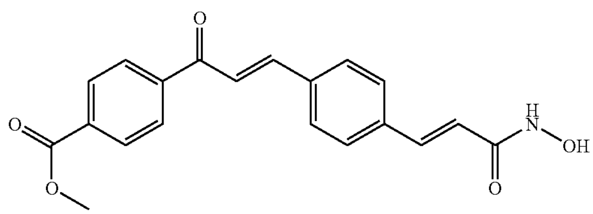 | 4-{3-[4-(2-hydroxy-carbamoyl-vinyl)-phenyl]-acryloyl}-benzoic acid methyl ester | A, 6.5 | 352.1 | 10.77 (s, 1H); 9.04 (s br, 1H); 8.27 (d, 2H); 8.12 (d, 1H); 7.97 (d, 1H); 8.94 (d, 2H); 7.78 (d, 1H); 7.66 (d, 2H); 7.49 (d, 1H); 6.57 (d, 1H); 3.91 (s, 3H) |
| 56 | 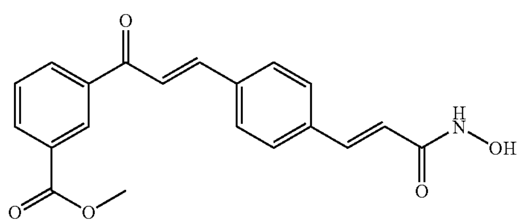 | 3-{3-[4-(2-hydroxy-carbamoyl-vinyl)-phenyl]-acryloyl}-benzoic acid methyl ester | A, 6.78 | 352.1 | 8.60 (dd, 1H); 8.46 (ddd, 1H); 8.23 (ddd, 1H); 7.99 (d, 1H); 7.95 (d, 2H); 7.79 (d, 1H); 7.75 (dd, 1H); 7.65 (d, 2H); 7.49 (d, 1H); 6.58 (d, 1H); 3.92 (s, 3H). |
| 57 | 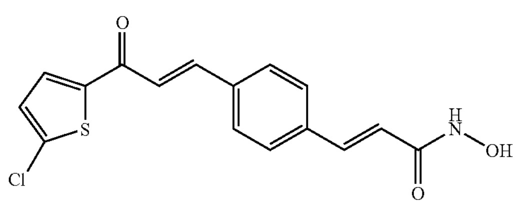 | 3-{4-[3-(5-chloro-thiophen-2-yl)-3-oxo-propenyl]-phenyl}-N-hydroxy-acrylamide | A, 6.79 | 334.0 | (1H DMSO): 10.78 (s br, 1H); 9.05 (s br, 1H); 8.27 (d, 1H); 7.92 (d, 2H); 7.89 (d, 1H); 7.73 (d, 1H); 7.66 (d, 2H); 7.49 (d, 1H); 7.39 (d, 1H); 6.56 (d, 1H). |
| 58 | 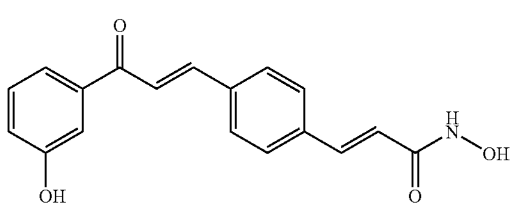 | N-hydroxy-3-{4-[3-(3-hydroxy-phenyl)-3-oxo-propenyl]-phenyl}-acrylamide | A, 5.85 | 310.1 | (1H DMSO): 10.74 (s br, 1H); 9.77 (s br, 1H); 7.95-7.83 (m, 3H); 7.70 (d, 1H); 7.63 (m, 3H); 7.48 (d, 1H); 7.45 (dd, 1H); 7.37 (dd, 1H); 7.06 (dd, 1H); 6.56 (d, 1H). |

TABLE 3-continued

| Ex no | structure | Compound name | LC-MS method; RT min | MH+ | 1H-NMR (DMSO-d6) δ: |
|---|---|---|---|---|---|
| 59 | 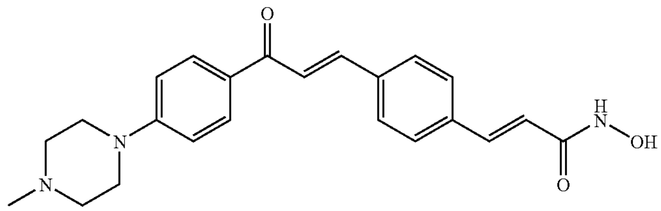 | N-hydroxy-3-(4-{3-[4-(4-methyl-piperazin-1-yl)-phenyl]-3-oxo-propenyl}-phenyl)-acrylamide | A, 5.11 | 392.2 | (1H DMSO): 10.78 (s br, 1H); 10.53 (s br, 1H); 9.04 (s br, 1H); 8.10 (d, 2H); 7.95 (d, 1H); 7.91 (d, 2H); 7.68 (d, 1H); 7.63 (d, 2H); 7.48 (d, 1H); 7.11 (d, 2H); 6.57 (d, 1H); 4.13 (m, 2H); 2.51 (m, 2H); 3.33-3.04 (m, 4H); 2.83 (s br, 3H). |

Example 60

N-hydroxy-3-[2-methoxy-4-(3-oxo-3-phenyl-propenyl)-phenyl]-acrylamide

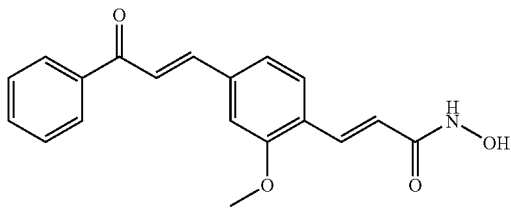

Step A 4-bromo-2-methoxybenzaldehyde (1 g, 4.67 mmol) was dissolved in MeOH (20 ml) and trimethyl orthoformate (562 μl, 5.139 mmol) and p-toluene sulphonic acid monohydrate (89 mg, 0.467 mmol) were added to the resulting solution. The mixture was stirred overnight at room temperature and then the solvent was removed under vacuo. The residue was taken up with Et$_2$O and washed with 5% Na$_2$CO$_3$ and with water. The organic phase was dried over Na$_2$SO$_4$ and evaporated to give 1.22 g of 4-bromo-1-dimethoxymethyl-2-methoxy-benzene as a colorless oil.

Yield=99%

Step B 4-bromo-1-dimethoxymethyl-2-methoxy-benzene (1.22 g, 4.67 mmol) was dissolved in dry THF (16 ml) and the resulting solution was cooled to −78° C. under N$_2$ atmosphere. n-BuLi in hexane (2.24 ml of a 2.5 M solution) was added dropwise and the mixture was stirred at −78° C. for 20 minutes and then treated with DMF (467 μl, 6.07 mmol) and stirred at room temperature for 0.5 h.

The solution was partitioned between Et$_2$O and water and the organic extract was washed with water and brine then dried over Na$_2$SO$_4$ and evaporated under vacuo. 716 mg of 4-dimethoxymethyl-3-methoxy-benzaldehyde were isolated by flash column chromatography on sylica gel (EtOAc/petroleum ether 1:6).

Yield=72%

Step C 4-dimethoxymethyl-3-methoxy-benzaldehyde (716 mg, 3.41 mmol) was dissolved in EtOH/H$_2$O (1:1, 20 ml) and to the resulting solution were added acetophenone (409 mg, 3.41 mmol) and 1.7 M KOH (3 ml).

The mixture was stirred for 5 h at room temperature, then diluted with EtOAc and washed twice with water. The organic phase was dried over Na$_2$SO$_4$ and evaporated under vacuo. The resulting oil was dissolved in THF (10 ml) and treated with 1N HCl (10 ml). The solution was stirred for 0.5 h at room temperature and then diluted with EtOAc and washed with water. The organic phase was dried over Na$_2$SO$_4$ and concentrated under vacuo. The resulting solid was triturated with EtOAc and filtered on a Buckner funnel giving 550 mg of 2-methoxy-4-(3-oxo-3-phenyl-propenyl)-benzaldehyde as a yellow powder.

Yield=61%

Step D 2-methoxy-4-(3-oxo-3-phenyl-propenyl)-benzaldehyde (550 mg, 2.07 mmol) was dissolved in THF (5 ml) and the resulting solution was added to a stirring mixture of tert-butyl diethylphosphonoacetate (603 mg, 2.27 mmol) and NaH (107 mg, 2.69 mmol, 60% oil dispersion) in THF (5 ml). After 15 minutes the reaction was quenched by the addition of water and partitioned between water and EtOAc. The organic extract was dried over Na$_2$SO$_4$ and evaporated under vacuo giving a crude that was purified by silica gel chromatography (EtOAc/petroleum ether 1:6). The collected fraction gave 635 mg of 3-[2-methoxy-4-(3-oxo-3-phenyl-propenyl)-phenyl]-acrylic acid tert-butyl ester as a yellow oil.

Yield=84%

Step E

3-[2-methoxy-4-(3-oxo-3-phenyl-propenyl)-phenyl]-acrylic acid tert-butyl ester (635 mg, 1.74 mmol) was dissolved in DCM (12 ml) and TFA (3 ml) was added to the resulting solution. After stirring for 2 h at room temperature the solvent was removed under vacuo giving 541 mg of 3-[2-methoxy-4-(3-oxo-3-phenyl-propenyl)-phenyl]-acrylic acid as yellow powder.

Yield=99%

Step F

3-[2-methoxy-4-(3-oxo-3-phenyl-propenyl)-phenyl]-acrylic acid (200 mg, 0.65 mmol) was dissolved in THF (6 ml) and HOBT (196 mg, 1.30 mmol), EDC (248 mg, 1.30 mmol), TEA (1820, 1.30 mmol) and NH$_2$OTHP (91 mg, 0.78 mmol) were added to the resulting solution. The mixture was stirred overnight at room temperature and then partitioned between water and EtOAc. The organic extract was washed 3 times with water, dried over Na$_2$SO$_4$ and evaporated under vacuo.

The crude product was purified by silica gel chromatography (EtOAc/petroleum ether 1:1) and the resulting solid was dissolved in DCM and treated with HCl/Et$_2$O for 15 minutes. The precipitate was filtered on Buckner funnel giving 118 mg of N-hydroxy-3-[2-methoxy-4-(3-oxo-3-phenyl-propenyl)-phenyl]-acrylamide.

Yield=56%

LC-MS Method=A RT=7.42; (ES+) gave MH$^+$: 324.1

$^1$H-NMR (DMSO-d$_6$,) δ: 8.16 (d, 2H); 7.98 (d, 1H); 7.74 (d, 1H); 7.68 (m, 2H); 7.63-7.54 (m, 4H); 7.49 (d, 1H); 7.60 (d, 1H); 3.97 (s, 3H).

The compounds reported in Table 4 were prepared according to the procedure described above To the mixture were added NaHCO$_3$ (481 mg, 5.73 mmol), PPh$_3$ (37.5 mg, 0.14 mmol), Pd(OAc)$_2$ (13 mg, 0.06 mmol), tert-butyl acrylate (420 μl, 2.87 mmol) and the reaction was heated to 100° C. for 5 h. The resulting brown solution was partitioned between water and Et$_2$O and the organic extract was washed with water, dried over Na$_2$SO$_4$ and evaporated under vacuo giving the crude product that was purified by silica gel chromatography (petroleum ether/EtOAc 1:1). The collected fraction gave 680 mg of 3-[4-(3-oxo-3-pyridin-3-yl-propenyl)-phenyl]-acrylic acid tort-butyl ester.

Yield=70%

Step C

3-[4-(3-oxo-3-pyridin-3-yl-propenyl)-phenyl]-acrylic acid tert-butyl ester (680 mg, 2.03 mmol) was dissolved in DCM (15 ml) and TFA (5 ml). The resulting solution was

TABLE 4

| Ex no | structure | Compound name | LC-MS method; RT min | MH+ | $^1$H-NMR (DMSO-d$_6$) δ: |
|---|---|---|---|---|---|
| 61 | 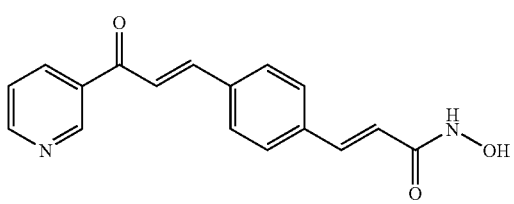 | 3-[2-fluoro-4-(3-oxo-3-phenyl-propenyl)-phenyl]-N-hydroxy-acrylamide | B, 6.20 | 312.1 | 10.87 (s br, 1H); 9.07 (s br, 1H); 8.18 (d, 2H); 8.04 (d, 1H); 7.93 (d, 1H); 7.78-7.65 (m, 4H); 7.58 (m, 2H); 7.52 (d, 1H); 6.66 (d, 1H) |
| 62 | 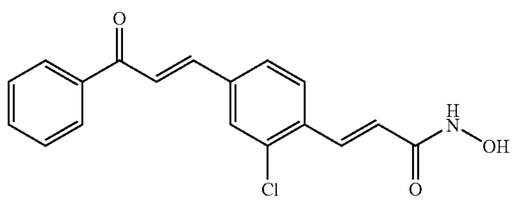 | 3-[2-chloro-4-(3-oxo-3-phenyl-propenyl)-phenyl]-N-hydroxy-acrylamide | A, 6.62 | 328.1 | 8.18 (d, 2H); 8.15 (d, 1H); 8.05 (d, 1H); 7.89 (dd, 1H); 7.78 (d, 1H); 7.74 (d, 1H); 7.71 (d, 1H); 7.69 (dd, 1H); 7.58 (dd, 2H); 6.63 (d, 1H) |

Example 63

N-hydroxy-3-[4-(3-oxo-3-pyridin-3-yl-propenyl)-phenyl]-acrylamide

Step A 4-bromo benzaldehyde (1 g, 5.40 mmol) was dissolved in MeOH (26 ml) and 2M NaOH (5.4 ml). The resulting solution was cooled to 0° C. and 3-acetyl-pyridine (592 μl, 5.40 mmol) was added dropwise. The mixture was stirred for 1 h at 0° C. then the resulting solid was filtered and washed with MeOH giving 832 mg of 3-(4-bromo-phenyl)-1-pyridin-3-yl-propenone as a white powder.

Yield=53%

Step B 3-(4-bromo-phenyl)-1-pyridin-3-yl-propenone (823 mg, 2.87 mmol) was dissolved in DMF (18 ml) and TEA (1.9 ml) and the resulting solution was degassed flushing N$_2$ for 20 min.

stirred at room temperature for 4 h then the solvent was removed under vacuo giving 600 mg of 3-[4-(3-oxo-3-pyridin-3-yl-propenyl)-phenyl]-acrylic acid as trifluoro acetate salt.

Yield=75

Step D

3-[4-(3-oxo-3-pyridin-3-yl-propenyl)-phenyl]-acrylic acid trifluoro acetate salt (550 mg, 1.4 mmol) was dissolved in THF/DMF (1:1, 20 ml) and to the resulting solution were added HOBT (536 mg, 3.94 mmol), EDC (752 mg, 3.94 mmol), TEA (822 μl, 3.94 mmol) and NH$_2$OTHP (276 mg, 2.36 mmol). The mixture was stirred overnight at room temperature then partitioned between water and EtOAc. The organic extract was washed with water and brine then dried over Na$_2$SO$_4$ and evaporated under vacuo.

The crude product was purified by silica gel chromatography (EtOAc) and the resulting oil was dissolved in DCM and treated with HCl/Et$_2$O for 1 h. The precipitate was filtered on Buckner funnel and was triturated in hot EtOH to give 380 mg of N-hydroxy-3-[4-(3-oxo-3-pyridin-3-yl-propenyl)-phenyl]-acrylamide as hydrochloric salt.

Yield=82%

LC-MS Method=B RT=4.99; (ES+) gave MH$^+$: 295.1

$^1$H-NMR (DMSO-d$_6$,) δ: 9.43 (d, 1H); 8.93 (dd, 1H); 8.69 (ddd, 1H); 8.01 (d, 1H); 7.96 (d, 2H); 7.82 (d, 1H); 7.81 (m, 1H); 7.67 (d, 2H); 7.49 (d, 1H); 6.59 (d, 1H)

The compounds reported in Table 5 were prepared according to the procedure described above

TABLE 5

| Ex no | structure | Compound name | LC-MS method; RT min | MH+ | $^1$H-NMR (DMSO-$d_6$) δ: |
|---|---|---|---|---|---|
| 64 | 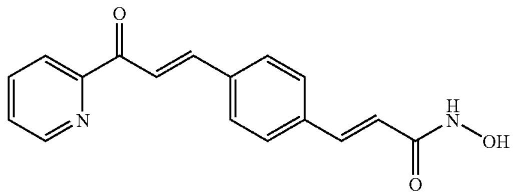 | N-hydroxy-3-[4-(3-oxo-3-pyridin-2-yl-propenyl)-phenyl]-acrylamide | A, 5.76 | 295.1 | 8.81 (m, 1H); 8.29 (d, 1H); 8.12 (dd, 1H); 8.07 (ddd, 1H); 7.87 (d, 2H); 7.86 (d, 1H); 7.71 (ddd, 1H); 7.66 (d, 2H); 6.48 (d, 1H); 6.56 (d, 1H) |
| 65 | 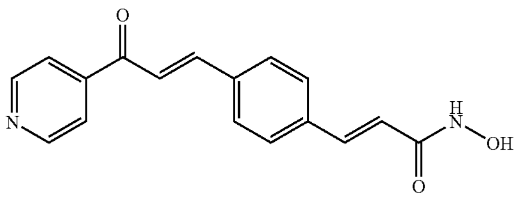 | N-hydroxy-3-[4-(3-oxo-3-pyridin-4-yl-propenyl)-phenyl]-acryamide | B, 4.98 | 295.1 | 8.92 (m, 2H); 8.12 (m, 2H); 7.95 (d, 2H); 7.92 (d, 1H); 7.80 (d, 1H); 7.67 (d, 2H); 7.49 (d, 1H); 6.58 (d, 1H) |
| 66 | 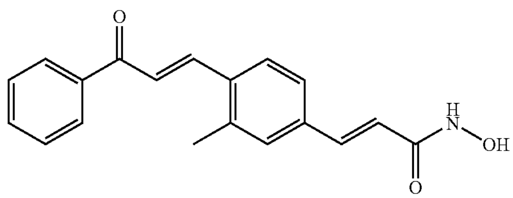 | N-hydroxy-3-[3-methyl-4-(3-oxo-3-phenyl-propenyl)-phenyl]-acrylamide | A, 5.34 | 308.1 | 10.74 (s br, 1H); 9.06 (s br, 1H); 8.16 (d, 2H); 8.05 (d, 1H); 7.97 (d, 1H); 7.86 (d, 1H); 7.68 (dd, 1H); 7.58 (dd, 2H); 7.47 (m, 2H); 7.43 (d, 1H); 7.54 (d, 1H); 2.47 (s, 3H) |
| 67 | 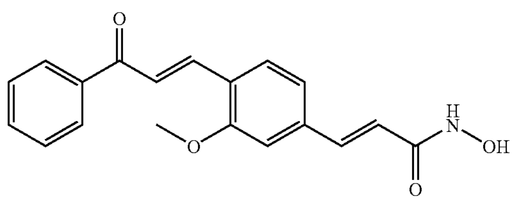 | N-hydroxy-3-[3-methoxy-4-(3-oxo-3-phenyl-propenyl)-phenyl]-acrylamide | A, 6.47 | 324 | 10.75 (s br, 1H); 9.07 (s br, 1H); 8.12 (d, 2H); 8.02 (d, 1H); 8.01 (d, 1H); 7.90 (d, 1H); 7.67 (dd, 1H); 7.57 (dd, 2H); 7.49 (d, 1H); 7.31 (s, 1H); 7.25 (d, 1H); 6.59 (d, 1H); 3.95 (s, 3H) |

Example 68

3-[3-fluoro-4-(3-oxo-3-pyridin-3-yl-propenyl)-phenyl]-N-hydroxacrylamide

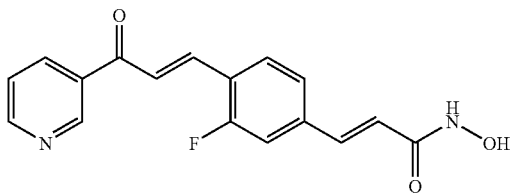

Step A 4-bromo-2-fluoro benzaldehyde (988 mg, 4.86 mmol) and 3-acetyl-pyridine (533 µl, 4.86 mmol) were dissolved in EtOH (10 ml) and TEA (10.8 ml). The resulting solution was heated to reflux for 16 h then additional amount of TEA (5 ml) was added. The mixture was heated to reflux for 16 h then the solvent was removed under vacuo and the residue was taken up with water and EtOAc. The organic extract was dried over Na$_2$SO$_4$ and evaporated. The resulting solid was triturated with isopropyl ether and filtered on a buckner funnel to give 680 mg of 3-(4-bromo-2-fluoro-phenyl)-1-pyridin-3-yl-propenone as a yellow powder.
Yield=45%

Step B 3-(4-bromo-phenyl)-1-pyridin-3-yl-propenone (668 mg, 2.18 mmol) were dissolved in DMF (11 ml) and TEA (1.3 ml) and the resulting solution was degassed flushing N$_2$ for 20 min.

To the mixture were added NaHCO$_3$ (366 mg, 4.37 mmol), PPh$_3$ (28.5 mg, 0.11 mmol), Pd(OAc)$_2$ (10 mg, 0.044 mmol), tert-butyl acrylate (352 µl, 2.40 mmol) and the reaction was heated to 100° C. for 5 h. The resulting brown solution was partitioned between water and Et$_2$O and the organic extract was washed with water, dried over Na$_2$SO$_4$ and evaporated under vacuo giving the crude product that was purified on silica gel chromatography (petroleum ether/EtOAc 7:3). The collected fractions gave 550 mg of 3-[3-fluoro-4-(3-oxo-3-pyridin-3-yl-propenyl)-phenyl]-acrylic acid tert-butyl ester.
Yield=71%

Step C

3-[3-fFluoro-4-(3-oxo-3-pyridin-3-yl-propenyl)-phenyl]-acrylic acid tert-butyl ester (550 mg, 1.55 mmol) was dissolved in DCM (15 ml) and TFA (5 ml). The resulting solution was stirred at RT for 4 h then the solvent was removed under vacuo giving 636 mg of 3-[3-fluoro-4-(3-oxo-3-pyridin-3-yl-propenyl)-phenyl]-acrylic acid as trifluoro acetate salt.
Yield=quantitative

Step D

3-[3-fluoro-4-(3-oxo-3-pyridin-3-yl-propenyl)-phenyl]-acrylic acid trifluoro acetate salt (300 mg, 0.64 mmol) was dissolved in THF (5 ml) and DMF (2 ml). To the resulting solution HOBT (174 mg, 1.28 mmol), EDC (245 mg, 1.28 mmol), TEA (178 µl, 1.28 mmol) and NH₂OTHP (90 mg, 0.77 mmol) were added. The mixture was stirred for 6 h at room temperature and then partitioned between water and EtOAc. The organic extract was washed with water, brine, dried over Na₂SO₄ and evaporated under vacuo.

The crude product was triturated in EtOAc, filtered on a Bucker funnel and the resulting solid was dissolved in DCM and treated with HCl/Et₂O for 3 h. The precipitate was filtered giving 150 mg of 3-[3-fluoro-4-(3-oxo-3-pyridin-3-yl-propenyl)-phenyl]-N-hydroxy-acrylamide as hydrochloric salt.

Yield=67%

LC-MS Method=A RT=5.23; (ES+) gave MH⁺: 313.1

¹H-NMR (DMSO-d₆,) δ: 9.40 (d, 1H); 8.92 (dd, 1H); 8.63 (ddd, 1H); 8.20 (dd, 1H); 8.05 (d, 1H); 7.87 (d, 1H); 7.77 (dd, 1H); 7.55 (m, 2H); 7.48 (d, 1H); 6.63 (d, 1H).

Example 69

N-hydroxy-3-[5-(3-oxo-3-phenyl-propenyl)-pyridin-2-yl]-acrylamide

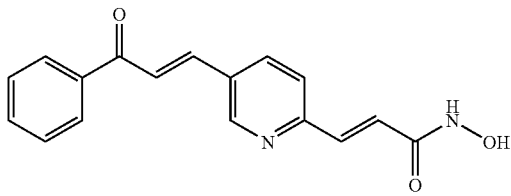

Step A

Trimethyl orthoformate (643 µl, 5.9 mmol) and p-toluene sulphonic acid monohydrate (102 mg, 0.54 mmol) were added to 6-bromo-pyridine-3-carbaldehyde (1 g, 5.37 mmol) dissolved in MeOH (40 ml). The mixture was stirred for 24 h at room temperature and then partitioned between water and Et₂O. The organic extract was washed with water, 5% Na₂CO₃, dried over Na₂SO₄ and evaporated under vacuo to give 1.2 g of 2-bromo-5-dimethoxymethyl-pyridine as a brown oil.

Yield=99%

Step B 2-bromo-5-dimethoxymethyl-pyridine (503 mg, 2.13 mmol) was dissolved in dry THF (20 ml) and the resulting solution was cooled to −70° C. under N₂ atmosphere. 2.5 M Solution of n-BuLi in hexane (0.94 ml) was added dropwise and the mixture was stirred at −70° C. for 15 minutes then treated with DMF (245 µl, 3.19 mmol).

After 30 minutes the temperature was allowed to reach RT and the mixture was partitioned between water and Et₂O. The organic extract was dried over Na₂SO₄ and evaporated under vacuo. The crude product was purified by chromatographic column (petroleum ether/EtOAc 7:3) to give 206 mg of 5-dimethoxymethyl-pyridine-2-carbaldehyde.

Yield=44%

Step C 5-dimethoxymethyl-pyridine-2-carbaldehyde (355 mg, 1.97 mmol) was dissolved in THF (10 ml) and the resulting solution was added to a stirring mixture of tert-butyl diethylphosphonoacetate (547 mg, 2.169 mmol) and NaH (102 mg, 2.56 mmol, 60% oil dispersion) in THF (5 ml). After 15 minutes the reaction was quenched by addition of water and the resulting slurry was extracted with Et₂O. The organic phase was dried over Na₂SO₄ and evaporated under vacuo. The crude product was purified by silica gel chromatography (petroleum ether/EtOAc 95:5) to give 491 mg of 3-(5-dimethoxymethyl-pyridin-2-yl)-acrylic acid tert-butyl ester.

Yield=89%

Step D (491 mg, 1.76 mmol) of 3-(5-dimethoxymethyl-pyridin-2-yl)-acrylic acid tert-butyl ester was dissolved in THF (20 ml) and 1N HCl (7 ml).

The resulting solution was stirred for 4 h. Water (1 ml) and 10% HCl (1 ml) were added. The mixture was stirred overnight then basified to pH=10 with 20% NaOH and extracted with EtOAc. The organic phase was dried over Na₂SO₄ and evaporated under vacuo giving 3-(5-formyl-pyridin-2-yl)-acrylic acid tert-butyl ester as a solid.

Yield=88%

Step E 3-(5-formyl-pyridin-2-yl)-acrylic acid tert-butyl ester (364 mg, 1.56 mmol) was dissolved in MeOH (10 ml) and the solution was cooled to 0° C. Acetophenone (188 mg, 1.56 mmol) and 1.7M KOH (1.8 ml) were added. The reaction was stirred at 0° C. for 3 h. The resulting solid was filtered on a Buckner funnel to give 130 mg of 3-[5-(3-oxo-3-phenyl-propenyl)-pyridin-2-yl]-acrylic acid tert-butyl ester as a yellow powder.

Yield=25%

Step F

3-[5-(3-oxo-3-phenyl-propenyl)-pyridin-2-yl]-acrylic acid tert-butyl ester (130 mg, 0.38 mmol) was dissolved in DCM (4 ml) and TFA (1 ml). The resulting solution was stirred for 4 h at room temperature and then the solvent was removed under vacuo. The resulting oil was crystallized from Et₂O to give 165 mg of 3-[5-(3-oxo-3-phenyl-propenyl)-pyridin-2-yl]-acrylic acid as the trifluoroacetate salt.

Yield=quantitative

Step G

HOBT (133 mg, 0.98 mmol), EDC (187 mg, 0.98 mmol), TEA (148 mg, 1.47 mmol) and NH₂OTHP (68.8 mg, 0.59 mmol) were added to 3-[5-(3-oxo-3-phenyl-propenyl)-pyridin-2-yl]-acrylic acid trifluoroacetate salt (193 mg, 0.49 mmol) dissolved in THF/DMF (1:1, 10 ml). The mixture was stirred for 6 h at room temperature and then partitioned between water and Et₂O. The organic extract was washed with brine, dried over Na₂SO₄ and evaporated under vacuo.

The crude product was purified by silica gel chromatography (petroleum ether/EtOAc 4:6) and the resulting oil was dissolved in DCM and treated with HCl/Et₂O for 1.5 h. The precipitate was filtered on a Buckner funnel washing with DCM and Et₂O to give 55 mg of N-hydroxy-3-[5-(3-oxo-3-phenyl-propenyl)-pyridin-2-yl]-acrylamide as hydrochloric salt.

Yield=33%

LC-MS Method=B RT=5.58; (ES+) gave MH⁺: 295.2

¹H-NMR (DMSO-d₆,) δ: 9.06 (d, 1H); 8.45 (dd, 1H); 8.18 (d, 2H); 8.11 (d, 1H); 7.78 (d, 1H); 7.76-7.66 (m, 2H); 7.59 (dd, 2H); 7.53 (d, 1H); 7.04 (d, 1H)

The compounds reported in Table 6 were prepared according to the procedure described above.

TABLE 6

| Ex no | structure | Compound name | LC-MS method; RT min | MH+ | $^1$H-NMR (DMSO-$d_6$) δ: |
|---|---|---|---|---|---|
| 70 | 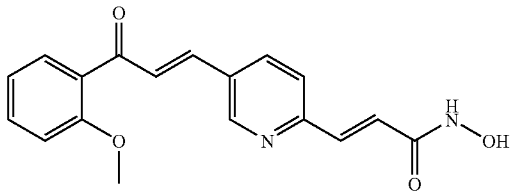 | N-hydroxy-3-{5-[3-(2-methoxy-phenyl)-3-oxo-propenyl]-pyridin-2-yl}-acrylamide | A, 5.71 | 325.2 | 8.93 (d, 1H); 8.27 (dd, 1H); 7.69 (d, 1H), 7.63-7.47 (m, 5H); 7.21 (d, 1H); 7.07 (ddd, 1H); 7.01 (d, 1H); 3.87 (s, 3H) |
| 71 | 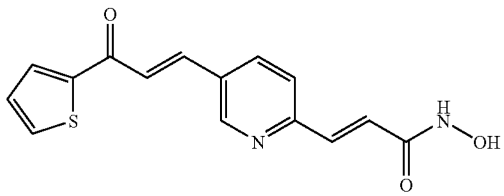 | N-hydroxy-3-[5-(3-oxo-3-thiophen-2-yl-propenyl)-pyridin-2-yl]-acrylamide | A, 5.58 | 301.2 | 9.05 (d, 1H); 8.40 (dd, 1H); 8.35 (dd, 1H); 8.09 (dd, 1H); 8.03 (d, 1H); 7.77 (d, 1H); 7.71 (d, 1H); 7.51 (d, 1H); 7.34 (dd, 1H); 7.02 (d, 1H); |
| 72 | 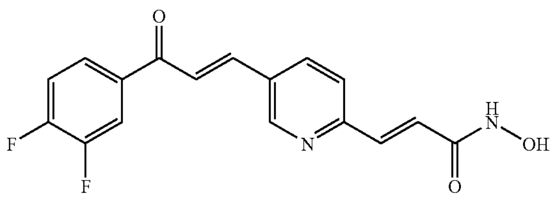 | 3-{5-[3-(3,4-difluoro-phenyl)-3-oxo-propenyl]-pyridin-2-yl}-N-hydroxy-acrylamide | A, 5.33 | 331.1 | 10.90 (s br, 1H); 9.04 (d, 1H); 8.42 (dd, 1H); 8.26 (ddd, 1H); 8.10 (d, 1H); 8.10 (m, 1H); 7.81 (d, 1H); 7.70 (d, 1H); 7.66 (dd, 1H); 7.52 (d, 1H); 7.02 (d, 1H). |

2. Biochemistry and Pharmacology

Acetylation and deacetylation of nucleosomal histones play an important role in the modulation of chromatin structure, chromatin function and in the regulation of gene expression. A number of structurally distinct classes of compounds have been identified as HDAC inhibitors; these compounds lead to an accumulation of acetylated histone proteins both in tumor cells and in normal tissues. HDAC inhibitors are able to activate differentiation, to arrest the cell cycle in G1 and/or G2, and to induce apoptosis in transformed or cancer cells.

Experiment Set 1

1. Histone Acetylation

U937 hematopoietic cell line was treated with several compounds in a concentration interval comparable to that of tricostatin A, a compound known among the most powerful known inhibitors of histone deacetylases (micromolar concentrations). The levels of histone acetylation were measured by cytofluorimetry, using an antibody recognising H3 and H4 acetylated histones. Similar results were obtained with a different technique (western blotting) and in other cell lines.

As shown in FIG. 1, the tested compounds showed a strong inhibitory activity, with a spectrum of potency and inhibition stability (by comparing data obtained after 4 h treatment) which correlates with the stability of the compounds and/or degree of inhibition of histone deacetylases.

2. Cell Growth/Apoptosis/Cell Cycle

The biological response of 0937 cells to the compounds of formula (I) was studied. As a reference, a 24 hr treatment with tricostatin A induced strong apoptosis in U937 cells (approximately 60% of cell death), together with a growing number of cells in G2/M phase, as previously described (Qiu et al., *Mol. Biol. Cell.*, 2000, 11(6), 2069-83).

Figure 2:
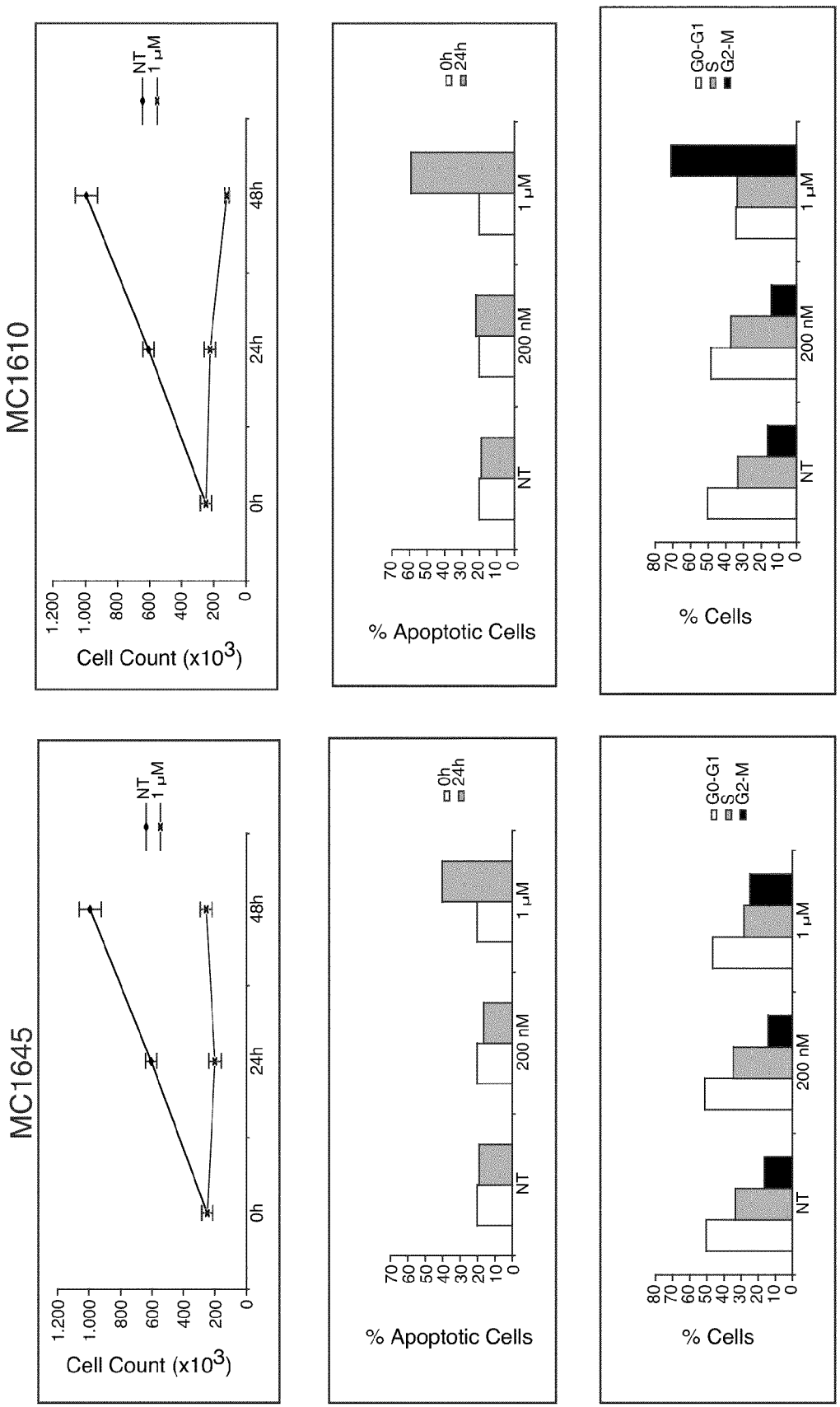
FIG. 2 is a Treatment of U937 cells with the compounds of the invention: effect on cell growth and apoptosis.

Two compounds (MC1610 and MC1645) were studied at first: as shown in FIG. 2, both compounds (concentration 1 μM) interrupted cell growth completely, induced apoptosis and stimulated blockage in G2/M phase.

According to the aforementioned procedures, the present compounds were thus tested for their inhibiting activity towards HD2, HD1-B and HD1-A, which are mais enzymes with deacetylase activity. In particular HD1-B and HD1-A are homologues of class I and II mammalian deacetylases respectively. The obtained results are shown in table 7.

TABLE 7

| Compound | Ar | HD2, IC$_{50}$ nM | HD1-B, IC$_{50}$ nM | HD1-A, IC$_{50}$ nM |
|---|---|---|---|---|
| MC1632 | Ph | 107 | 92 | 108 |
| MC1645 | 2-Cl-Ph | 40 | 22 | 39 |
| MC1622 | 3-Cl-Ph | 118 | 91 | 120 |
| MC1624 | 2-F-Ph | 86 | 18 | 67 |
| MC1610 | 3-F-Ph | 144 | 85 | 117 |
| MC1625 | 4-F-Ph | 92 | 86 | 107 |
| MC1644 | 2-Me-Ph | 81 | 14 | 15 |
| MC1623 | 3-Me-Ph | 462 | 273 | 109 |
| MC1639 | 4-Me-Ph | 216 | 225 | 310 |
| MC1652 | 1-naphtyl | 202 | 57 | 14 |
| MC1671 | 5-dihydrobenzofuran | 51 | 28 | 15 |

TABLE 7-continued

Ar—CO—CH=CH—(1,3-C6H4)—CH=CH—C(O)—NHOH

| Compound | Ar | HD2, IC$_{50}$ nM | HD1-B, IC$_{50}$ nM | HD1-A, IC$_{50}$ nM |
|---|---|---|---|---|
| MC1646 | Ph | 32 | 23 | 45 |
| MC1670 | 2-Cl-Ph | 65 | 29 | 40 |
| MC1672 | 3-Cl-Ph | 78 | 20 | 27 |
| MC1661 | 2-F-Ph | 38 | 16 | 17 |
| MC1653 | 3-F-Ph | 135 | 50 | 33 |

Ph—CH=CH—C(O)—(1,4-C6H4)—CH=CH—C(O)—NHOH

| Compound | Yield (%) | χ | Mp ° C. |
|---|---|---|---|
| MC1631 | 144 | 152 | 213 |

The data in table 7 show that all tested compounds have a powerful inhibiting activity of histone deacetylases.

Experiment set 2

Methods

In Vitro Studies
2.1 Histone Acetylation Assay

The histone acetylation assay is formatted for conventional detection of relative levels of acetylated histones in cell cultures. Suspension cells (U937 or K562, respectively derived from a histiocytic lymphoma and a myelogenous leukemia) were exposed to increasing doses of HDAC inhibitors (HDACi) to induce histone acetylation. After 3 h, cells were fixed (1% paraformaldehyde in PBS) and permeabilized (Triton X-100 0.1% in PBS, RT). After washing (PBS-1% BSA), cells were pre-incubated in 10% Goat Serum PBS (30' at 4°). Cells were then incubated with a monoclonal antibody (in PBS-1% BSA; 1 hour RT) directed against acetylated histones and then with an anti-mouse FITC conjugate antibody (in PBS-1% BSA; 1 hour RT). After final washing, cells were FACS analysed.

2.2 HDAC Inhibition Assay

The HDAC activity assay was performed onto nuclear extract using an HDAC fluorescent activity assay kit (Biomol Inc.), according to manufacturer's recommendations. The assay was performed in two steps: first, 5 μg of HELA nuclear extract (HDAC activity) was added to a solution of HDAC inhibitor and substrate (acetylated lysine side chain, 116 μM) and the mixture was then incubated for 10 min at room temperature (25°. In the second step the reaction was stopped by the addition of a developer (15 min at room temperature). In this step a fluorophore was produced.

Fluorescence was analyzed using a Vector 3 fluorimeter (Perkin-Elmer) with a 355 nm excitation wavelength and detection of emitted light at 460 nm.

2.3 MTT Assay

MTT [3-(4,5-dimethylthiazol-2-yl)-2,5-diphenyltetrazolium bromide] assay is based on the ability of a mitochondrial dehydrogenase enzyme from viable cells to cleave the tetrazolium rings of the pale yellow MTT and form a dark blue formazan crystals which is largely impermeable to cell membranes, thus resulting in its accumulation within healthy cells. Solubilisation of the cells by the addition of a detergent results in the liberation of the crystals which are solubilized. The number of surviving cells is directly proportional to the level of the formazan product created. The color can then be quantified using a simple colorimetric assay. The results can be read on a multiwell scanning spectrophotometer (ELISA reader).

Tumor cell lines (HT29, MCF-7, PC3, U937) were incubated (24, 48 and 72 hour) with different concentrations of test compound. MTT (5 mg/ml in PBS) was added at different time points and incubated for 3-4 hours at 37° C. After incubation, medium containing MTT solution was removed and formazan crystals were solubilised with an organic solvent (DMSO/Ethanol absolute 1:1) before reading on scanning multiwell spectrophotometer (550-570 nm). The percentage of surviving cells is expressed as: (treated wells absorbance/control wells absorbance)×100

2.4 Cell Growth/Apoptosis/Cell Cycle

Suspension or adherent cells (HT29 or K562) were exposed to increasing doses of HDACi compounds to evaluate their biological response. For cell cycle and apoptosis analysis cells, after collecting, were fixed in 70% ethanol for 30 min.

Following wash, cells were resuspended in Propidium Iodide (PI; 50 μg/ml additioned to RNase (250 μg/ml)) and incubated for 3 h at room temperature.

Figure 3:
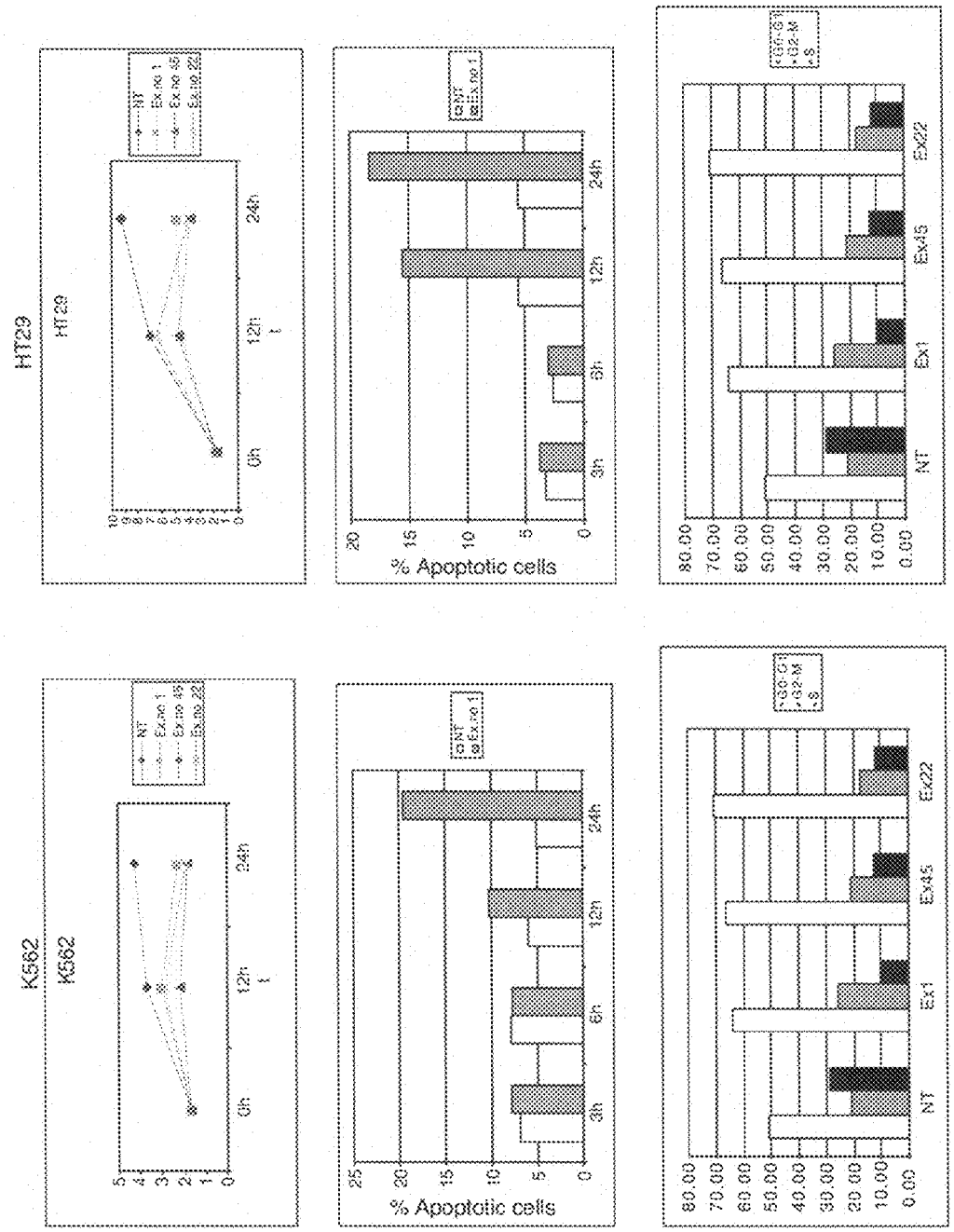
FIG. 3 is a Treatment of K562 and HT29 cells with the compounds of the invention: Effects on cell cycle, cell growth and apoptosis.

Samples were processed for flow cytometric (FC) analyses. FC was performed by FACScan Cytometer (Becton Dickinson). As shown in FIG. 3, the tested compounds were able to completely arrest cell growth, induse apoptosis and stimulate G0/G1 block.

In Vivo studies
Antitumor Activity Studies
2.5 Carciginogenesis Study and HDACi Administration Six-week-old female 129 mice were initially treated with 25 μg of DMBA (dissolved in 200 μl of acetone) painted onto the shaved back skin. Starting 2 weeks thereafter, mice were treated with 3 μg of TPA (dissolved in 200 μl of acetone) twice a week for the following 13 weeks. Visible skin tumors (papillomas) were evident after six weeks of TPA application. At the occurring of visible papillomas, HDACi administration was initiated. HDAC inhibitors were dissolved in glycerol/$H_2O$/DMSO (7:2:1). HDACi were administered to groups of both normal or DMBA-TPA treated animals, one group being considered sham (only vehicle administration). HDACi (or vehicle) was painted onto the shaved back skin (2×3 cm). All groups were treated twice a week for the following 6-7 weeks. All the visible tumors were counted weekly and dissected at the sacrifice ($CO_2$ inhalation) six weeks later.

2.6 Histological and Immunohistochemical Analysis

Tumors samples were fixed in 10% buffered formalin, processed for paraffin embedding and sectioned (4 μm). One series was stained with hematoxylin and eosin, while the others were immunohistochemically processed to detect levels of acetylated histones. In brief, after de-paraffinization, tissue hydratation by graded alcohol series, and antigen unmasking in citrate solution (pH 6), sections were quenched (3% $H_2O_2$ in TBS) and incubated with anti-acetylated histones (in TBS 1×-BSA 2%-NGS 2%-Tween 0.05%), for 2 hours at room temperature. Sections were then incubated with ready to use secondary antibody (DAKO Envision System HRP anti mouse) for 1 hour at room temperature and subsequently incubated in peroxidase substrate solution (1 drop of chromogen in 1 mL of DAB DAKO buffer). Finally sections were washed in $H_2O$ and dehydrate for mounting and observation.

Results
3.1 Histone Acetylation Assay and HDAC Inhibition Assay

According to the procedures mentioned in paragraphs 2.1 and 2.2, the present compounds were thus tested for their ability to inhibit histone deacetylases. The obtained results are schematized in Table 8.

TABLE 8

Summary of the measured activity (HDAC Inhibition Assay and Histone Acetylation Assay)

| compounds | Activity | Acetylation increment | Activity Biochem ASSAY |
|---|---|---|---|
| MC1632 | ++ | +++ | + |
| MC1610 | +++ | ++ | +++ |
| MC1624 | + | + | +++ |
| Ex. 1 | ++ | ++ | + |
| Ex. 2 | ++ | ++ | ++ |
| Ex. 5 | +++ | ++ | +++ |
| Ex. 61 | +++ | +++ | ++ |
| Ex. 7 | +++ | + | + |
| Ex. 9 | +++ | +++ | + |
| Ex. 22 | ++ | +++ | ++ |
| Ex. 24 | +++ | +++ | nd |
| Ex. 12 | +++ | ++ | nd |
| Ex. 30 | ++ | +++ | nd |
| Ex. 41 | + | ++ | nd |
| Ex. 43 | + | +++ | nd |
| Ex. 65 | + | +++ | nd |
| Ex. 63 | + | +++ | nd |
| Ex. 45 | ++ | +++ | nd |

IC50 range (nM): <100 = +++
>100, <200 = ++
>200, <600 = +
Acetylation Increment range: <4 times = +
>4 times, <6 times = ++
>6 times = +++

The data shown in Table 8 demonstrate that the tested compounds possess a powerful inhibiting activity against histone deacetylases.

3.2 MTT Assay

In accordance with the procedure described in paragraphs 2.3, the present compounds were tested on different cell lines for their capacity to induce proliferation block and/or cell death. The obtained results are schematized in Table 9.

TABLE 9

Activity MTT test compounds

| compounds | HT29 | MCF7 | PC3 | U937 |
|---|---|---|---|---|
| MC1632 | ++ | ++ | ++ | ++ |
| MC1610 | ++ | ++ | + | ++ |
| MC1624 | ++ | ++ | + | ++ |
| Ex. 1 | +++ | ++ | ++ | ++ |
| Ex. 2 | +++ | ++ | ++ | +++ |
| Ex. 5 | ++ | ++ | ++ | ++ |
| Ex. 61 | ++ | ++ | + | ++ |
| Ex. 7 | +++ | ++ | ++ | nd |
| Ex. 9 | +++ | + | ++ | ++ |
| Ex. 22 | +++ | ++ | +++ | ++ |
| Ex. 24 | +++ | ++ | ++ | nd |
| Ex. 12 | +++ | ++ | ++ | nd |
| Ex. 30 | ++ | ++ | ++ | nd |
| Ex. 41 | ++ | ++ | + | nd |
| Ex. 43 | ++ | ++ | ++ | nd |
| Ex. 65 | ++ | ++ | + | nd |
| Ex. 63 | ++ | ++ | ++ | nd |
| Ex. 45 | +++ | ++ | +++ | nd |

IC50 (μM) range: <0.5 = +++
>0.5, <5 = ++
>5 = +

The results shown in Table 9 indicate that the present compounds are able to induce proliferation block and/or cell death in a variety of tumor cell lines.

3.3 In Vivo Studies

In accordance with the procedures explained in paragraphs 2.5 and 2.6, cutis from normal mice or from mice exposed to DMBA-TPA treatment was analyzed by immunohistochemistry or stained with hematoxylin and eosin, respectively.

Figure 4:
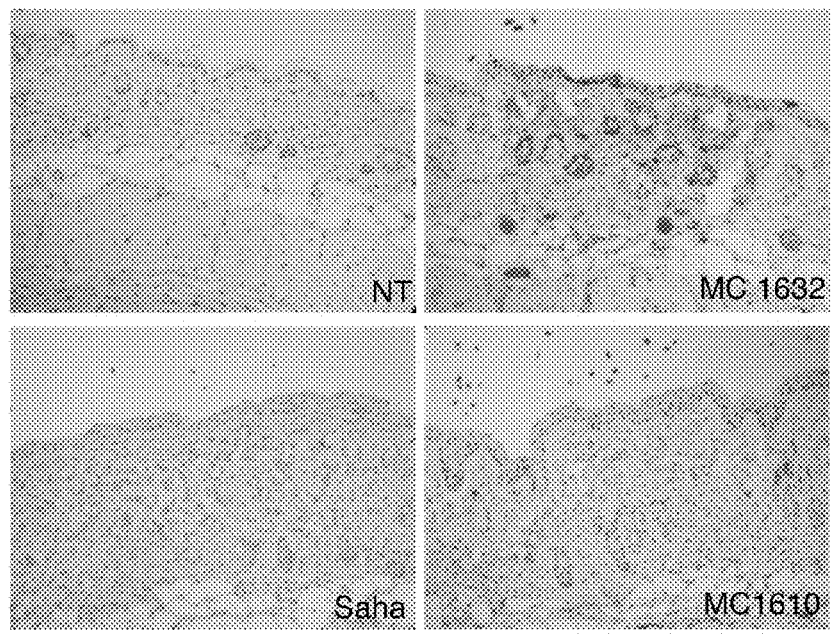
FIG. 4 is an Effect of the new HDACi administration on normal cutis (immunohistochemistry for detection of acetylated histones).
Figure 5:
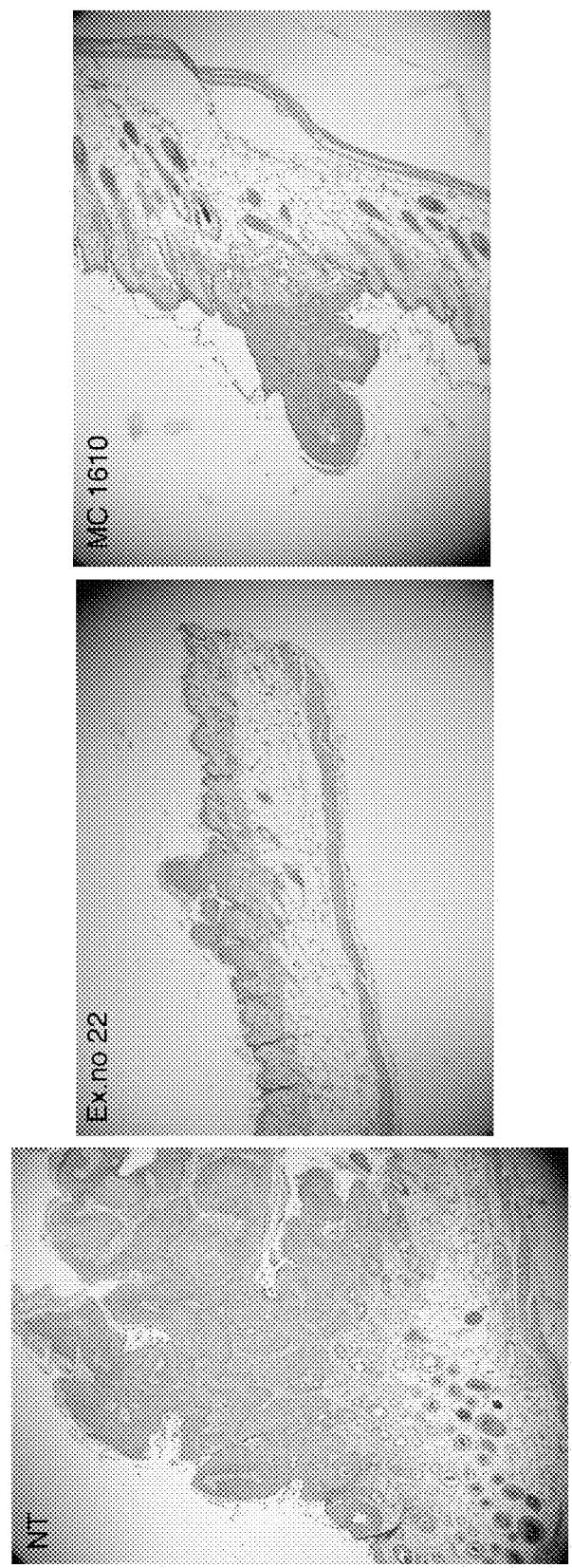
FIG. 5 is an Effect of the new HDACi administration on cutis after induction and occurrence of papillomas (histochemistry for detection of acetylated histones).
Figure 6:
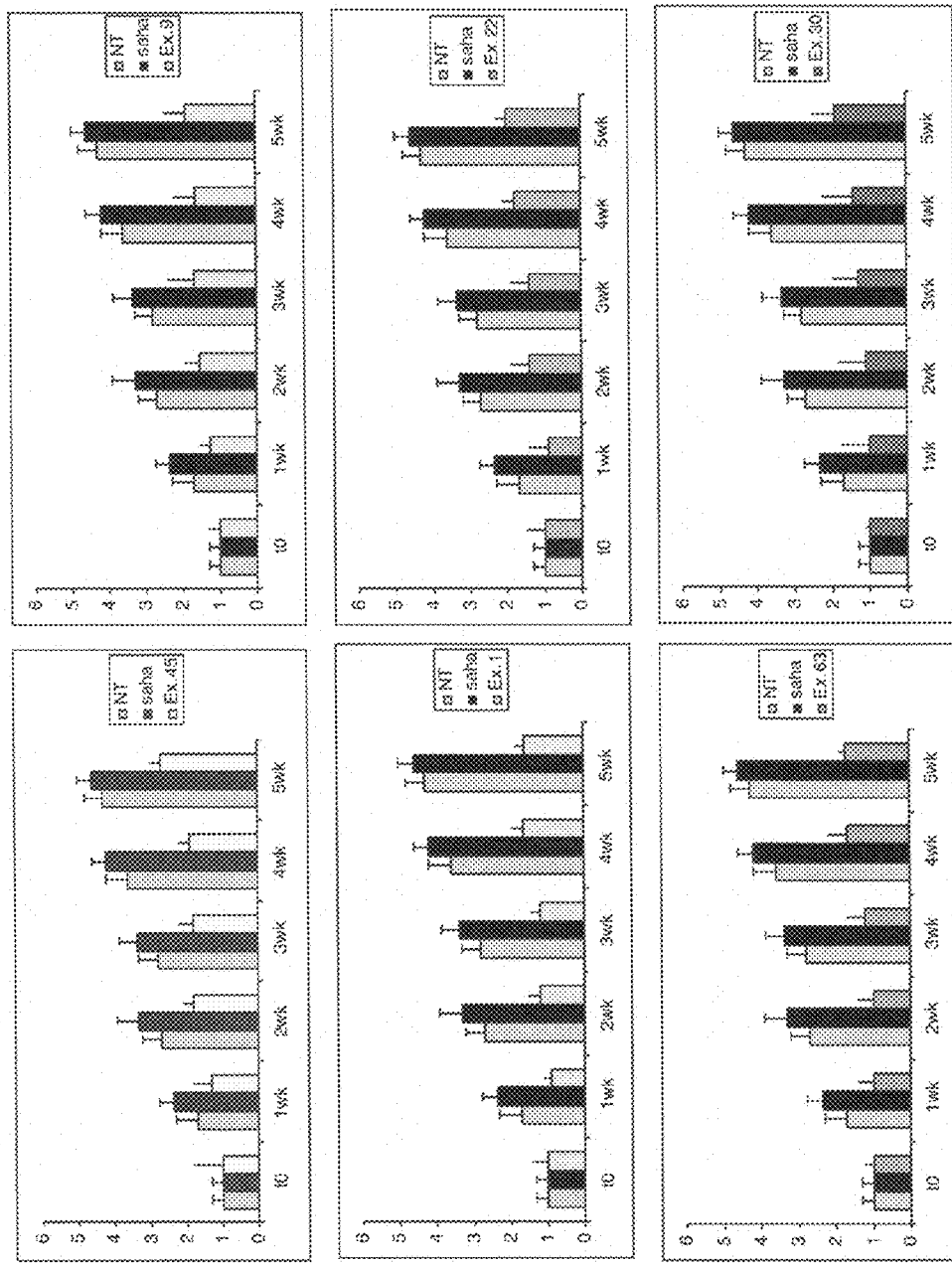
FIG. 6 is an Effect of treatments with the new HDACi on the number of papillomas.

Examples of the obtained results are represented in FIG. 4 and FIG. 5 which demonstrate that the tested compounds are able to strongly induce histone acetylation in normal animals and are to able to reduce the tumor size in treated animals. Moreover, the tested compounds are able to completely block the further number increase of induced papillomas as shown in FIG. 6.

What is claimed is:

1. A method of treating tumor diseases associated to the deregulation of the activity of histone deacetylases in a subject in need thereof, said tumor diseases selected among colon tumor, breast tumor, prostate tumor, lymphoma and cutaneous tumor, said method comprising administering to said subject, in an amount effective to treat said tumor diseases associated to the deregulation of the activity of histone deacetylases, a compound of formula (I)

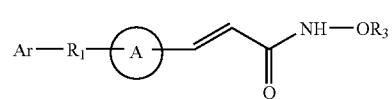
(I)

wherein:

$R_3$ is chosen among hydrogen, alkoxyalkyl;
Ar is an optionally substituted aryl or heteroaryl group;
A is chosen among:

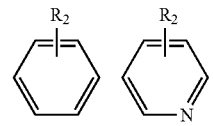

wherein $R_2$ is chosen among hydrogen, alkyl, cycloalkyl, aryl, arylalkyl, heterocyclyl, heterocyclylalkyl, halogen, haloalkyl, hydroxy, hydroxyalkyl, alkoxy, haloalkoxy, amino, aminoalkyl, alkylamino, (thio)carbonylamino, (thio)aminocarbonil, sulphonylamino, aminosulphonyl, (thio)acyl, (thio)acyloxy, (thio)alkoxycarbonyl, nitro and nitryl;

$R_1$ is chosen among:

(a)
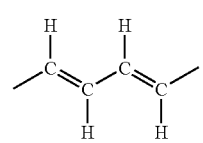

(b)
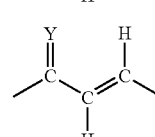

(c)
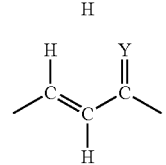

wherein Y represents O, S, NH, $CH_2$, NOH or $NOR_5$ where $R_5$ is an alkyl having from 1 to 4 carbon atoms.

2. The method of claim 1, wherein the compound of formula (I) is chosen from:
- 3-[3-fluoro-4-(3-oxo-3-phenyl-propenyl)-phenyl]-N-hydroxy-acrylamide;
- 3-[3-chloro-4-(3-oxo-3-phenyl-propenyl)-phenyl]-N-hydroxy-acrylamide;
- 3-[3-chloro-4-(3-oxo-3-o-tolyl-propenyl)-phenyl]-N-hydroxy-acrylamide;
- 3-{3-chloro-4-[3-(2-methoxy-phenyl)-3-oxo-propenyl]-phenyl}-N-hydroxy-acrylamide;
- 3-{3-chloro-4-[3-(2-fluoro-phenyl)-3-oxo-propenyl]-phenyl}-N-hydroxy-acrylamide;
- 3-{3-chloro-4-[3-(2-chloro-phenyl)-3-oxo-propenyl]-phenyl}-N-hydroxy-acrylamide;
- 3-[3-chloro-4-(3-oxo-3-m-tolyl-propenyl)-phenyl]-N-hydroxy-acrylamide;
- 3-{3-chloro-4-[3-(3-methoxy-phenyl)-3-oxo-propenyl]-phenyl}-N-hydroxy-acrylamide;
- 3-{3-chloro-4-[3-(3-fluoro-phenyl)-3-oxo-propenyl]-phenyl}-N-hydroxy-acrylamide;
- 3-{3-chloro-4-[3-(3-chloro-phenyl)-3-oxo-propenyl]-phenyl}-N-hydroxy-acrylamide;
- 3-[3-chloro-4-(3-oxo-3-p-tolyl-propenyl)-phenyl]-N-hydroxy-acrylamide;
- 3-{3-chloro-4-[3-(4-methoxy-phenyl)-3-oxo-propenyl]-phenyl}-N-hydroxy-acrylamide;
- 3-{3-chloro-4-[3-(4-fluoro-phenyl)-3-oxo-propenyl]-phenyl}-N-hydroxy-acrylamide;
- 3-{3-chloro-4-[3-(4-chloro-phenyl)-3-oxo-propenyl]-phenyl}-N-hydroxy-acrylamide;
- 3-[3-chloro-4-(3-oxo-3-thiophen-2-yl-propenyl)-phenyl]-N-hydroxy-acrylamide;
- 3-[3-fluoro-4-(3-oxo-3-o-tolyl-propenyl)-phenyl]-N-hydroxy-acrylamide;
- 3-{3-fluoro-4-[3-(2-methoxy-phenyl)-3-oxo-propenyl]phenyl}-N-hydroxy-acrylamide;
- 3-{3-fluoro-4-[3-(2-fluoro-phenyl)-3-oxo-propenyl]-phenyl}-N-hydroxy-acrylamide;
- 3-{4-[3-(2-chloro-phenyl)-3-oxo-propenyl]-3-fluoro-phenyl}-N-hydroxy-acrylamide;
- 3-[3-fluoro-4-(3-oxo-3-m-tolyl-propenyl)-phenyl]-N-hydroxy-acrylamide;
- 3-{3-fluoro-4-[3-(3-methoxy-phenyl)-3-oxo-propenyl]phenyl}-N-hydroxy-acrylamide;
- 3-{3-fluoro-4-[3-(3-fluoro-phenyl)-3-oxo-propenyl]-phenyl}-N-hydroxy-acrylamide;
- 3-{4-[3-(3-chloro-phenyl)-3-oxo-propenyl]-3-fluoro-phenyl}-N-hydroxy-acrylamide;
- 3-[3-fluoro-4-(3-oxo-3-p-tolyl-propenyl)-phenyl]-N-hydroxy-acrylamide;
- 3-{3-fluoro-4-[3-(4-methoxy-phenyl)-3-oxo-propenyl]phenyl}-N-hydroxy-acrylamide;
- 3-{3-fluoro-4-[3-(4-fluoro-phenyl)-3-oxo-propenyl]-phenyl}-N-hydroxy-acrylamide;
- 3-{4-[3-(4-chloro-phenyl)-3-oxo-propenyl]-3-fluoro-phenyl}-N-hydroxy-acrylamide;
- 3-[3-fluoro-4-(3-oxo-3-thiophen-2-yl-propenyl)-phenyl]-N-hydroxy-acrylamide;
- 3-{3-fluoro-4-[3-(4-morpholin-4-yl-phenyl)-3-oxo-propenyl]-phenyl}-N-hydroxy-acrylamide;
- N-hydroxy-3-{4-[3-(2-methoxy-phenyl)-3-oxo-propenyl]-phenyl}-acrylamide;
- N-hydroxy-3-{4-[3-oxo-3-(2-trifluoromethyl-phenyl)-propenyl]-phenyl}-acrylamide;
- N-hydroxy-3-{4-[3-oxo-3-(2-trifluoromethoxy-phenyl)-propenyl]-phenyl}-acrylamide;
- 3-{4-[3-(2-bromo-phenyl)-3-oxo-propenyl]-phenyl}-N-hydroxy-acrylamide;
- N-hydroxy-3-{4-[3-(3-methoxy-phenyl)-3-oxo-propenyl]-phenyl}-acrylamide;
- 3-{4-[3-(3-bromo-phenyl)-3-oxo-propenyl]-phenyl}-N-hydroxy-acrylamide;
- N-hydroxy-3-{4-[3-(4-methoxy-phenyl)-3-oxo-propenyl]-phenyl}-acrylamide;
- N-hydroxy-3-{4-[3-oxo-3-(4-trifluoromethyl-phenyl)-propenyl]-phenyl}-acrylamide;
- N-hydroxy-3-{4-[3-oxo-3-(4-trifluoromethoxy-phenyl)-propenyl]-phenyl}-acrylamide;
- 3-{4-[3-(4-bromo-phenyl)-3-oxo-propenyl]-phenyl}-N-hydroxy-acrylamide;
- 3-{4-[3-(4-diethylamino-phenyl)-3-oxo-propenyl]-phenyl}-N-hydroxy-acrylamide;
- N-hydroxy-3-{4-[3-(4-morpholin-4-yl-phenyl)-3-oxo-propenyl]-phenyl}-acrylamide;
- 3-[4-(3-furan-2-yl-3-oxo-propenyl)-phenyl]-N-hydroxy-acrylamide;
- N-hydroxy-3-[4-(3-oxo-3-thiophen-2-yl-propenyl)-phenyl]-acrylamide;
- N-hydroxy-3-{4-[3-oxo-3-(1H-pyrrol-2-yl)-propenyl]-phenyl}-acrylamide;
- 3-[4-(3-benzofuran-2-yl-3-oxo-propenyl)-phenyl]-N-hydroxy-acrylamide;
- 3-[4-(3-benzo[b]thiophen-2-yl-3-oxo-propenyl)-phenyl]-N-hydroxy-acrylamide;
- N-hydroxy-3-[4-(3-oxo-3-thiophen-3-yl-propenyl)-phenyl]-acrylamide;
- N-hydroxy-3-{4-[3-(3-methoxy-4-morpholin-4-ylmethyl-phenyl)-3-oxo-propenyl]phenyl}-acrylamide;
- 3-{4-[3-(3,4-difluoro-phenyl)-3-oxo-propenyl]phenyl}-N-hydroxy-acrylamide;
- 3-{4-[3-(3,5-difluoro-phenyl)-3-oxo-propenyl]phenyl}-N-hydroxy-acrylamide;
- 3-{4-[3-(2,5-difluoro-phenyl)-3-oxo-propenyl]phenyl}-N-hydroxy-acrylamide;
- 3-{4-[3-(2,6-difluoro-phenyl)-3-oxo-propenyl]phenyl}-N-hydroxy-acrylamide;
- N-hydroxy-3-[3-methoxy-4-(3-oxo-3-thiophen-2-yl-propenyl)-phenyl]-acrylamide;
- N-hydroxy-3-[3-methyl-4-(3-oxo-3-thiophen-2-yl-propenyl)-phenyl]-acrylamide;
- 4-{3-[4-(2-hydroxycarbamoyl-vinyl)-phenyl]-acryloyl}-benzoic acid methyl ester;
- 3-{3-[4-(2-hydroxycarbamoyl-vinyl)-phenyl]-acryloyl}-benzoic acid methyl ester;
- 3-{4-[3-(5-chloro-thiophen-2-yl)-3-oxo-propenyl]-phenyl}-N-hydroxy-acrylamide;
- N-hydroxy-3-{4-[3-(3-hydroxy-phenyl)-3-oxo-propenyl]-phenyl}-acrylamide;
- N-hydroxy-3-(4-{3-[4-(4-methyl-piperazin-1-yl)-phenyl]-3-oxo-propenyl}-phenyl)-acrylamide;
- N-hydroxy-3-[2-methoxy-4-(3-oxo-3-phenyl-propenyl)-phenyl]-acrylamide;
- 3-[2-fluoro-4-(3-oxo-3-phenyl-propenyl)-phenyl]-N-hydroxy-acrylamide;
- 3-[2-chloro-4-(3-oxo-3-phenyl-propenyl)-phenyl]-N-hydroxy-acrylamide;
- N-hydroxy-3-[4-(3-oxo-3-pyridin-3-yl-propenyl)-phenyl]-acrylamide;
- N-hydroxy-3-[4-(3-oxo-3-pyridin-2-yl-propenyl)-phenyl]-acrylamide;
- N-hydroxy-3-[4-(3-oxo-3-pyridin-4-yl-propenyl)-phenyl]-acrylamide;

N-hydroxy-3-[3-methyl-4-(3-oxo-3-phenyl-propenyl)-phenyl]-acrylamide;

N-hydroxy-3-[3-methoxy-4-(3-oxo-3-phenyl-propenyl)-phenyl]-acrylamide;

3-[3-fluoro-4-(3-oxo-3-pyridin-3-yl-propenyl)-phenyl]-N-hydroxacrylamide;

N-hydroxy-3-[5-(3-oxo-3-phenyl-propenyl)-pyridin-2-yl]-acrylamide;

N-hydroxy-3-{5-[3-(2-methoxy-phenyl)-3-oxo-propenyl]-pyridin-2-yl}-acrylamide;

N-hydroxy-3-[5-(3-oxo-3-thiophen-2-yl-propenyl)-pyridin-2-yl]-acrylamide;

3-{5-[3-(3,4-difluoro-phenyl)-3-oxo-propenyl]-pyridin-2-yl}-N-hydroxy-acrylamide.

3. The method of claim 1, wherein the cutaneous tumor disease is selected from melanomas and basal carcinomas.

* * * * *